US012115182B2

(12) United States Patent
Lau et al.

(10) Patent No.: US 12,115,182 B2
(45) Date of Patent: Oct. 15, 2024

(54) ADENOSINE A2A AGONISTS FOR THE TREATMENT OF CYTOKINE STORM SYNDROME

(71) Applicants: University of Maryland, Baltimore, Baltimore, MD (US); University of Virginia Patent Foundation, Charlottesville, VA (US)

(72) Inventors: Christine Lau, Charlottesville, VA (US); Yunge Zhao, Millersville, MD (US); Joel M. Linden, Charlottesville, VA (US); Barbara J. Mann, Charlottesville, VA (US); Preeti Chhabra, Waynesboro, VA (US); Kenneth Lewis Brayman, Charlottesville, VA (US); Sanford Feldman, Charlottesville, VA (US)

(73) Assignee: UNIVERSITY OF MARYLAND BALTIMORE, Baltimore, MD (US)

( * ) Notice: Subject to any disclaimer, the term of this patent is extended or adjusted under 35 U.S.C. 154(b) by 0 days.

(21) Appl. No.: 17/831,191

(22) Filed: Jun. 2, 2022

(65) Prior Publication Data
US 2023/0118877 A1    Apr. 20, 2023

Related U.S. Application Data

(60) Provisional application No. 63/340,179, filed on May 10, 2022, provisional application No. 63/313,479, filed on Feb. 24, 2022, provisional application No. 63/195,759, filed on Jun. 2, 2021.

(51) Int. Cl.
| | |
|---|---|
| *A61K 31/7076* | (2006.01) |
| *A61K 31/404* | (2006.01) |
| *A61K 31/519* | (2006.01) |
| *A61K 31/53* | (2006.01) |
| *A61K 45/06* | (2006.01) |
| *A61P 31/14* | (2006.01) |
| *A61P 37/06* | (2006.01) |

(52) U.S. Cl.
CPC ........ *A61K 31/7076* (2013.01); *A61K 31/404* (2013.01); *A61K 31/519* (2013.01); *A61K 31/53* (2013.01); *A61K 45/06* (2013.01); *A61P 31/14* (2018.01); *A61P 37/06* (2018.01)

(58) Field of Classification Search
None
See application file for complete search history.

(56) References Cited

FOREIGN PATENT DOCUMENTS

WO    WO-2021240568 A1 * 12/2021

* cited by examiner

*Primary Examiner* — Traviss C McIntosh, III
(74) *Attorney, Agent, or Firm* — Nevrivy Patent Law Group P.L.L.C.

(57) ABSTRACT

The present invention relates methods of treating cytokine storm syndrome comprising administering to a patient in need thereof a therapeutically effective amount of an adenosine $A_{2A}$ receptor agonist.

23 Claims, 39 Drawing Sheets

Fig. 3
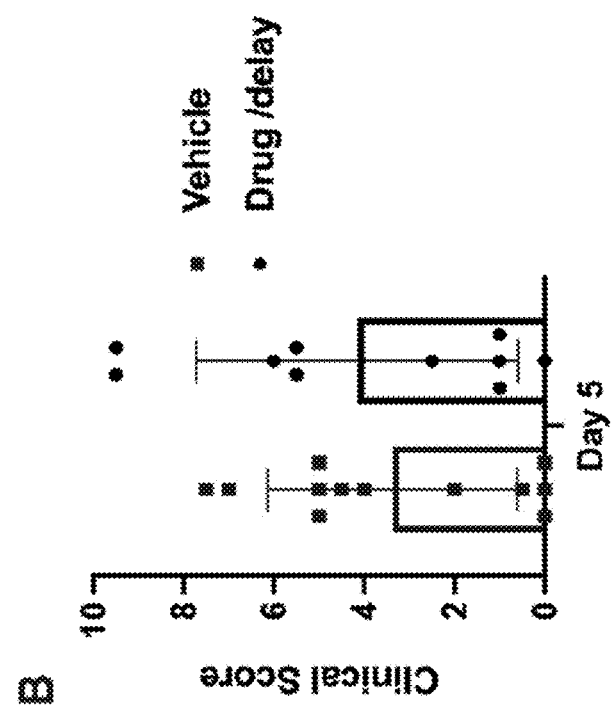
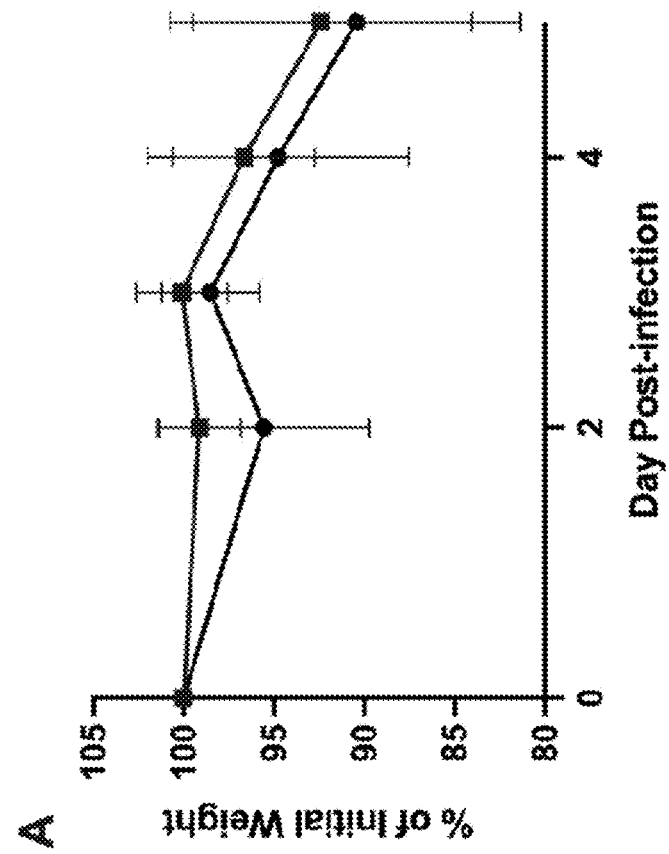

Fig. 11 (Cont.)
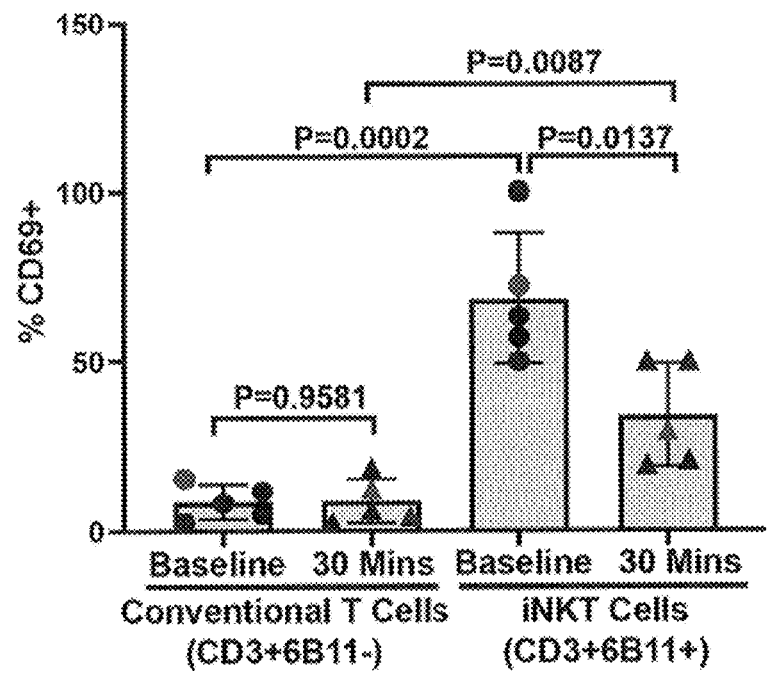
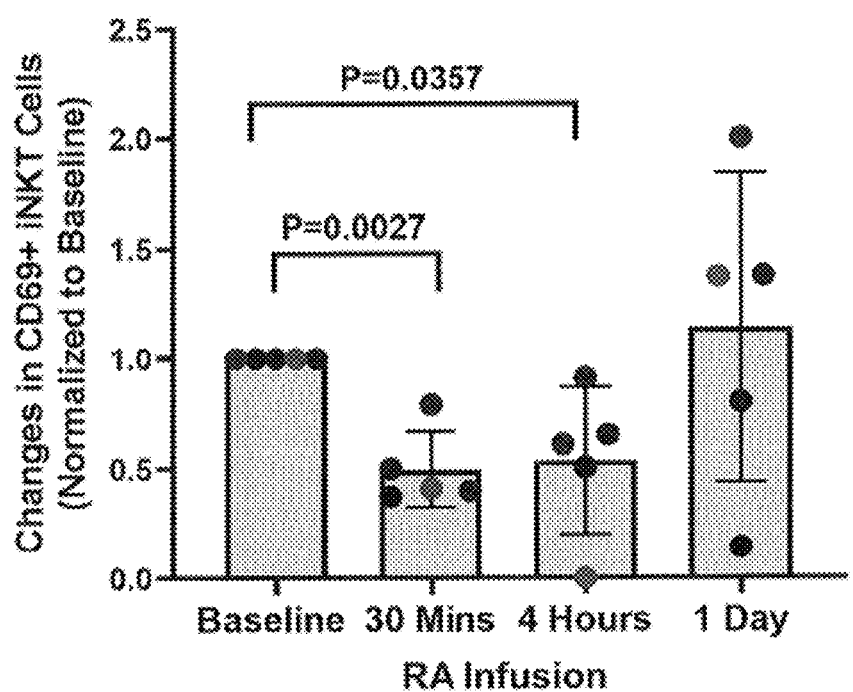

Fig. 14
A
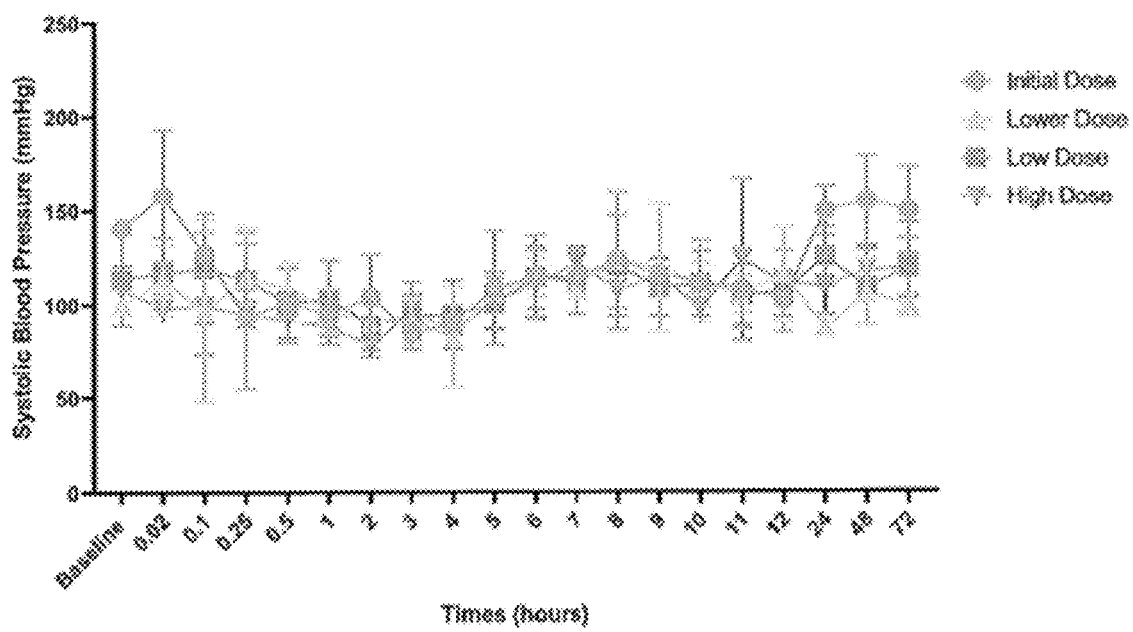
B
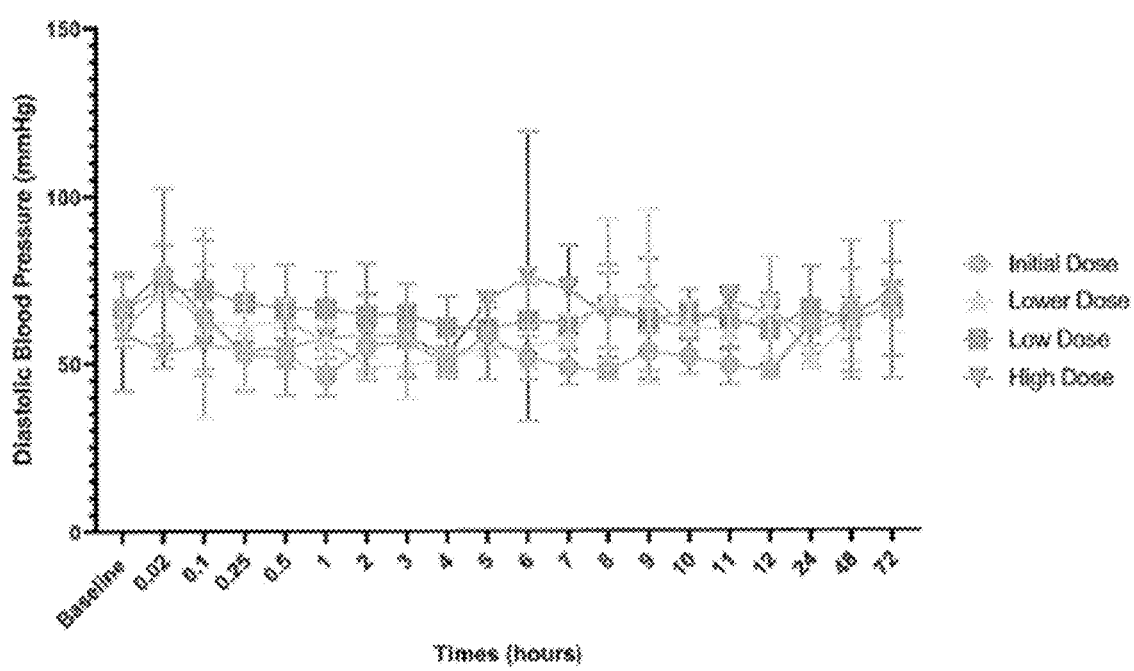

Fig. 15
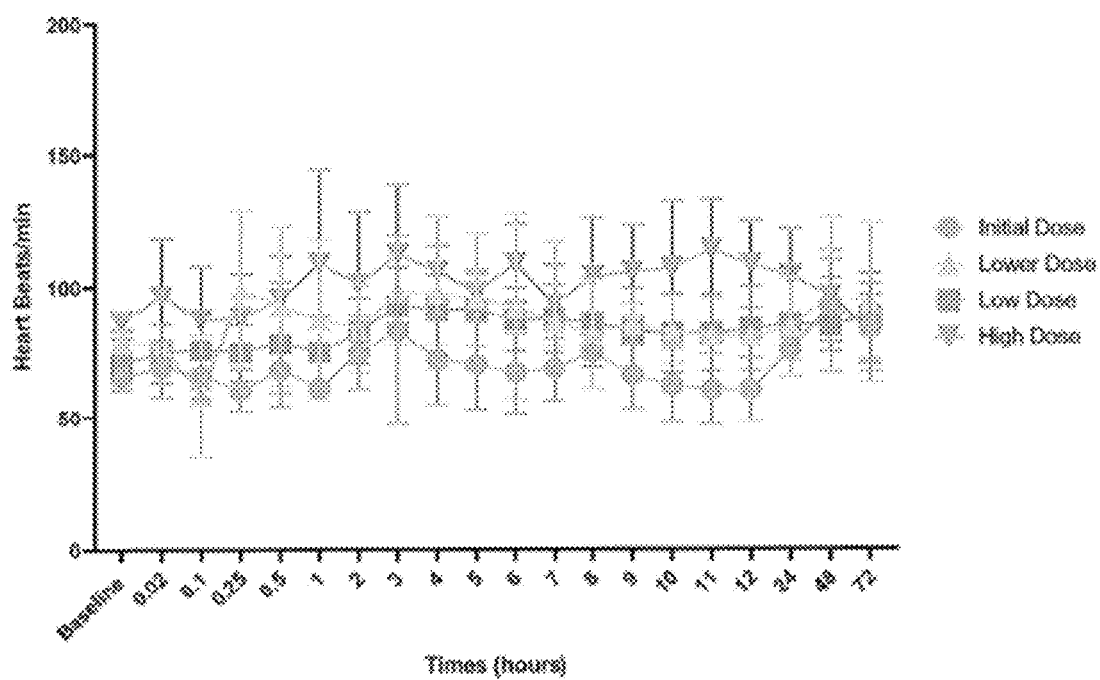
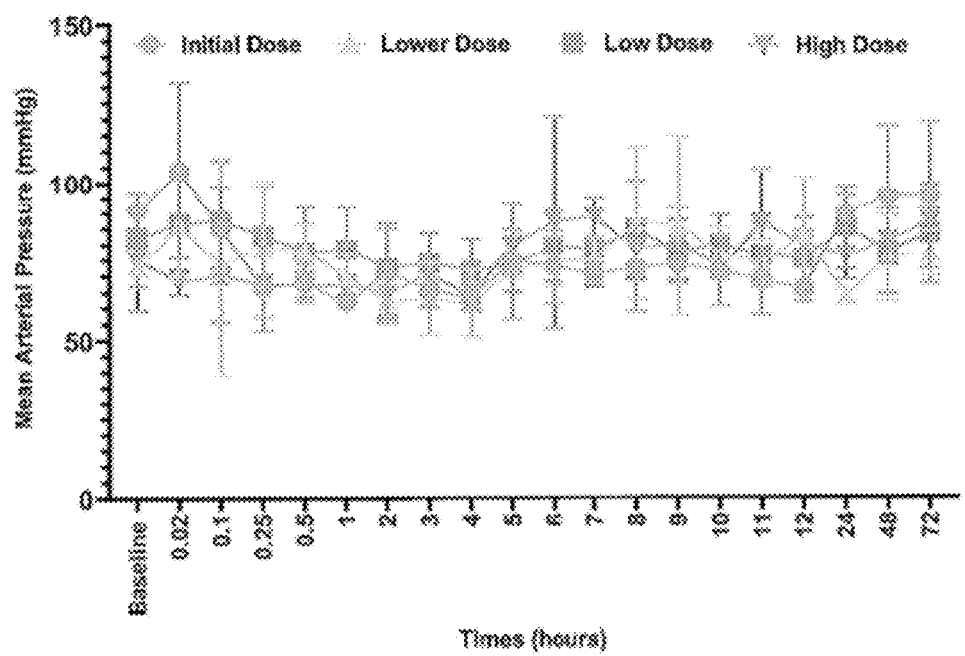

Fig. 16
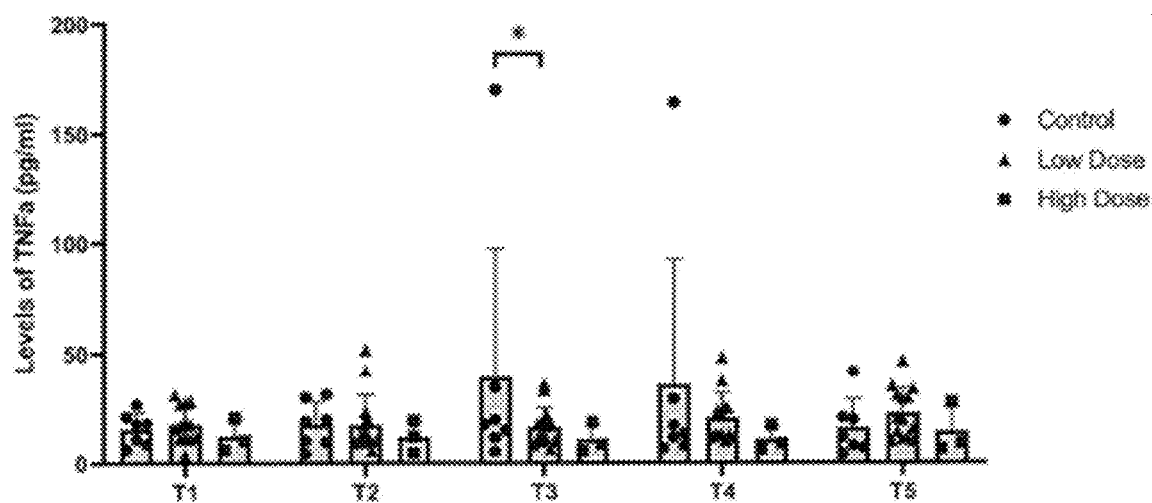
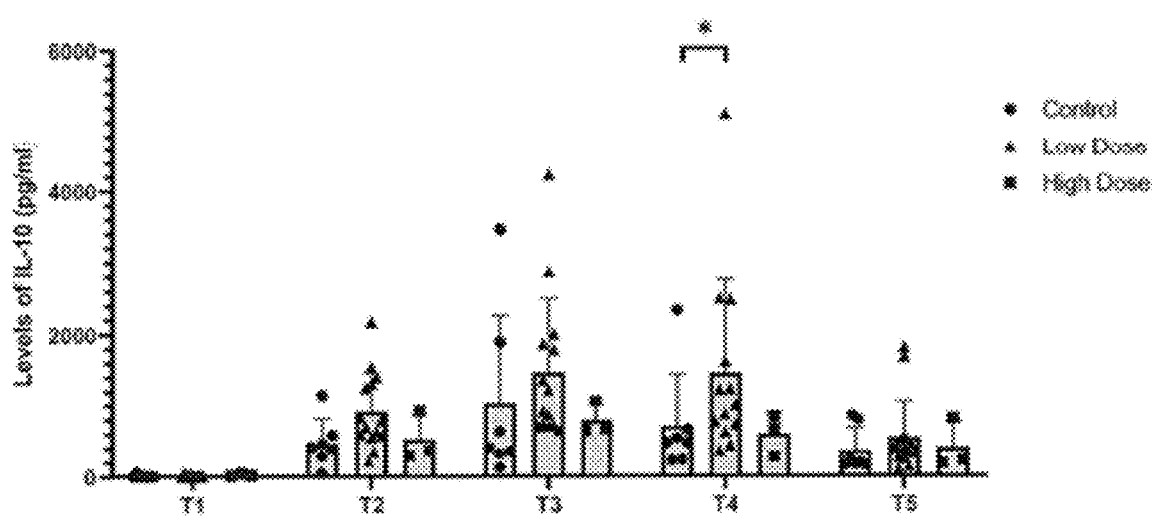

Fig. 19
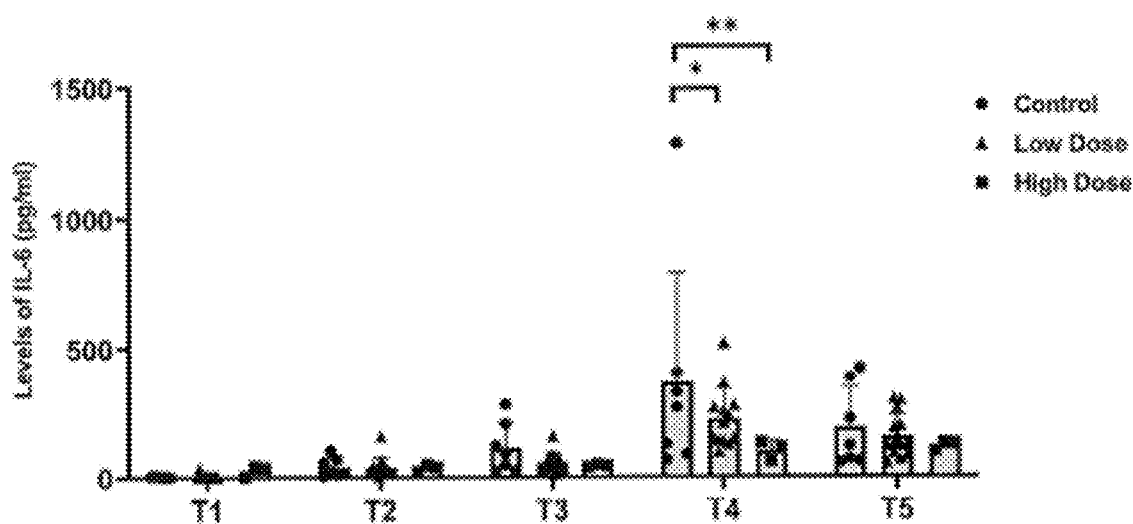
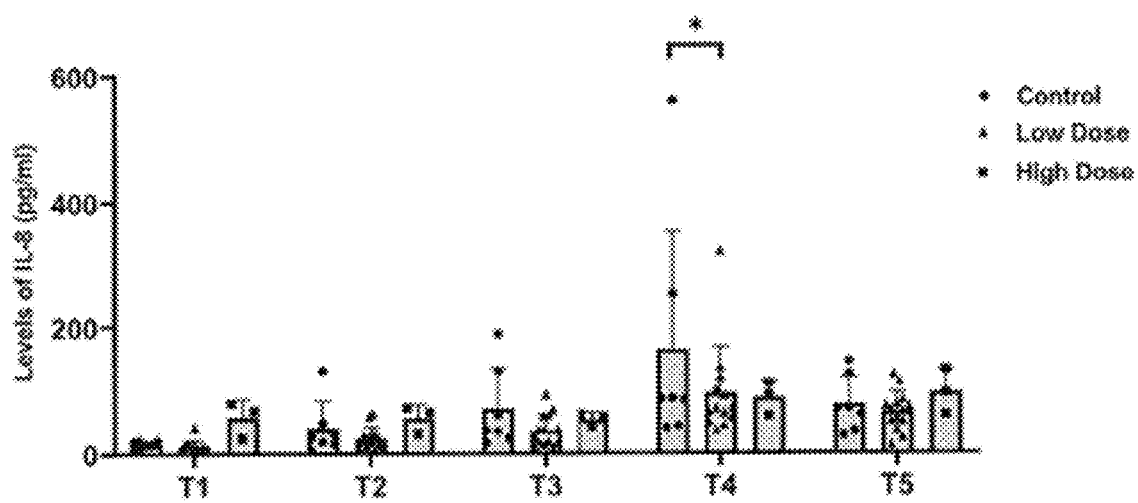

Fig. 22 (Cont.)
D
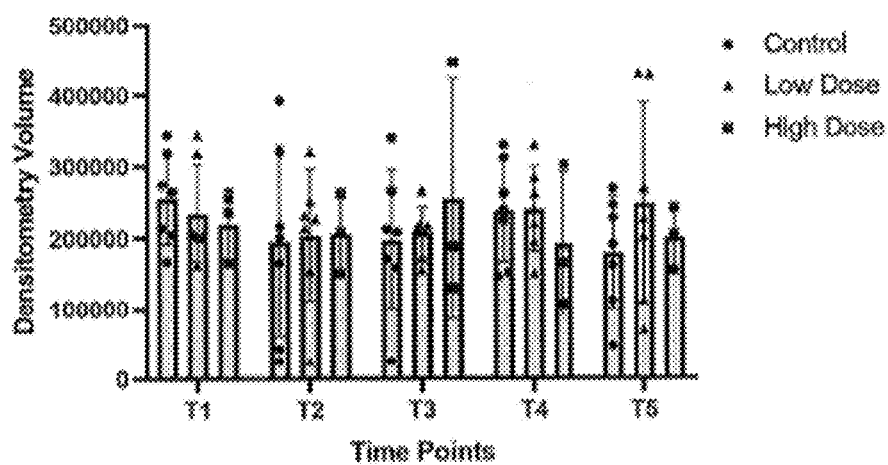
E
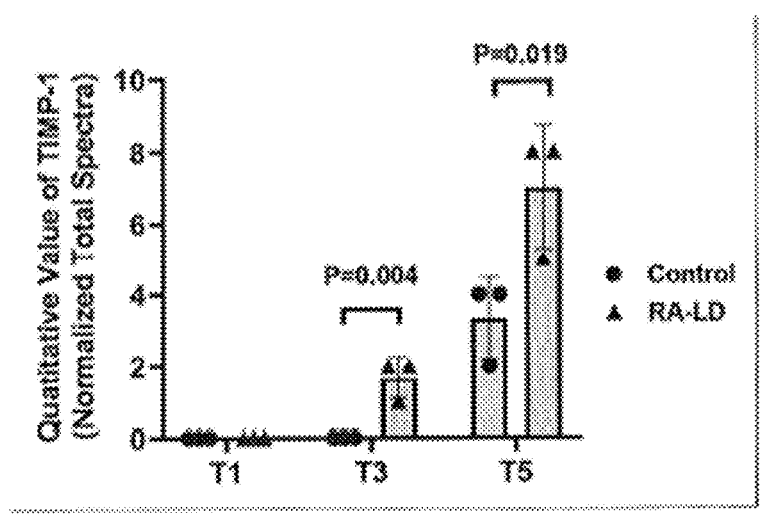

Fig. 23
A
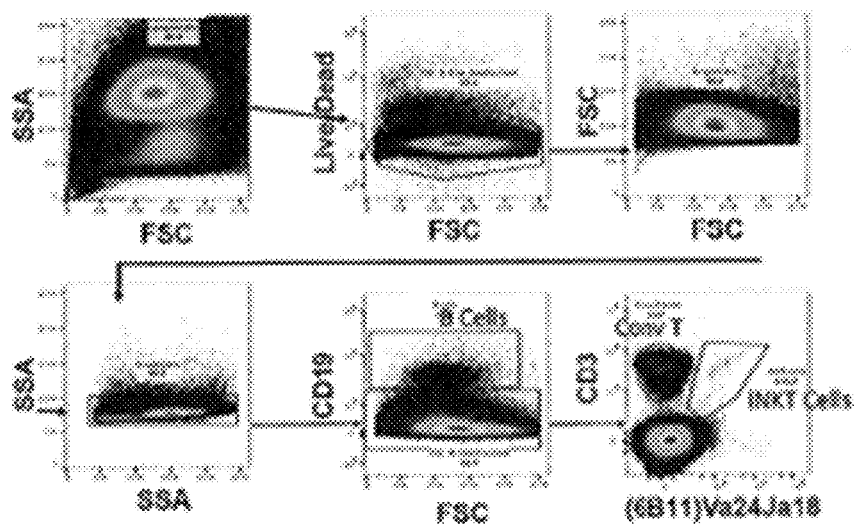
B
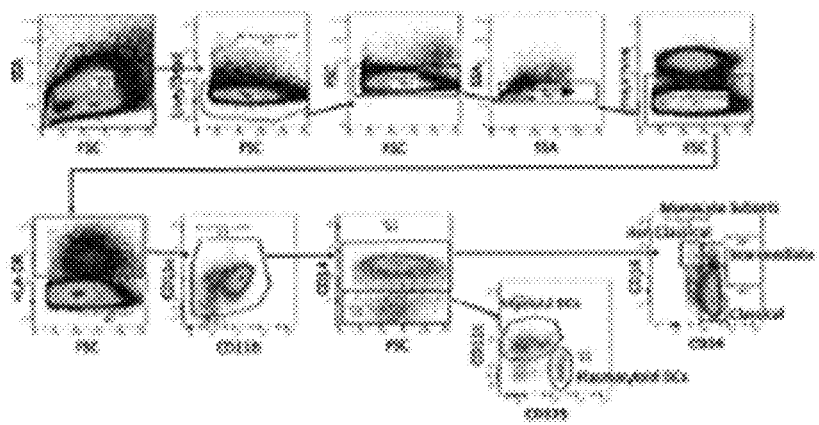
C
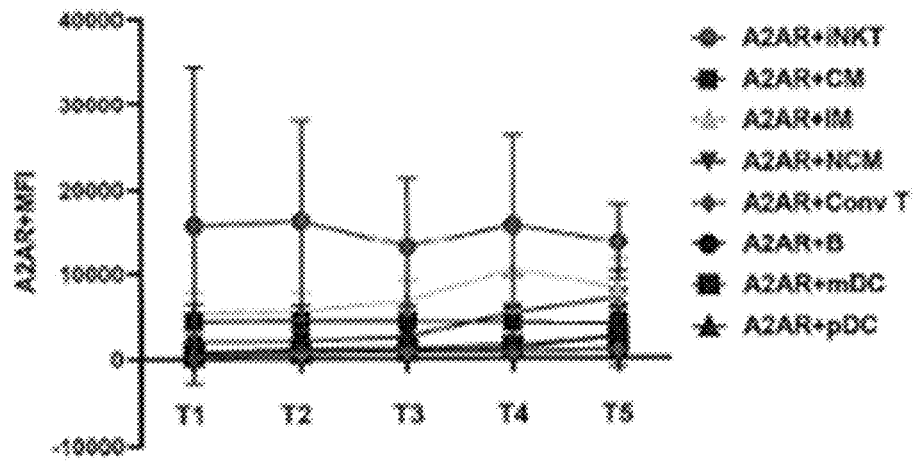

Fig. 24
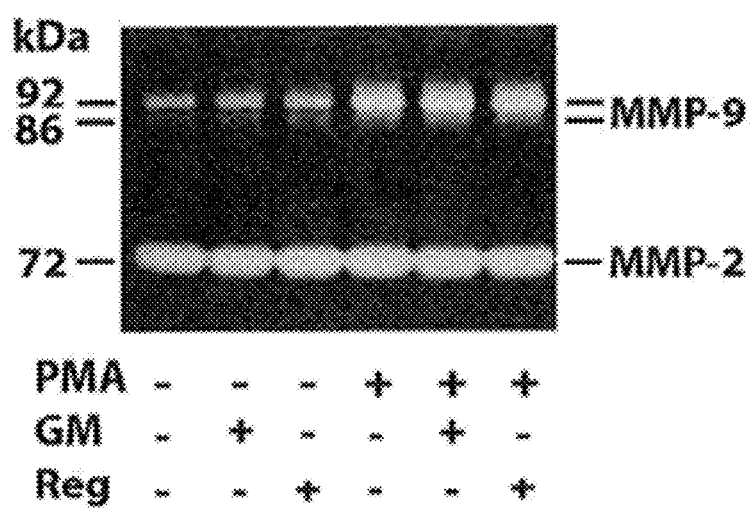
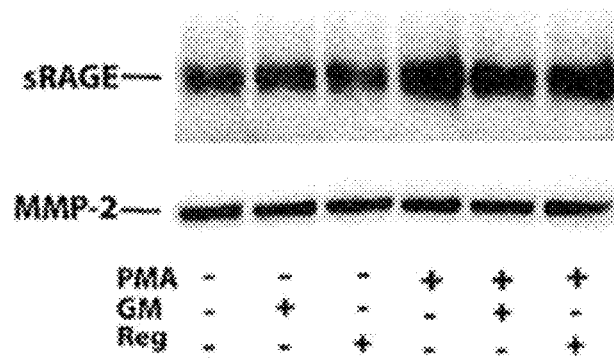

Fig. 25
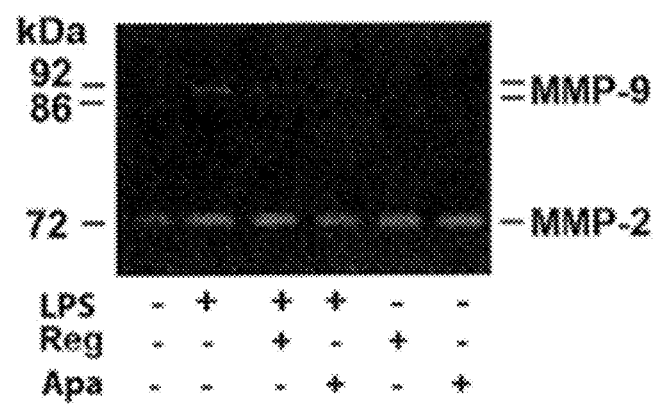
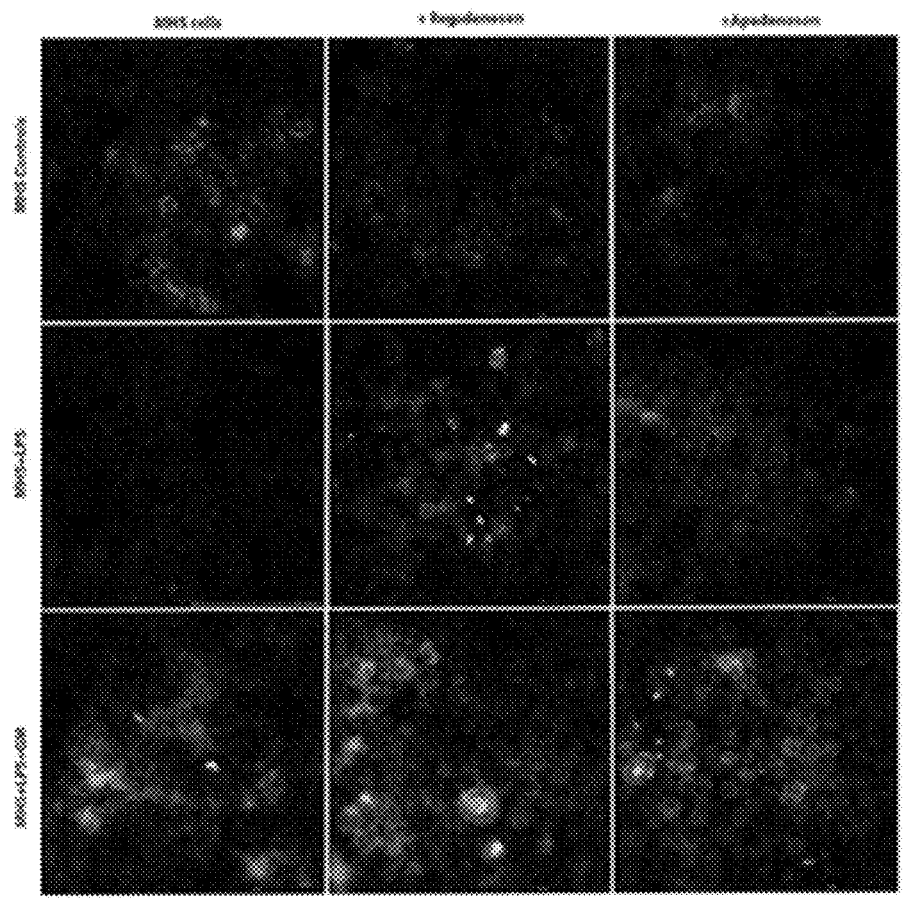

Fig. 26
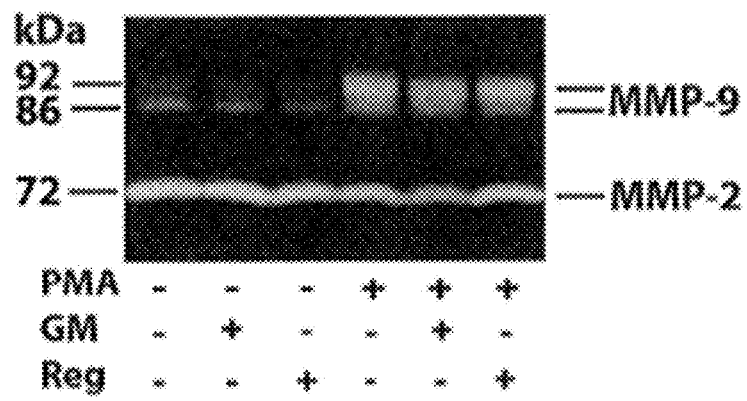
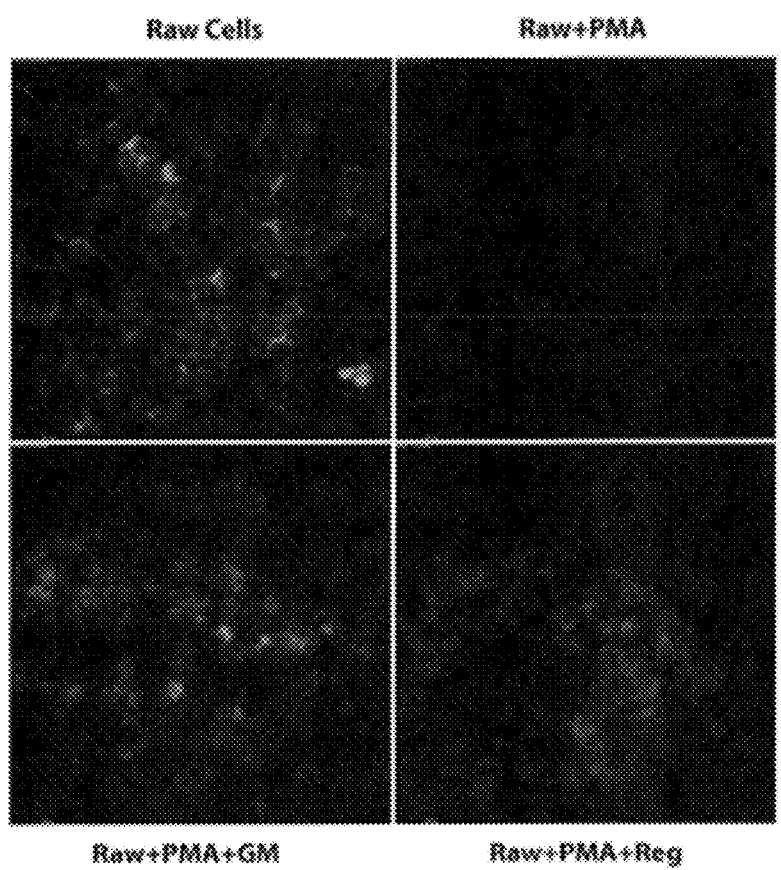

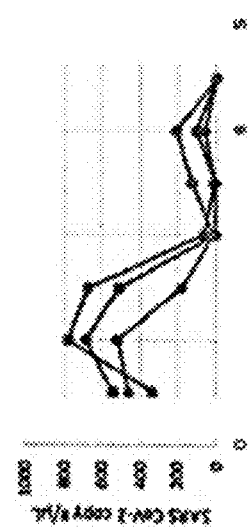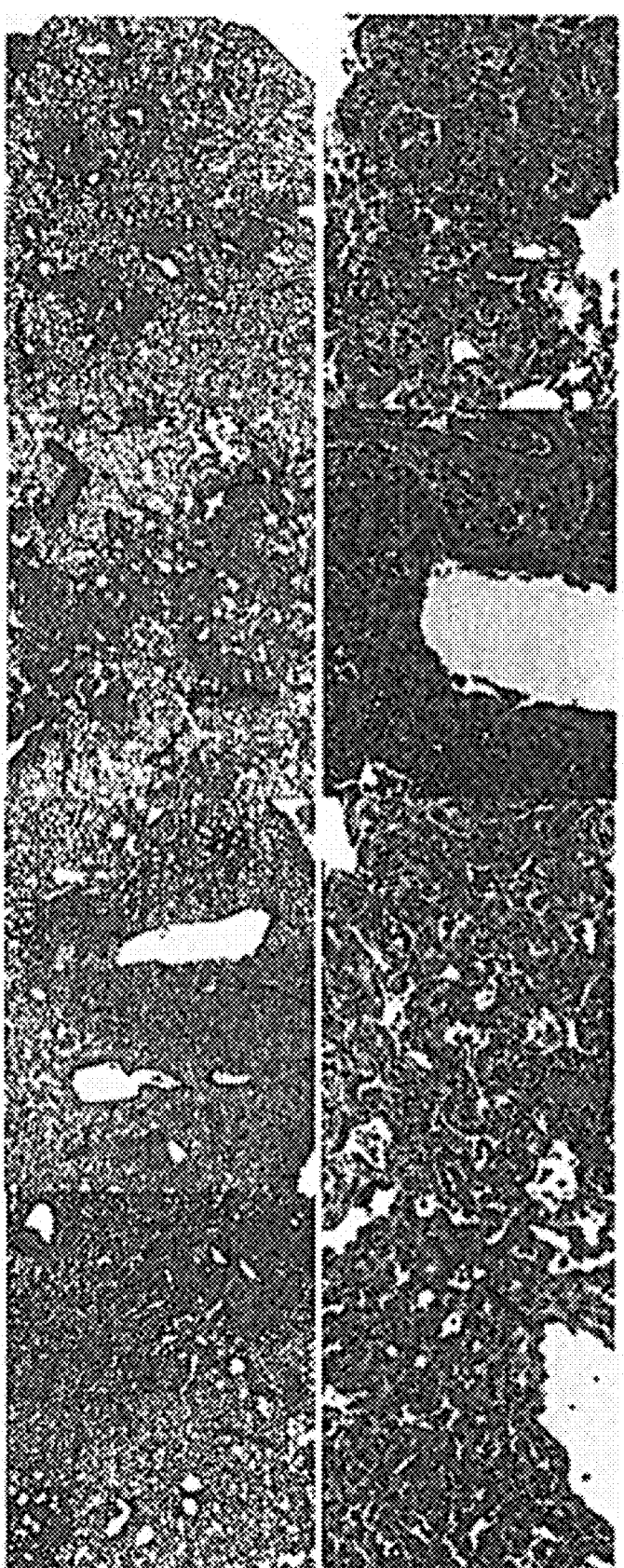
Fig. 31

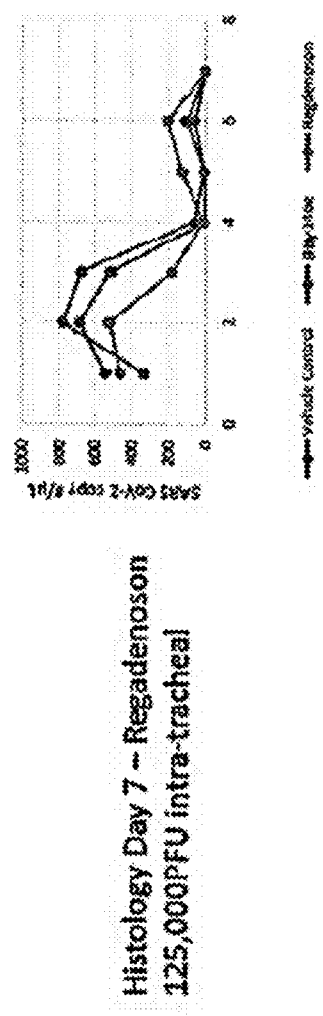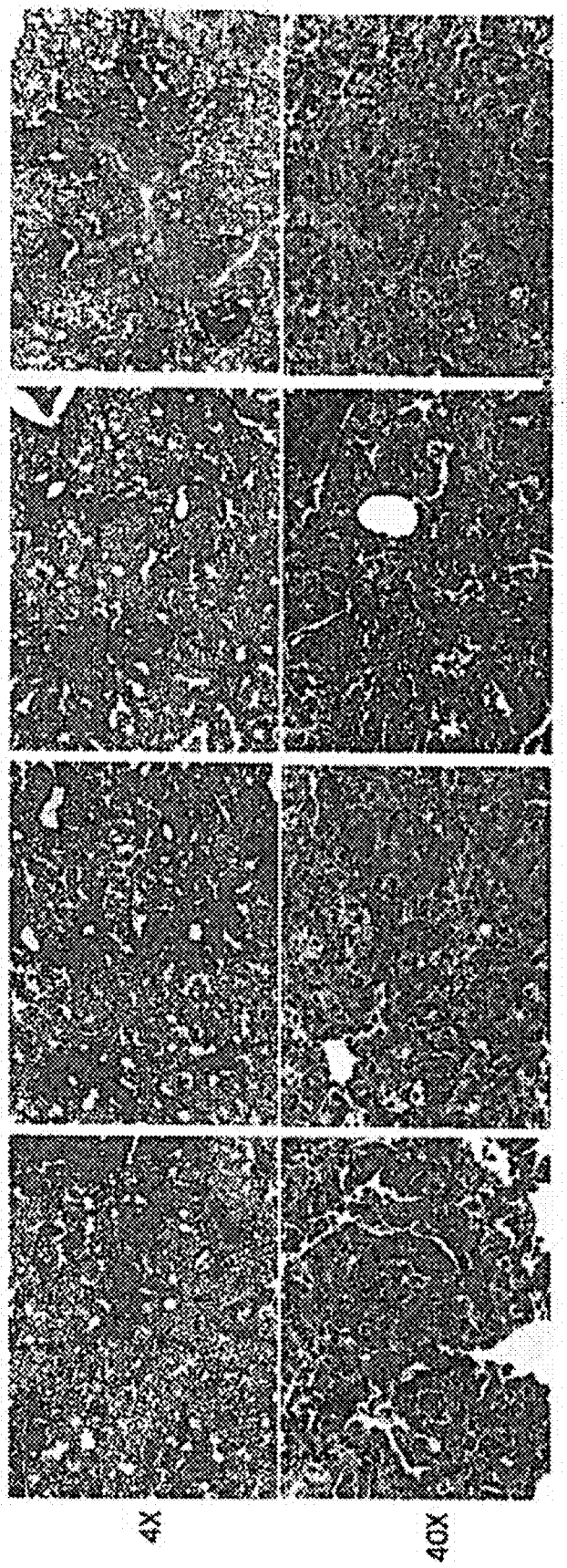
Fig. 35

ADENOSINE A2A AGONISTS FOR THE TREATMENT OF CYTOKINE STORM SYNDROME

CROSS-REFERENCE TO RELATED APPLICATIONS

This application claims the benefit of U.S. Provisional Application No. 63/195,759, filed Jun. 2, 2021, U.S. Provisional Application No. 63/313,479, filed Feb. 24, 2022, and U.S. Provisional Application No. 63/340,179, filed May 10, 2022, the contents of which are hereby incorporated by reference in their entireties.

STATEMENT REGARDING FEDERALLY SPONSORED RESEARCH OR DEVELOPMENT

This invention was made with government support under Grant Number HL128492 awarded by the National Institutes of Health. The government has certain rights in the invention.

FIELD OF THE INVENTION

The field of the invention relates to pharmaceuticals and medicine, in particular therapeutics for the treatment of cytokine storm syndrome.

BACKGROUND OF THE INVENTION

COVID-19, the Coronavirus disease caused by severe acute respiratory syndrome corona virus 2 (SARS CoV-2), represents a public health crisis of global proportions (SHARMA et al., Int. J. Antimicrob. Agents, (2020), 56, 106054). Declared a pandemic by the World Health Organization (WHO) on Mar. 11, 2020, this disease continues to spread aggressively across the world. Almost all patients with COVID-19 present with lung involvement; the activation of iNKT cell and a subgroup of patients exhibit life-threatening complications such as Acute Respiratory Distress Syndrome (ARDS) (Xu et al., Lancet Respir. Med., (2020), 8, 420-422). This subgroup of patients first develops severe pneumonia in the second week of infection, accompanied by high levels of circulating cytokines ("cytokine storm"), profound lymphopenia, eosinopenia, substantial mononuclear cell infiltration in the lungs, heart, spleen, lymph nodes and kidney, and an increased neutrophil-to-lymphocyte ratio (Li et al., J. Pharm. Anal., (2020), 10, 102-108; Xu et al., Lancet Respir. Med., (2020), 8, 420-422; Merad et al., Nat. Rev. Immunol., (2020), pg. 355-362). These symptoms eventually progress to ARDS, multi-organ failure and disseminated intravascular coagulation (DIC) (Xu et al., Lancet Respir. Med., (2020), 8, 420-422; Zaim et al., Curr. Probl. Cardiol., (2020), 45, 100618).

Although there has been rapid development of protective vaccines, emergency-use approved therapies for COVID-19 are limited. Remdesivir, given intravenously, is a nucleoside analog that targets the viral RNA polymerase, was the first drug officially approved by the Federal Drug Administration for COVID-19 treatment. More recently, the FDA has also authorized "emergency use authorization" of oral Paxlovid™ for the treatment of mild to moderate COVID-19. Paxlovid™ is a combination of nirmatrelvir, which also targets viral replication, and ritonavir, which extends the half-life of nirmatrelvir. Paxlovid™ is reported to reduce hospital admissions and death in high-risk individuals (Mahase et al., BMJ n2713, (2021), https://doi.org/10.1136/bmj.n2713; Owen et al., Science, (2021), 374, 1586-1593). Administration of these antivirals is associated with shortened recovery times and less respiratory tract infection in hospitalized patients (Beigel et al., N. Engl. J. Med., (2020), 383, 1813-1826). The use of remdesivir is controversial, as some studies have found that the treatment provides little benefit to hospitalized patients (WHO Solidarity Trial Consortium, N. Engl. J. Med., (2021), 384, 497-511). However, combining remdesivir with other drugs was shown to be superior to remdesivir alone. The anti-inflammatory glucocorticosteroid dexamethasone has shown effectiveness in reducing COVID-19-related deaths, and significantly reducing hospital stays (The Recovery Collaborative Group, N. Engl. J. Med., (2021), 384, 693-704), but is used at a low dose of only 6 mg/day to limit immunosuppression. Combining dexamethosome and remdesivir has been reported to reduce mortality and the need for mechanical ventilation (Benfield et al., Clin. Infect. Dis., (2021), ciab536. https://doi.org/10.1093/cid/ciab536). Currently, remdesivir and dexamethasone are indicated as standard-of-care treatment for COVID-19 patients with mild-moderate disease and not requiring high flow oxygen, according to guidelines of the National Institute of Health, USA. The combination of remdesivir with baricitinib, a JAK kinase inhibitor, has proven superior to remdesivir alone by shortening hospital stays (Kalil et al., N. Engl. J. Med., (2021), 384, 795-807). Other treatments aimed at attenuating immune pathogenesis related to cytokine storm syndromes include amongst others: IFN-γ neutralization, IL-6 receptor blockade or neutralization, B-cell ablation with rituximab, T cell-directed immunomodulation, T-cell ablation with anti-thymocyte globulin corticosteroids, IL-1 family member cytokines blockade including blockade of IL-18 binding protein, IL-1β, IL-33 receptor, and JAK inhibition (Kumar et al., Immunol., (2021) 12, 752227).

In a case series, aerosolized adenosine administered twice daily was found to increase (>30%) PaO2/FiO2-ratio in 13 out of 14 patients, despite it's very short half live (Correale et al., 2020). In another case report, two severely ill COVID-19 patients treated with inhaled adenosine exhibited a rapid improvement in lung function and one recovered (Spiess et al., Pharmacol, (2021), 12, 676577).

Adenosine is a potent autocrine and paracrine immunosuppressive nucleoside involved in regulating both the innate and adaptive immune responses via four widely expressed G protein-coupled receptors $A_1$, $A_{2A}$, $A_{2B}$ and $A_3$ (Chhabra et al., Curr. Diabetes Rev., (2012), 8:419-433). $A_{2A}$ or $A_{2B}$ adenosine receptor occupancy in most immune cells activates endogenous immunosuppressive pathways that act to reduce tissue injury and inflammation, and promotes repair by increasing oxygen supply/demand ratio, inhibiting pro-inflammatory cells and cytokines, decreasing endothelial adhesion molecule expression, and stimulating angiogenesis (Chhabra et al., Curr. Diabetes Rev., (2012), 8:419-433; Thiel et al., PLoS Biol., (2005), 3, e174).

Adenosine $A_{2A}$ receptor ($A_{2A}$R) activation plays a critical role in providing lung protection from enhanced neutrophil accumulation, lung vascular permeability, and impairment of lung gas exchange (Chhabra et al., Curr. Diabetes Rev., (2012), 8:419-433; Thiel et al., PLoS Biol., (2005), 3, e174). In asthma and COPD patients, suppression of leukocyte influx into broncho-alveolar lavage (BAL) fluid and reduction of inflammatory cell activation by $A_{2A}$R agonists contributed to immunosuppressive activity (Fozard et al., J. Pharmacol, (2002), 438, 183-188). Activation of $A_{2A}$Rs on myeloid cells attenuated cytokine release and the adhesion and extravasation of neutrophils to the pulmonary alveolar space following LPS-induced lung injury (Reutershan et al., J. Immunol, (2007), 179, 1254-1263).

Regadenoson (also known as CVT-3146) and apadenoson (also known as ATL-146e) are $A_{2A}R$ agonists. Regadenoson is used clinically for myocardial perfusion imaging because of its ability to induce coronary vasodilation without exercise and with few serious side-effects (Iskandrian et al., J. Nucl. Cardiol, (2007), 14, 645-658). Apadenoson is a more potent $A_{2A}R$ selective agonist; it has been shown to improve survival in a mouse *Escherichia coli* model of sepsis and was synergistic with the antibiotic Ceftriaxone (Sullivan et al., J. Infect. Dis., (2004), 189: 1897-1904). Both regadenoson and apadenoson protect animal and human lungs from ischemia-reperfusion or transplant-injury (Ellman et al., J. Surg. Res, (2008), 149, 3-8; Lau et al., J. Heart Lung Transplant, (2020), 39, 563-570). ATL146e (apadenoson) also reduced joint inflammation in combination with antibiotics in a rabbit septic arthritis model without interfering with bacterial clearance (Cohen et al., J. Orthop. Res., (2005), 23:1172-1178).

There is a need for new therapies to address cytokine storm syndrome, particularly in COVID-19 patients as well as other viral, bacterial or fungal infections that compromise pulmonary function. The foregoing description of the background is provided to aid in understanding the invention, and is not admitted to be or to describe prior art to the invention.

SUMMARY OF THE INVENTION

It is to be understood that both the foregoing general description of the invention and the following detailed description are exemplary, and thus do not restrict the scope of the invention.

The present invention is based on the surprising discovery that regadenoson, a selective A2A receptor agonist, is effective in treating cytokine storm syndrome, in particular, in COVID-19 patients. In addition, in K18-ACE2 transgenic mice that usually die in response to SARS-CoV-2 infection, treatment with regadenoson significantly reduces mortality. Without being bound by theory, it is believed that the agonist works by reducing the activation of iNKT cells that directly and indirectly produce proinflammatory cytokines and thereby reduce or preventing an aggressive inflammatory response that sometimes accompanies COVID-19 infection.

In one aspect, the invention provides a method of treating cytokine storm syndrome comprising administering to a patient in need thereof a therapeutically effective amount of an adenosine A2A receptor agonist. In some embodiments, the cytokine storm syndrome is caused by a viral, bacterial, or fungal infection.

In some embodiments, from 0.1-10 ug/kg body weight/h of the A2A agonist is administered to the subject over 6-48 hours. In some embodiments, the A2A agonist is administered as a single dose during an infusion over 1-48 h. In some embodiments, the A2A agonist is administered as a loading dose of 0.5-10 ug/kg body weight/hour for 30 minutes followed by administering a maintenance dose of 0.1-5 ug/kg body weight/h infused over 6-48 hours.

In some embodiments, the A2A receptor agonist is selected from the group consisting of regadenoson, ATL-146e (apadenoson), ATL-146a, ATL-193, ATL-2037, binodenoson, ATL-313, ATL-1222, ATL1223, IBMECA, Cl-IB-MECA, WRC0470, 2-hexynyl-NECA, adenosine, compound 4g [PMID 22220592; 6-(2,6-Dimethylpyridin-4-Y1)-5-Phenyl-1,2,4-Triazin-3-Amine], NECA, UK-431 097, CGS-21680, or GR79236, indirubin-3'-monoxime. 2-propynyl adenosine analogs having A2A agonist activity.

In some embodiments agents that elevate extracellular levels of adenosine can be used to activate A2A receptors. Low doses of methyltrexate cause an increase in extracellular adenosine by stimulating the translocation of adenine nucleotides from inside to outside of cells where they are rapidly metabolized to adenosine. Dipyridamole is an inhibitor of equilibrative nucleoside transport and also elevates extracellular adenosine.

In some embodiments, the A2A agonist is administered by a route selected from the group consisting of intravenous bolus (IV-bolus), intramuscular (IM), oral, via aerosol, and transdermal. In some embodiments, the A2A agonist is administered by IV infusion.

In some embodiments, the cytokine storm syndrome is caused by a viral infection. In some embodiments, the patient has a SARS-CoV-2 infection. In some embodiments, the cytokine storm syndrome is caused by a bacterial infection. In some embodiments, the cytokine storm syndrome is caused by a fungal infection.

In some embodiments, the method comprises administering an additional therapeutic agent to treat the infection. In some embodiments, the additional agent comprises a therapeutically effective amount of an anti-viral agent. In some embodiments, the additional agent comprises a therapeutically effective amount of an antibiotic. In some embodiments, the additional agent comprises a therapeutically effective amount of an anti-fungal agent.

In some embodiments, the infection is caused by a virus, bacteria or fungus selected from the group consisting of a coronavirus (SARS-CoV-2, MERS-CoV, and SARS-CoV), human metapneumovirus (HMPV), human parainfluenza virus (HPIV), influenza (Flu), respiratory syncytial virus (RSV), a rhinovirus (RV-A, RV-B, or RV C), an adenovirus, *Haemophilus influenzae*, measles virus, varicella-zoster virus, *Legionella* (Legionnaires' Disease), *Mycoplasma pneumoniae, Streptococcus pneumoniae* (or pneumococcus, Pneumococcal disease), *Pneumocystis jirovecii* (*Pneumocystis* pneumonia), *Bordetella pertussis* (whooping cough), *Chlamydia pneumoniae, Chlamydia psittaci* (psittacosis), *Blastomyces dermatitidis* (Blastomycosis), *Cryptococcus gattii, Paracoccidioides brasiliensis* (Paracoccidioidomycosis), *Coccidioides immitis* (Coccidioidomycosis), *Coccidioides posadasii* (Coccidioidomycosis), and *Histoplasma capsulatum* (Histoplasmosis).

In some embodiments, the method comprises administering an IV loading dose of the A2A agonist, wherein the loading dose is from 0.01-100 µg/kg/h over 30 minutes; and administering a maintenance dose of the A2A agonist, wherein the maintenance dose is from 0.001-10 µg/kg/h for 6-48 hours.

In some embodiments, the loading dose is administered as a bolus IV injection. In some embodiments, the maintenance dose is administered for 1-48 h. In some embodiments, the maintenance dose is from 0.001-10 µg/kg body weight/h and administered for 0-48 h.

In some embodiments, the A2A agonist is regadenoson, which is intravenously administered as a bolus at a loading dose of 1-10 µg/kg/h for 30 min and a maintenance dose of from 1-10 ug/kg/h for 3-48 h.

In some embodiments, the A2A agonist is regadenoson which intravenously administered as a dose of 0.5-5 µg/kg/h for 30 minutes.

In some embodiments, the A2A agonist is ATL146e, which is intravenously administered as a loading dose of from 0.5-5 µg/kg/h for 30 min and a maintenance dose of from 1-10 µg/kg/h for 3-48 h.

In some embodiments, the A2A agonist is ATL146e, which is intravenously administered as dose of 0.5-10 ug/kg/h over 30 minutes.

In some embodiments, the A2A receptor stimulator is an orthosteric activator of the adenosine A2A receptor.

In another aspect, the invention provides a method of treating a COVID-19 patient with inflamed lungs. In particular embodiments, A2A receptor agonists reduce or prevent a cytokine storm in COVID-19 patients, and thereby reduce risk of death. In some embodiments, the COVID-19 patient is receiving oxygen.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

FIG. 3. Weight loss (A) and clinical scores (B) of SARS CoV-2 infected mice treated with apadenoson (drug with delay) or saline (vehicle) were not statistically different on day five post-infection. Mean±SD is shown. Statistically evaluated using unpaired t-test.

FIG. 14. Dynamic changes of blood pressure prior, during and post regadenoson infusion in lung transplant recipients. The subjects were infused with regadenoson at the flowing doses for 12 hours. Initial dose, 0.24 ug/kg/hr; lower dose, 0.60 ug/kg/hr; low dose, 1.44 ug/kg/hr; high dose, 2.88 ug/kg/hr. The systolic (A) and diastolic (B) blood pressure A were monitored and recorded at the indicated timepoints from start of the drug infusion. Data shown are the mean±SD. P>0.05.

FIG. 15. Dynamic changes of heart beats (A) and mean arterial pressure (B) prior, during and post regadenoson infusion in lung transplant recipients. The subjects were infused with regadenoson at the flowing doses for 12 hours. Initial dose, 0.24 ug/kg/hr; lower dose, 0.60 ug/kg/hr; low dose, 1.44 ug/kg/hr; high dose, 2.88 ug/kg/hr. The heart beats and mean arterial pressure were monitored and recorded at the indicated timepoints (prior, during and post) of drug infusion. Data shown are the mean±SD. P>0.05.

FIG. 16. Changes of plasma levels of TNF-α and IL-10 prior and during regadenoson infusion in lung transplant recipients. Bar graphs show the plasma levels of TNF-a (A) and IL-10 (B) at the following indicated timepoints. T1, prior infusion (baseline); T2, 15 minutes before reperfusion of the 1st lung; T3, 30 minutes after reperfusion of 1st lung; T4, 30 minutes after reperfusion of 2nd lung; TS, 6 hours after reperfusion of 1st lung. Low dose, 1.44 ug/kg/hour, n=14; High dose, 2.88 ug/kg/hour, n=3; and Control, control lung transplant patients, n=7. Data shown are the mean±SD. *p<0.1.

FIG. 19. Changes of plasma levels of IL-6 and IL-8 prior and during regadenoson infusion in lung transplant recipients. Bar graphs show the plasma levels of IL-6 (A) and IL-8 (8) at the following indicated timepoints. T1, prior infusion (baseline); T2, 15 minutes before reperfusion of the 1st lung; T3, 30 minutes after reperfusion of 1st lung; T4, 30 minutes after reperfusion of 2nd lung; T5, 6 hours after reperfusion of 1st lung. Low dose, 1.44 ug/kg/hour, n=14; High dose, 2.88 ug/kg/hour, n=3; and Control, control lung transplant patients, n=7. Data shown are the mean±SD. *, P<0.05; **P<0.01.

FIG. 23. Median fluorescence intensity (MFI) of $A_{2A}R$ on peripheral blood mononuclear cells in the low dose regadenoson treated lung transplantation patients. (A) Flow cytometry gating strategy used to identify CD3+6B11+ invariant natural killer T (iNKT)cells, B lymphocytes and conventional T lymphocytes (Cony T). (B) Flow cytometry gating strategy used to identify subsets of monocytes and dendritic cells. CM: classical monocytes; IM: intermediate monocytes; NCM: Non-classical monocytes cells; mDC: myeloid dendritic cells; pDC: Plasmacytoid dendritic cells. (C) MFI of $A_{2A}R$ on peripheral blood mononuclear cells in the low dose regadenoson treated lung transplantation patients. The samples used in the flow cytometry assay are collected at the same timepoints (T1-TS) as indicated in FIGS. 21 and 22. The PBMCs were isolated and stained with panels of antibodies. The median fluorescence intensity of $A_{2A}R$ was analyzed with FCS Express 7 and GraphPad Prism 9.0. Data shown are the mean±S.D. n=7.

FIG. 25. $A_{2A}R$ agonists suppress LPS induced-MMP-9 expression and cell-bound RAGE shedding in alveolar macrophage (MHS). (A) Gelatin zymography images of LPS stimulating MMP-9, but not MMP-2 in the MHS cell conditional media. The MHS cells are treated with LPS (75 ng/ml), GM6001 (2 nM) with/without regadenoson (100 nM) and apadenoson (10 nM) for 6 hours. (B) Immunofluorescence staining of RAGE on MHS cells treated with LPS, GM6001 and regadenoson and apadenoson. Green indicates positive RAGE staining signals. Cells were counter-stained with DAPI to reveal nuclei (Blue). Photographs were taken under a Leica microscope with 600× magnification. LPS: Lipopolysaccharides, GM: MMP inhibitor GM6001, Reg: Regadenoson, Apa: Apadenoson (ATL-146e).

FIG. 26. MMP-9 cleave cell-bound RAGE into sRAGE in monocytes/macrophages (Raw). (A) Gelatin zymography images of PMA stimulates MMP-9, but not MMP-2 in the Raw cell conditional media. The Raw cells are treated with PMA (20 nM), GM6001 (2 nM) and Regadenoson (100 nM) for 24 hours. (B) Immunofluorescence staining of RAGE on Raw cells treated with PMA, GM6001 and Regadenoson. Green indicates positive RAGE staining signals. Cells were counter-stained with DAPI to reveal nuclei (Blue). Photographs were taken under a Leica microscope with ×600 magnification. PMA: Phorbol 12-myristate 13-acetate. GM: MMP inhibitor GM6001. Reg: Regadenoson.

FIG. 31. Histology Day 7—Apadenoson ATL146e 125, 000 PFU intra-tracheal.

FIG. 35. Histology Day 7—Regadenoson 125,000 PFU intra-tracheal.

DETAILED DESCRIPTION OF THE INVENTION

Figure 1:
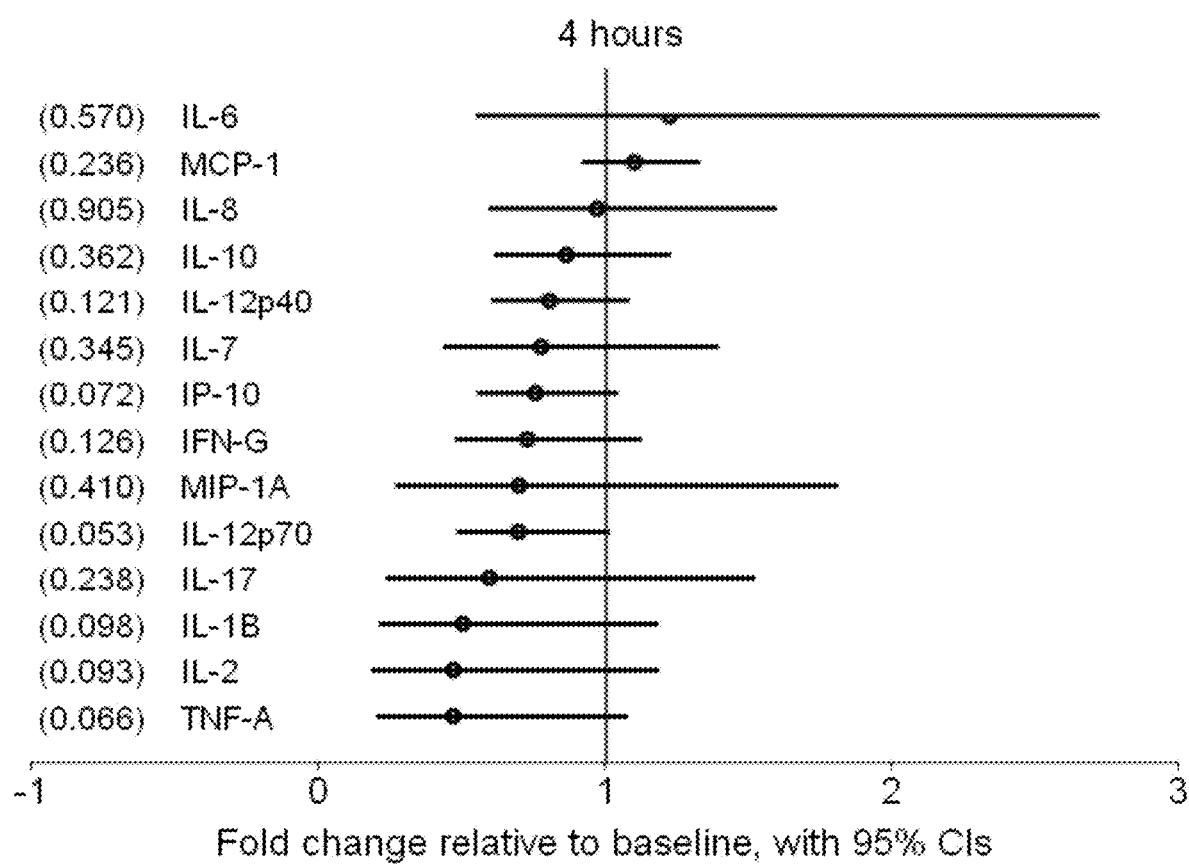
FIG. 1. Changes of plasma levels of cytokines in regadenoson-treated COVID-19 Patients. Changes in cytokine levels following 4 hours of drug infusion were analyzed using a repeated measures model with a spatial power covariance structure. Data were analyzed after transforming to the log scale to facilitate interpretation as fold changes relative to baseline. Contrasts, along with 95% confidence intervals were used to estimate changes from baseline. Analyses were carried out in SAS 9.5 PROC MIXED. (n=5). P values are listed on the left of each measured cytokines.

The invention is based on the discovery that A2A receptor activation inhibits cytokine storm in COVID-19 patients. Several selective A2A receptor agonists have been developed, including regadenoson, which is approved as a coronary vasodilator for myocardial perfusion imaging. It is shown herein that infusion of regadenoson into 5 COVID-19 patients produces rapid subjective symptom improvement; increased SpO2; reduced D-dimer; a downward trend in CRP; reduced activation (% CD69+) of circulating iNKT cells: and a gradual reduction in 11 of 13 pro-inflammatory cytokines measured in plasma. Regadenoson administered in Alzet pumps also increases survival of K18-ACE2 mice infected with SARS-CoV-2.

The data provides that regadenoson and other A2A receptor agonists can be used to treat cytokine storm syndrome in COVID-19 patients and other infections.

Reference will now be made in detail to embodiments of the invention which, together with the drawings and the following examples, serve to explain the principles of the invention. These embodiments describe the invention in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one" and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

It is contemplated that any method or composition described herein can be implemented with respect to any other method or composition described herein.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005)), for example.

A "patient" can refer to warm blooded mammals that are typically under medical care (e.g., humans and domesticated animals). Non-limiting examples include feline, canine, equine, bovine, non-human primates, and humans. Subject and patient are used interchangeably herein. In some embodiments, the patient is infected with a coronavirus, such as SARS-CoV-2. In some embodiments, the patient is undergoing supplemental oxygen administration.

"Treating" or "treatment" covers the treatment of a disease-state or condition in a mammal, and includes: (a) preventing the disease-state or condition from occurring in a mammal, in particular, when such mammal is predisposed to the disease-state or condition but has not yet been diagnosed as having it; (b) inhibiting the disease-state or condition, e.g., arresting its development; and/or (c) relieving the disease state or condition, e.g., causing regression of the disease-state or condition until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic alts or the quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic subacetic, succinic, sulfamic, sulfanilic, sulfuric, tannic, tartaric, and toluenesulfonic.

The pharmaceutically acceptable salts of the compounds that can be used in the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences,* 18th ed., Mack Publishing Company, Easton PA, 1990, p 1445, the disclosure of which is hereby incorporated by reference.

"Therapeutically effective amount" includes an amount of a compound of the present invention that is effective when administered alone or in combination to an indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components. Those of skill in the art understand that the effective amount may improve the patient's or subject's condition but may not be a complete cure of the disease and/or condition. The "effective amount" can correspond to an amount administered to subjects or to cells directly.

In one embodiment, the invention provides a method of treating cytokine storm syndrome comprising administering to a patient in need thereof a therapeutically effective amount of an adenosine A2A receptor agonist.

Cytokine storm syndrome is a life-threatening condition caused by a subject's reaction to infection. While the release of cytokines by various immune cells is needed to mobilize the immune system to fight infection, the excessive production of cytokines in cytokine storm can produce too much inflammation and can kill the inflamed subject due to severe hypotension, pulmonary failure, and/or multi-organ failure. Cytokine storm is sometimes also referred to cytokine-associated toxicity or cytokine release syndrome (CRS). Blood serum consists of many proteins including antibodies, cytokines, hormones, etc. with different molecular weights and dielectric properties.

The treatment reduces or inhibits one or more inflammatory cytokines associated with cytokine storm syndrome. The terms "decreased," "decrease," "reduced," "reduction," or "inhibit" are all used herein to mean a decrease by a statistically significant amount. In some embodiments, "decreased," "decrease," "reduced," "reduction," or "inhibit" typically mean a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. Where applicable, a decrease can be down to a level accepted as within the range of normal for an individual without a given disease or condition, or sufficient to alleviate one or more symptoms of the disease or condition.

Exemplary cytokines that may be included in a cytokine storm include, but are not limited to, monocyte chemotactic protein-1 (MCP-1), interferon gamma-induced protein-10 (IP-10), interleukin (IL)-10, IL-6, IL-8, IL-1, IL-18, IL-1 receptor antagonist (IL-1Ra), tumor necrosis factor-alpha (TNF-α), chemokine (C-X-C motif) ligand 2 (CXCL2), CXCL1, CXCL13, CXCL12, chemokine (C-C motif) ligand 4 (CCL4), CCL2, intracellular adhesion molecule-1 (ICAM-1), granulocyte-colony stimulating factor (G-CSF), granulocyte-macrophage colony-stimulating factor (GM-CSF), CCL5, plasminogen activator inhibitor-1 (PAI-1), osteopontin, matrix metallopeptidase 9 (MMP9), placental growth factor-2 (PIGF-2), pentraxin 3 (PTX-3), fractalkine, angiopoietin-1, and/or insulin like growth factor binding protein 1 (IGFBP1). Particularly relevant are the blood levels of inflammatory cytokines interleukin-1 (IL-1), IL-6, IL-12, and IL-18, tumor necrosis factor alpha (TNF-α), interferon gamma (IFNγ), granulocyte-macrophage colony stimulating factor (GM-CSF) and Transforming Growth Factor (TGF).

In some embodiments, the blood level of at least one inflammatory cytokine in a patient in need of treatment is raised by more than 10%, more than 20%, more than 30% or more as compared to the corresponding blood level(s) of said cytokine(s) in a healthy subject. In some embodiments, the blood level of two or more inflammatory cytokines in a patient in need of treatment is raised by more than 10%, more than 20%, more than 30% or more as compared to the corresponding blood level(s) of said cytokine(s) in a healthy subject.

The event or agent that causes the cytokine storm is not particularly limiting. In some embodiments, the cytokine storm is caused by an infectious disease-causing agent. In some embodiments the agent is viral, bacterial, fungal, helminthic, protozoan, or a hemorrhagic infectious agent. In some embodiments the agent is a coronavirus (SARS-CoV-2, MERS-CoV, and SARS-CoV), human metapneumovirus (HMPV), human parainfluenza virus (HPIV), influenza (Flu), respiratory syncytial virus (RSV), a rhinovirus (RV-A, RV-B, or RV C), an adenovirus, *Haemophilus influenzae*, measles virus, varicella-zoster virus, *Legionella* (Legionnaires' Disease), *Mycoplasma pneumoniae*, *Streptococcus pneumoniae* (or pneumococcus, Pneumococcal disease), *Pneumocystis jirovecii* (*Pneumocystis* pneumonia), *Bordetella pertussis* (whooping cough), *Chlamydia pneumoniae*, *Chlamydia psittaci* (psittacosis), *Blastomyces dermatitidis* (Blastomycosis), *Cryptococcus gattii*, *Paracoccidioides brasiliensis* (Paracoccidioidomycosis), *Coccidioides immitis* (Coccidioidomycosis), *Coccidioides* posadasii (Coccidioidomycosis), and *Histoplasma capsulatum* (Histoplasmosis).

In some embodiments, the infectious disease is selected from at least one of infection with an Arenaviridae, Filoviridae, Bunyaviridae, Flaviviridae, and Rhabdoviridae virus. In some embodiments, the one or more infectious diseases is selected from at least one of Ebola, Marburg, Crimean-Congo hemorrhagic fever (CCHF), South American hemorrhagic fever, dengue, yellow fever, Rift Valley fever, Omsk hemorrhagic fever virus, Kyasanur Forest, Junin, Machupo, Sabia, Guanarito, Garissa, Ilesha, or Lassa fever viruses.

COVID-19, the disease caused by SARS-CoV-2 infection, sometimes manifests as a life-threatening cytokine storm with lung hyperinflammation. In some embodiments, the A2A agonists are useful for the treatment of patients with virally-induced (specifically SARS-CoV-2-induced) lung hyperinflammation. In some embodiments, the lethality of COVID-19 is associated with pulmonary cytokine storm. COVID-19 infection may result in a mortality rate of 2-4% compared with a mortality rate usually less than 0.2% from influenza. Accumulating evidence suggests that a critically ill subgroup of patients with COVID-19 have cytokine storm syndrome. Acute respiratory distress syndrome (ARDS) is the leading cause of death. In mammals, JAK/STAT is the principal signaling pathway used by pro-inflammatory cytokines and growth factors. The cytokine release profile is associated with the severity of COVID-19 symptoms, and characterized by increased JAK/STAT signaling with increased interleukin (IL)-2, IL-6, IL-7, granulocyte-colony stimulating factor (GMCSF), interferon-γ inducible protein 10 (IP-10), monocyte chemoattractant protein 1 (MCP-1), macrophage inflammatory protein 1-alpha (MIP-1a), and tumor necrosis factor-alpha (TNF-α). Predictors of lethality from a multicenter study of 150 confirmed COVID-19 cases in Wuhan, China, included elevated IL-6 ($p<0.0001$), consistent with the idea that mortality might be due to virally driven hyperinflammation.

In some embodiments, the patient to be treated is a COVID-19 patient. In some embodiments, candidates for treatment are COVID+ and have a severe infection defined by hospitalization for hypoxia and treatment with supplemental oxygen, a ventilator or by Extracorporeal Membrane Oxygenation (ECMO). Markers of a severe inflammatory response can include increases in WBC count, fever, and chest radiograph findings of infiltrates. In some embodiments, such patients are administered an A2A agonist. In some embodiments, the intervention reduces death or multi-organ failure. In some embodiments, the causative SARS-CoV-2 pathogen is not necessarily limiting. In some embodiments, the SARS-CoV-2 is a variant selected from Alpha (B.1.1.7 and Q lineages), Beta (B.1.351 and descendent lineages), Gamma (P.1 and descendent lineages), Epsilon (B.1.427 and B.1.429), Eta (B.1.525), Iota (B.1.526), Kappa (B.1.617.1), 1.617.3, Mu (B.1.621, B.1.621.1), Zeta (P.2), Delta (B.1.617.2 and AY lineages), Omicron (B.1.1.529 and BA lineages), and combinations thereof.

Cytokine storm may also be caused by conditions resulting in damage or insult to the body including, e.g., a physical, chemical, or biological damage or insult, as well as non-infectious disease processes, including cancer and non-cancer-related disease processes. Accordingly, such surges can be caused by trauma, injury, burn, exposure to toxic materials (e.g., bacterial toxins, mycotoxins (e.g., aflatoxin B1), toxic chemicals, carcinogens (for example, alcohol (e.g., ethanol), n-nitrosodimethylamine (NDMA) and other nitrosamines, aldehydes, cyclosporine, asbestos, arsenic, benzene, cyclophosphamide, tamoxifen, and vinyl chloride)), acute respiratory distress syndrome secondary to drug use or inhalation of toxins, acute pancreatitis or hepatitis (due to, e.g., chronic alcohol exposure), fulminant hepatic failure, multiple sclerosis, rheumatic diseases (e.g., systemic juvenile idiopathic arthritis (JIA) and adult-onset Still's disease (AOSD)), and Langerhans cell histiocytosis (LCH).

In addition to the above, cytokine storm may be caused by treatment of an underlying disease or condition, rather than (or in addition to) the disease or condition itself. Examples of such treatments include surgery (e.g., cardiac bypass surgery), immunotherapy, chemotherapy, radiation, and cell or tissue-based therapies (e.g., bone marrow or stem cell transplantation (e.g., allogeneic hematopoietic stem-cell transplantation), which may lead to graft-versus host disease, and T-cell therapy, including CAR-T cell therapy). Specific, non-limiting examples of immunotherapy include treatment with therapeutic antibodies (e.g., rituximab, anti-CD28 antibody theralizumab/TGN1412, anti-PD1 antibodies, anti-PDL1 antibodies, and anti-CTLA antibodies), CAR-T cells (e.g., CAR-T cells directed against CD19 or other markers of hematopoietic malignancies), cytokines (e.g., IL-2), and vaccination. Examples of chemotherapy include platinum-based agents (e.g., cisplatin, carboplatin, oxaliplatin, and nedaplatin), taxane-based agents (e.g., paclitaxel and docetaxel), nitrogen mustards (e.g., mechlorethamine, cyclophosphamide, melphalan, chlorambucil, ifosfamide, and busulfan), nitrosoureas (e.g., N-nitroso-N-methylurea (MNU), carmustine (BCNU), lomustine (CCNU), semustine (MeCCNU), fotemustine, streptozotocin), tetrazines (e.g., dacarbazine, mitozolomide, temozolomide), and aziridines (e.g., thiotepa, mytomycin and diaziquone (AZQ)), anti-folates (e.g., methotrexate and pemetrexed), fluoropyrimidines (e.g., fluorouracil and capecitabine), deoxynucleotisde analogues (e.g., cytarabine, gemcitabine, decitabine, azacitidine, fludarabine, nelarabine, cladribine, clofarabine, and pentostatin), thiopurines (e.g., thioguanine, and mercaptopurine), vinca alkaloids (e.g., vincristine, vinblastine vinorelbine, vindesine, and vinflunine), topoisomerase inhibitors (e.g., etoposide, teniposide, irinotecan, doxorubicin, topotecan, mitoxantrone, novobiocin, merbarone, and aclarubicin), and cytotoxic antibiotics (e.g., doxorubicin, daunorubicin, epirubicin, idarubicin, pirarubicin, aclarubicin, mitoxantrone, mitomycin C, mitoxantrone, and actinomycin).

In some embodiments, effective therapy (treatment) of the cytokine storm will be manifest as an improvement in pulmonary function reflected by decreases in oxygen requirement or decreased need for ventilatory support or ECMO (Extracorporeal membrane oxygenation). The ECMO machine is like the heart-lung by-pass machine used in open-heart surgery. It pumps and oxygenates a patient's blood outside the body, allowing the heart and lungs to rest. Radiographic improvement of the 1w1g can also be evaluated, as well as vital signs (temperature, blood pressure, and pulse oximetry).

As provided herein, subjects are administered a therapeutically effective amount of an adenosine A2A receptor agonist. Without being bound by theory, agonists (activators) of adenosine A2A receptors (A2A agonists) can inhibit the release of pro-inflammatory cytokines from immune cells and reduce death due to sepsis in mammals (see FIGS. 2A-B).

In some embodiments, the A2A agonists may also reduce blood pressure and pulmonary edema to improve the function of the inflamed lung. In some embodiments, the A2A agonist treatment will decrease pulmonary cytokine storm evoked by viruses, bacteria, or fungi, reduce lung inflammation, and sometimes reduce blood pressure. In some embodiments, these actions enhance pulmonary function and reduce death in the patient.

The adenosine A2A receptor agonist that can be administered is not particularly limiting. In some embodiments, the agonist is selected from the group consisting of regadenoson, ATL-146e (apadenoson), ATL-146a, ATL-193, ATL-2037, binodenoson, ATL-313, ATL-1222, ATL1223, IBMECA, Cl-IB-MECA, WRC0470, 2-hexynyl-NECA, adenosine, compound 4g [PMID 22220592; 6-(2,6-Dimethylpyridin-4-Y1)-5-Phenyl-1,2,4-Triazin-3-Amine], NECA, UK-431,097, CGS-21680, GR79236, indirubin-3'-monoxime, and 2-propynyl adenosine analogs having A2A agonist activity as described in U.S. Patent Appl. Pub. No. 2003/186926 (see also patent WO 2003/029264), which is incorporated by reference herein, or a pharmaceutically acceptable salt of the above mentioned compounds. A2A agonism can be produced by elevating endogenous adenosine, either with low does methytrexate (7.5-25 mg weekly), which stimulates the translocation of adenine nucleotides from inside to outside cells where they are metabolized into adenosine, or by inhibiting the equilibrative nucleoside transporter with dipyridamole or other nucleoside transport inhibitors.

Regadenoson has been approved for use to dilate coronary arteries as a pharmacological stress agent. For that use, regadenoson solution is formulated into vials and delivered as a rapid IV bolus that is administered within 30 seconds to achieve coronary vasodilation. The amount of regadenoson administered for pharmacological stress imaging is 400 µg (1 vial). Rapid IV bolus injection is not required for use of regadenoson or other A2A agonists as anti-inflammatory agents.

In some embodiments, ligands that bind to the adenosine binding site on adenosine A2A receptors (aka the orthosteric site) can be identified based on their ability to compete for radioligands such as the agonist [$^3$H]CGS-21680 or the antagonist $^{125}$I-ZM-241385. In some embodiments, $A_{2A}$ agonists described herein can be identified as compounds that compete for radioligand binding and stimulate biological responses that are inhibited by $A_{2A}$ antagonists in tissues or cells. In some embodiments, $A_{2A}$ agonists cause dilation of coronary arteries, inhibition of oxidative burst in neutrophils, inhibition of cytokine release from macrophages and dendritic cells (e.g. TNF-α) and elevation of cyclic AMP accumulation in HEK293 cells genetically engineered to express recombinant $A_{2A}$ receptors or in various mammalian immune cells including neutrophils, iNKT cells previously activated by alpha-GalCer or macrophages previously activated by endotoxin.

Formulations and Dosages

In some embodiments, pharmaceutical compositions of the present invention comprise an effective amount of one or more drugs, dissolved or dispersed in a pharmaceutically acceptable carrier.

The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one A2A agonist or additional active ingredient will be known to those of skill in the art in light of the present disclosure. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The compounds of the present invention can be formulated as pharmaceutical compositions and administered to a mammalian host, such as a human patient in a variety of forms adapted to the chosen route of administration, e.g., orally or parenterally, by intravenous (e.g., continuously or bolus), intrathecal, intramuscular, topical, intradermal, transdermally, intraperitoneal, intraocular, inhalation (aerosol) or subcutaneous routes. In some embodiments, the active agents are administered via a pump, such as an osmotic pump or an IV infusion pump.

As provided herein, the patient is administered a therapeutically effective amount of the A2A receptor agonist. In some embodiments, the agonist is administered periodically or continuously over a period of time in order to achieve effective and steady therapeutic levels. In some embodiments, the agonist is administered as a single dose. In some embodiments, the agonist is administered as an infusion. In some embodiments, the compound(s) or composition(s) can be administered to the subject once, such as by a single injection or deposition at or near the site of interest. In some embodiments, the compound(s) or composition(s) can be administered to a subject over a period of hours, days, weeks, or months. In some embodiments, the compound(s) or composition(s) is administered at least once a day to a subject. Where a dosage regimen comprises multiple administrations, it is understood that the effective amount of the compound(s) or composition(s) administered to the subject can comprise the total amount of the compound(s) or composition(s) administered over the entire dosage regimen.

In some embodiments, an effective amount of the A2A agonist that is administered includes a dose of about 0.0001 nM to about 2000 µM. In some embodiments, amount administered is from about 0.01 nM to about 2000 µM; about 0.01 µM to about 0.05 µM; about 0.05 µM to about 1.0 04; about 1.0 µM to about 1.5 µM; about 1.5 µM to about 2.0 µM; about 2.0 µM to about 3.0 µM; about 3.0 µM to about 4.0 µM; about 4.0 µM to about 5.0 µM; about 5.0 µM to about 10 µM; about 10 µM to about 50 µM; about 50 µM to about 100 µM; about 100 µM to about 200 µM; about 200 µM to about 300 µM; about 300 µM to about 500 µM; about 500 µM to about 1000 µM; about 1000 µM to about 1500 µM; and about 1500 µM to about 2000 µM. Of course, all of these amounts are exemplary, and any amount in-between these points is also expected to be of use in the invention.

In some embodiments, from about 0.1-1000 µg/h of the agonist is administered by infusion, e.g., intravenously. In some embodiments, the agonist is administered over a period of from 1-48 h, or longer, e.g., depending on the severity of the condition of the patient.

In some embodiments, the subject is first administered a loading dose, followed by administration of a maintenance dose over a period of time. In some embodiments, the administration comprises first administering a loading dose of the A2A agonist, wherein the loading dose is from 1-600 µg; and then administering a maintenance dose of the A2A agonist, wherein the maintenance dose is from 0.1-1000 µg/kg body weight/h. In some embodiments, the maintenance dose is administered continuously (e.g., via infusion).

In some embodiments, the loading dose is about 1 µg, 2 µg, 3 µg, 4 µg, 5 µg, 6 µg, 7 µg, 8 µg, 9 µg, 10 µg, 20 µg, 30 µg, 40 µg, 50 µg, 60 µg, 70 µg, 80 µg, 90 µg, 100 µg, 120 µg, 140 µg, 160 µg, 180 µg, 200 µg, 220 µg, 240 µg, 260 µg, 280 µg, 300 µg, 320 µg, 340 µg, 360 µg, 380 µg, 400 µg, 420 µg, 440 µg, 460 µg, 480 µg, 500 µg, 520 µg, 540 µg, 560 µg, 580 µg or 600 µg. In some embodiments, from about 10-500 µg, 10-100 µg, 100-500 µg, 200-400 µg, 200-600 µg, or 300-600 µg is administered.

In some embodiments, the maintenance dose is from 0.1 µg/h, 0.2 µg/h, 0.3 µg/h, 0.4 µg/h, 0.5 µg/h, 0.6 µg/h, 0.7 µg/h, 0.8 µg/h, 0.9 µg/h, 1.0 µg/h, 2 µg/h, 3 µg/h, 4 µg/h, 5 µg/h, 6 µg/h, 7 µg/h, 8 µg/h, 9 µg/h, 10 µg/h, 20 µg/h, 30 µg/h, 40 µg/h, 50 µg/h, 60 µg/h, 70 µg/h, 80 µg/h, 90 µg/h, 100 µg/h, 120 µg/h, 140 µg/h, 160 µg/h, 180 µg/h, 200 µg/h, 220 µg/h, 240 µg/h 260 µg/h, 280 µg/h, 300 µg/h, 320 µg/h, 340 µg/h, 360 µg/h, 380 µg/h, 400 µg/h, 420 µg/h, 440 µg/h, 460 µg/h, 480 µg/h, 500 µg/h, 520 µg/h, 540 µg/h, 560 µg/h, 580 µg/h, 600 µg/h, 620 µg/h, 640 µg/h, 660 µg/h, 680 µg/h, 700 µg/h, 720 µg/h, 740 µg/h, 760 µg/h, 780 µg/h, 800 µg/h, 820 µg/h, 840 µg/h, 860 µg/h, 880 µg/h, 900 µg/h, 920 µg/h, 940 µg/h, 960 µg/h, 980 µg/h, to 1000 µg/h. In some embodiments, from 1-500 µg/h, 10-100 µg/h, 100-500 µg/h, 50-200 µg/h, and 200-400 µg/h is administered.

In some embodiments, the maintenance dose is from 0.01-100 µg/kg/h. In some embodiments, the maintenance dose is from m 0.01 µg/kg/h, 0.02 µg/kg/h, 0.03 µg/kg/h, 0.04 µg/kg/h, 0.05 µg/kg/h, 0.06 µg/kg/h, 0.07 µg/kg/h, 0.08 µg/kg/h, 0.09 µg/kg/h, 0.1 µg/kg/h, 0.2 µg/kg/h, 0.3 µg/kg/h, 0.4 µg/kg/h, 0.5 µg/kg/h, 0.6 µg/kg/h, 0.7 µg/kg/h, 0.8 µg/kg/h, 0.9 µg/kg/h, 1.0 µg/kg/h, 2 µg/kg/h, 3 µg/kg/h, 4 µg/kg/h, 5 µg/kg/h, 6 µg/kg/h, 7 µg/kg/h, 8 µg/kg/h, 9 µg/kg/h, 10 µg/kg/h, 20 µg/kg/h, 30 µg/kg/h, 40 µg/kg/h, 50 µg/kg/h, 60 µg/kg/h, 70 µg/kg/h, 80 µg/kg/h, 90 µg/kg/h, to 100 µg/kg/h. In some embodiments, the maintenance dose is from 0.1-100 µg/kg/h, 0.1-50 µg/kg/h, 1-100 µg/kg/h, and 10-100 µg/kg/h.

In some embodiments, the loading dose is administered as a bolus. In some embodiments, the maintenance dose is delivered for 1, 2, 3, 4, 5, 6, 7, 8, 9, 10, 11, 12, 13, 14, 15, 16, 17, 18, 19, 20, 21, 22, 23, 24, 25, 26, 27, 28, 29, to 30 minutes.

In some embodiments, the maintenance dose is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, to 48 h. In some embodiments, the maintenance dose is administered from 1-24 h, 2-48 h, 3-48 h, 6-48 h, 24-48 h, and 36-48h.

In some embodiments, the A2A agonist is regadenoson, and is intravenously administered as a bolus as a loading dose of from 100-500 µg and a maintenance dose of from 0.1-10 µg/kg body weight/h for 1-48 h. In some embodiments, regadenoson is intravenously administered as a bolus at a loading dose of from 200-600 µg over 30 minutes and a maintenance dose of from 1-50 µg/kg/h for 1-48 h. In some embodiments, regadenoson is administered from 3-48 h or from 6-48 h.

In some embodiments, the A2A agonist is ATL146e, and is intravenously administered as a bolus loading dose of from 100-500 µg over 30 minutes and a maintenance dose of from 0.1-10 µg/kg/h for 1-48 h. In some embodiments, ATL146e is intravenously administered as a rapid infusion at a loading dose of from 200-600 µg over 30 min and a maintenance dose of from 0.1-100 µg/kg/h for 1-48 h. In some embodiments, the maintenance dose is initiated within 1 minute after the loading dose has been administered. In some embodiments only a loading dose without a maintenance dose is administered. In some embodiments, the maintenance dose is administered from 3-48 h or 6-48 h.

The agonists can be formulated as pharmaceutical compositions having a pharmaceutically acceptable carrier. Exemplary pharmaceutical excipients and carriers are disclosed in "Remington: The Science and Practice of Pharmacy," A. Gennaro, ed., 20th edition, Lippincott, Williams & Wilkins, Philadelphia, PA In some embodiments, the agonists can be systemically administered, e.g., orally, in combination with a pharmaceutically acceptable carrier/excipient such as an inert diluent or an assimilable edible canier. In some embodiments, they may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules elixirs, suspensions, syrups, wafers, and the like. The amount of active compound in such therapeutically useful compositions is such that an effective dosage level will be obtained.

The amount of the compound of the present invention or an active salt or derivative thereof, required for use in treatment will vary not only with the particular compound or salt selected but also with the route of administration, the nature of the condition being treated, and the age and condition of the patient, and will ultimately be at the discretion of the attendant physician or clinician. In general, however, a suitable dose will be in the range of (a) about 0.001-1000 mg/kg of body weight per day, (b) about 0.01-500 mg/kg of body weight per day, and (c) about 1-20 mg/kg of body weight per day.

For oral administration, the compounds of the present invention may be administered to an adult once or divided into several times at a dose of generally from 0.001 to 5000 mg per day, also from 0.1 to 2500 mg per day, and from 1 to 1000 mg per day. For a liquid composition (e.g., in a lotion), the concentration of compounds of the present invention can be from (a) about 0.1-25 wt % and (b) about 0.5-10 wt %. The concentration in a semi-solid or solid composition such as a gel or a powder can be (a) about 0.1-5 wt % and (b) about 0.5-2.5 wt %.

The compounds of the present invention can be conveniently administered in unit dosage form; e.g., tablets, caplets, etc., containing (a) about 4-400 mg, (b) about 10-200 mg, and (c) about 20-100 mg of active ingredient per unit dosage form.

The compounds of the present invention can be administered to achieve peak plasma concentrations of the active compound of (a) about 0.02-20 µM, (b) about 0.1-10 µM, and (c) about 0.5-5 µM. These concentrations may be achieved, for example, by the intravenous injection (e.g., continuously or bolus) of a 0.005-0.5% solution of the active ingredient, or orally administered as a bolus containing about 4-400 mg of the active ingredient.

When a compound of the present invention is administered in combination with another agent or agents (e.g., co-administered), then the compound of the present invention and other agent can be administered simultaneously or in any order. They can be administered as a single pharmaceutical composition or as separate compositions. The administration of the compound of the present invention can be prior to the other agent(s), within minutes thereof, or up to hours (e.g. 24 or 48) or even days after the administration of the other agent(s). For example, the administration of the compound of the present invention can be within about 24 hours or within about 12 hours.

The tablets, troches, pills, capsules, and the like may also contain the following: binders such as gum tragacanth, acacia, corn starch or gelatin; excipients such as dicalcium phosphate; a disintegrating agent such as com starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid canier, such as a vegetable oil or a polyethylene glycol. Various other materials may be present as coatings or to otherwise modify the physical form of the solid unit dosage form. For instance, tablets, pills or capsules may be coated with gelatin wax, shellac or sugar and the like. A syrup or elixir may contain the active compound, sucrose or fructose as a sweetening agent, methyl and propylparabens as preservatives, a dye and flavoring such as cherry or orange flavor. Of course any material used in preparing any unit dosage form should be pharmaceutically acceptable and substantially non-toxic in the amounts employed. In addition, the active compound may be incorporated into sustained release preparations and devices.

The compounds of the present invention may also be administered intravenously (e.g., continuously or bolus) or intraperitoneally by infusion or injection. Solutions of the compounds of the present invention or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained for example, by the formation of liposomes or micelles, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugar, buffers or sodium chloride.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Prolonged absorption of the injectable compositions can be brought about by the use in the compositions of agents delaying absorption, for example, aluminum monostearate and gelatin. Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds of the present invention may be applied in pure form, e.g., when they are liquids. However, it will generally be desirable to administer them to the skin as compositions or formulations, in combination with a dermatologically acceptable carrier which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants.

Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the present invention can be determined by comparing their in vitro activity and in vivo activity in animal model. Methods for the extrapolation of effective dosages in mice, and other animals, to humans are known to the art; for example, see U.S. Pat. No. 4,938,949.

The compounds of the present invention can also be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, and atomizers are fully described in pharmaceutical reference books such as Remington's Pharmaceutical Sciences Volumes 16 (1980) or 18 (1990) Mack Publishing Co.

The desired dose of the compounds of the present invention may conveniently be presented in a single dose or as divided doses administered at appropriate intervals, for example, as two, three, four or more sub-doses per day. The sub-dose itself may be further divided, e.g., into several discrete loosely spaced administrations, such as multiple inhalations from an insufflator or by application of a plurality of drops into the eye.

The treatments may include various "unit doses." Unit dose is defined as containing a predetermined quantity of the therapeutic composition (an A2A agonist) calculated to produce the desired responses in association with its administration, e.g., the appropriate route and treatment regimen. The quantity to be administered, and the particular route and formulation, are within the skill of those in the clinical arts. Also of importance is the subject to be treated, in particular, the state of the subject and the protection desired. A unit dose need not be administered as a single injection but may comprise continuous infusion over a set period of time.

Combination Therapy

The active agents of the present invention can be administered alone or in combination with one or more additional active pharmaceutical agents.

In some embodiments, the active agents of the invention are administered with one or more additional active pharmaceutical agents that are useful to treat conditions associated with infection, such as a coronavirus infection.

In some embodiments, the additional active agent can include an agent useful to treat a lung disease or inflammatory condition.

In some embodiments, such additional pharmaceutical agents can include one or more corticosteroids, exogenous surfactants, statins, beta-blockers, n-acetylcysteine, anti-inflammatory agents, immunosuppressants, therapeutic antibodies, antibiotics, antifungal or antiviral agents.

In some embodiments, the methods may further include administering an effective amount of an additional active ingredient selected from effective amounts of a steroid, glucocorticoid or other anti-inflammatory corticosteroid. Suitable steroids include 21-acetoxypregnenolone, alclometasone, algestone, anacortave acetate, amcinonide, beclomethasone, betamethasone, budesonide, chloroprednisone, clobetasol, clobetasone, clocortolone, cloprednol, cortieosterone, cortisone, cortivazol, deflazacort, desonide, desoximetasone, diflorasone, diflucortolone, difuprednate, enoxolone, fluazacort, flucloronide, flumethasone, flunisolide, fluocinolone acetonide, fluocinonide, flucloronide, flumethasone, flunisolide, fluocortin butyl, fluocortolone, fluorometholone, fluperolone acetate, flupreduisolone, fluraudrenolide, fluticasone propionate, hydrocortamate, hydrocortisone, meprednisone, methylpreduisolone, paramethasone, prednisolone, prednisolone 21-diethylaminoacetate, fluprednidene acetate, formocortal, loteprednol etabonate, medrysone, mometasone furoate, prednicarbate, prednisolone, prednisolone 25-diethyiaminoacetate, prednisolone sodium phosphate, prednisone, prednival, prednylidene, triamcinolone, triamcinolone acetonide, triamcinolone benetonide, and triamcinolone hexacetonide, and analogs, derivatives, pharmaceutically acceptable salts, esters, prodrugs, codrugs, and protected forms thereof. Additional suitable steroids include halcinonide, halbetasol propionate, halometasone, halopredone acetate, isoflupredone, loteprednol etabonate, niazipredone, rimexoione, and tixocortol, and analogs, derivatives, pharmaceutically acceptable salts, esters, prodrugs, co-drugs, and protected forms thereof.

In various embodiments, the steroid may be administered in an effective amount of at least about 10 mg to about 1500 mg. In various embodiments, the steroid may be administered in an effective amount of at least about 10, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075 1100, 1125, 1150, 1175, 1200, 1225, 1250, 1275, 1300, 1325, 1350, 1375, 1400, 1425, 1450, 1475, and 1500 mg, or any range between any two of these amounts including from about 125 mg to about 1000 mg once daily. In some embodiments, the steroid may be administered at a dose of at least about 125 mg to about 1000 mg once daily for 3 days followed by a suitable tapering regimen as per clinical judgment.

In one embodiment, the additional pharmaceutical agent is remdesivir or an analogue thereof. In some embodiments, the additional pharmaceutical agent is a type 1 interferon, such as IFNβ1.

In some embodiments, the additional pharmaceutical agent comprises a Cas13d protein and guide RNAs-containing spacer sequences specifically complementary to the virus RNA genome. See, e.g., Nguyen et al. *Cell Research* (2020) 30:189-190, which is incorporated herein by reference.

In some embodiments, the additional agent is convalescent plasma from a patient previously infected with SARS-CoV-2.

In one embodiment, the active agent comprises chloroquine and/or hydroxychloroquine. In this embodiment, zinc and/or azithromycin (e.g., ZITHROMAX®) can optionally be administered in combination with, or in addition to, the chloroquine and/or hydroxychloroquine.

In some embodiments, the additional agent comprises HCQ (+/− azithromycin (AZT)), CQ (+/− AZT), an IL-6 receptor antagonist (e.g., Sarilumab, Siltuximab, Tocilizumab), Acetaminophen, an NSAID, an ACE inhibitor/ARB, Heparin, Ritonavir/lopinavir, Baricitinib, Bemcentinib, Bevacizumab, Colchicine, Dexamethasone, EIDD-2801, Favipiravir, Baricitinib, Bemcentinib, Bevacizumab, Fingolimod, Hydroxychloroquine and azithromycin, sulfate Ivermectin, Leronlimab, Lopinavir and ritonavir, Methylprednisolone, and Umifenovir.

In one embodiment, the active agent comprises a cathepsin L inhibitor, such as thiocarbazate SID26681509 and teicoplanin.

In one embodiment, the active agent comprises a TMPRSS2 protease inhibitor such as camostat mesylate.

In one embodiment, the additional pharmaceutical agent is one or more of the compounds disclosed by Wu et al., "Analysis of therapeutic targets for SARS-CoV-2 and discovery of potential drugs by computational methods," *Acta Pharmaceutica Sinica B* https://doi.org/10.1016/j.apsb.2020.02.008 which is incorporated by reference herein.

In some embodiments, the additional active agent is a PLpro inhibitor, such as Ribavirin Valganciclovir, β-Thymidine, Aspartame, Oxprenolol, Doxycycline, Acetophenazine, Iopromide, Riboflavin, Reprotenol, 2,2'-Cyclocytidine, Chloramphenicol, Chlorphenesin carbamate, Levodropropizine, Cefamandole, Floxuridine, Tigecycline, Pemetrexed, 1 (+)-Ascorbic acid, Glutathione, Hesperetin, Ademetionine, Masoprocol, Isotretinoin, Dantrolene, Sulfasalazine, Silybin, Nicardipine, Sildenafil, Platycodin, D, Chrysin, Neohesperidin, Baicalin, Sugetriol-3,9-diacetate, (−)-Epigallocatechin gallate, Phaitanthrin D, 2-(3,4-Dihydroxyphenyl)-2-[[2-(3,4-dihydroxyphenyl)-3,4-dihydro-5, 7-dihydroxy-2H-1-benzopyran-3-yl]oxy]-3,4-dihydro-2H-1-benzopyran-3,4,5,7-tetrol, 2,2-Di (3-indolyl)-3-indolone, (S)-(1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl-2-amino-3-phenylpropanoate, Piceatannol, Rosmarinic acid, and Magnolol.

In some embodiments, the additional active agent is a 3CLpro inhibitor, such as Lymecycline, Chlorhexidine, Alfuzosin, Cilastatin, Famotidine, Almitrine, Progabide, Nepafenac, Carvedilol, Amprenavir, Tigecycline, Demeclocycline, Montelukast, Carminic acid, Mimosine, Flavin mononucleotide, Lutein, Cefpiramide, Phenethicillin, Candoxatril, Nicardipine, Estradiol valerate, Pioglitazone, Conivaptan, Telmisartan, Doxycycline, Oxytetracycline, (1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl 5-((R)-1,2-dithiolan-3-yl) pentanoate, Betulonal, Chrysin-7-O-β-glucuronide, Andrographiside, (1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl 2-nitrobenzoate, 2β-Hydroxy-3,4-seco-friedelolactone-27-oic acid, (S)-(1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl-2-amino-3-phenylpropanoate, Isodecortinol, Cerevisterol, Hesperidin, Neohesperidin, Andrograpanin, 2-((1R,5R,6R,8aS)-6-Hydroxy-5-(hydroxymethyl)-5,8a-dimethyl-2-methylenedecahydronaphthalen-1-yl)ethyl benzoate, Cosmosiin, Cleistocaltone A, 2,2-Di(3-indolyl)-3-indolone, Biorobin, Gnidicin, Phyllaemblinol, Theaflavin 3,3'-di-O-gallate, Rosmarinic acid, Kouitchenside I, Oleanolic acid, Stigmast-5-en-3-ol, and Deacetylcentapicrin, Berchemol, In some embodiments, the additional active agent is an RNA-dependent RNA polymerase inhibitor, such as Valganciclovir, Chlorhexidine, Ceftibuten, Fenoterol, Fludarabine, Itraconazole, Cefuroxime, Atovaquone, Chenodeoxycholic acid, Cromolyn, Pancuronium bromide, Cortisone, Tibolone, Novobiocin, Silybin, Idarubicin, Bromocriptine, Diphenoxylate, Benzylpenicilloyl G, Dabigatran etexilate, Betulonal, Gnidicin, 2(3,30(3-Dihydroxy-3,4-seco-friedelolactone-27-lactone, 14-Deoxy-11,12-didehydroandrographolide, Gniditrin, Theaflavin 3,3'-di-O-gallate, (R)-((1R,5aS,6R,9aS)-1,5a-Dimethyl-7-methylene-3-oxo-6-((E)-2-(2-oxo-2,5-dihydrofuran-3-yl)ethenyl)decahydro-1H-benzo [c] azepin-1-yl)methyl 2-amino-3-phenylpropanoate, 2β-Hydroxy-3,4-seco-friedelolactone-27-oic acid, 2-(3,4-Dihydroxyphenyl)-2-[[2-(3,4-dihydroxyphenyl)-3,4-dihydro-5,7-dihydroxy-2H-1-benzopyran-3-yl] oxy]-3,4-dihydro-2H-1-benzopyran-3,4,5,7-tetrol, Phyllaemblicin B, 14-Hydroxycyperotundone Andrographiside, 2-((1R,5R,6R,8aS)-6-Hydroxy-5-(hydroxymethyl)-5,8a-dimethyl-2-methylenedecahydronaphthalen-1-yl)ethyl benzoate, Sugetriol-3,9-diacetate, Baicalin, (1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl 5-((R)-1,2-dithiolan-3-yl) pentanoate, 1,7-Dihydroxy-3-methoxyxanthone, 1,2,6-Trimethoxy-8-[(6-O-β-d-xylopyranosyl-β-d-glucopyranosyl)oxy]-9H-xanthen-9-one, 1,8-Dihydroxy-6-methoxy-2-[(6-O-β-d-xylopyranosyl-β-d- glucopyranosyl)oxy]-9H-xanthen-9-one, and 8(β-d-Glucopyranosyloxy)-1,3,5-trihydroxy-9H-xanthen-9-one.

In some embodiments, the additional pharmaceutically active agent comprises one or more anti-SARS-CoV-2 antibodies. In some embodiments, the antibody is a monoclonal antibody. In some embodiments, the antibodies are polyclonal antibodies, such as those obtained from convalescent serum of recovered patients. In some embodiments, the antibody targets the spike protein. In some embodiments, the antibody targets the receptor binding domain (RBD) of the SARS-CoV-2 spike protein. The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments, dual affinity retargeting antibodies (DART)), single chain Fv (scFv) mutants, multispecific antibodies such as bispecific and trispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity.

The combined administration includes co-administration, using separate formulations or a single pharmaceutical formulation, and consecutive administration in either order, wherein preferably there is a time period while both (or all) active agents simultaneously exert their biological activities.

Single or multiple administrations of the compositions that are disclosed herein can be administered depending on the dosage and frequency as required and tolerated by the patient. The dosage can be administered once but may be applied periodically until either a therapeutic result is achieved or until side effects warrant discontinuation of therapy.

In some embodiments, the cytokine storm syndrome is caused by a viral infection and the method further comprises administering a therapeutically effective amount of an anti-viral agent. Illustrative anti-viral agents include, but are not limited to, abacavir sulfate, acyclovir especially acyclovir sodium, adefovir, amantadine especially amantadine hydrochloride, amprenavir, ampligen, atazanavir, cidofovir, darunavir, delavirdine especially delavirdine mesylate, didanosine, docosanol, dolutegravir, edoxudine, efavirenz, emtricitabine, elvitegravir, enfuvirtide, entecavir, famciclovir, fomivirisen especially fomivirsen sodium, foscarnet especially foscarnet sodium, ganciclovir, ibacitabine, idoxuridine, imiquimod, indinavir especially indinavir sulfate, inosine pranobex, lamivudine, lopinavir, maraviroc, metisazone, moroxydine, nelfinavir especially nelfinavir mesylate, nevirapine, nitazoxanide, oseltamivir particularly oseltamivir phosphate, penciclovir, peramivir, pleconaril, podophyllotoxin, raltegravir, ribavirin, rimantadine especially rimantadine hydrochloride, ritonavir, saquinavir especially saquinavir mesylate, sofosbuvir, stavudine, telaprivir, tenofovir, tipranavir, trifluridine, tromantadine, umifenovir, valacyclovir especially valacyclovir hydrochloride, valganciclovir, vicriviroc, vidarabine, viramidine, zalcitabine, zanamivir, zidovudine and pharmaceutically acceptable salts and combinations thereof.

In another embodiment, the cytokine storm syndrome is caused by a bacterial infection and the method further comprises administering a therapeutically effective amount of an antibiotic. Illustrative anti-bacterial agents include, but are not limited to, quinolones (e.g. amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin, gemifloxacin, and garenoxacin), tetracyclines, glycylcyclines and oxazolidinones (e.g. chlortetracycline, demeclocycline, doxycycline, lymecycline, methacycline, minocycline, oxytetracycline, tetracycline, tigecycline; linezolide, eperezolid), glycopeptides, aminoglycosides (e.g. amikacin, arbekacin, butirosin, dibekacin, fortimicins, gentamicin, kanamycin, menomycin, netilmicin, ribostamycin, sisomicin, spectinomycin, streptomycin, tobramycin), .beta.-lactams (e.g. imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephacetrile, cephalexin, cephaloglycin, cephaloridine, cephalothin, cephapirin, cephradine, cefinetazole, cefoxitin, cefotetan, azthreonam, carumonam, flomoxef, moxalactam, amdinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), rifamycins, macrolides (e.g. azithromycin, clarithromycin, erythromycin, oleandomycin, rokitamycin, rosaramicin, roxithromycin, troleandomycin), ketolides (e.g. telithromycin, cethromycin), coumermycins, lincosamides (e.g. clindamycin, lincomycin), chloramphenicol, clofazimine, cycloserine, dapsone, ethambutol hydrochloride, isoniazid, pyrazinamide, rifabutin, rifampin, rifapentine and streptomycin sulfate.

In another embodiment, the cytokine storm syndrome is caused by a fungal infection and the method further comprises administering a therapeutically effective amount of an anti-fungal agent. Illustrative anti-fungal agents include, but are not limited to, abafungin, albaconazole, amorolfine, amphotericin B, amphotericin B cholesteryl sulfate complex, amphotericin B lipid complex, amphotericin B liposomal, anidulafungin, bifonazole, butenafine, butoconazole, candicidin, caspofungin, clotrimazole, econazole, efinaconazole, fenticonazole, fluconazole, flucytosine, griseofulvin microsize, griseofulvin ultramicrosize, hamycin, isavuconazole, isoconazole, itraconazole, ketoconazole, luliconazole, micafungin, miconazole, naftifine, natamycin, nystatin, omoconazole, oxiconazole, posaconazole, propiconazole, ravuconazole, sertaconazole, sulconazole, terbinafine including terbinafine hydrochloride, terconazole, tioconazole, voriconazole, and pharmaceutically acceptable salts and combinations thereof.

In some embodiments, the cytokine storm syndrome is caused by a protozoal infection and the method further comprises administering a therapeutically effective amount of an anti-protozoal agent. Illustrative anti-protozoal agents include, but are not limited to, atovaquone, metronidazole including metronidazole hydrochloride, pentamidine including pentamidine isethionate, chloroquine including chloroquine hydrochloride and chloroquine phosphate, doxycycline, hydroxychloroquine sulfate, mefloquine including mefloquine hydrochloride, primaquine including primaquine phosphate, pyrimethamine, pyrimethamine with sulfadoxine, trimethoprim, sulfamethoxazole, clindamycin, quinine, quinidine, sulfadiazine, artemether, lumefantrine, artesunate, nitazoxanide, suramin, melarsoprol, eflornithine, nifurtimox, stibogluconate including sodium stibogluconate, amphotericin B including liposomal amphotericin B, miltefosine, paromomycin, ketoconazole, itraconazole, fluconazole, and pharmaceutically acceptable salts and combinations thereof.

In some embodiments, the patent can be administered an additional anti-inflammatory therapy, such as, for example, steroids, intravenous immunoglobulin (IVIG), selective cytokine blockade (e.g., anakinra or tocilizumab), and/or therapies that inhibit JAK/STAT. In some embodiments, chloroquine can be administered.

In some embodiments, the patient can be administered an additional immunosuppressive agent. Illustrative immunosuppressive agents include, but are not limited to: corticosteroids such as, for example, budesonide, prednisone and prednisolone; mTOR inhibitors such as, for example, sirolimus and everolimus; and monoclonal antibodies such as, for example, adalimumab, infliximab, certolizumab, natalizumab, ustekinumab and vedolizumab, and biosimilars thereof.

When a second agent (e.g., anti-viral, antibiotic, and/or anti-fungal) is also administered, it will typically be used as prescribed. In some embodiments, the second agent is administered simultaneously or at different times from the cytokine storm drug (first agent). In some embodiments, the second agent is administered via the same (e.g., IV/IV) or different (e.g., IV/oral) routes. In some embodiments, the second agent is co-administered (e.g., both first and second agents administered via the same IV).

In some embodiments, the subject will be administered the combination in a single composition that will comprise each of the ingredients in a single administration form, such as a pill, tablet, capsule, oral solution, infusion, or any of the forms described herein. In some embodiments, a kit comprising each of the individual active ingredients, together with instructions for administering each ingredient. In some forms of the kit, certain ingredients will already be combined such that one, two, three, four, or more of the components or ingredients of the composition are in a single administration form as described herein.

All publications herein are incorporated by reference to the same extent as if each individual publication or patent application was specifically and individually indicated to be incorporated by reference.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLES

Example 1. Regadenoson is Safe and Reduces Inflammation in Hospitalized COVID-19 Patients The present example establishes that regadenoson infusion is safe and rapidly suppress proinflammatory cytokine production and invariant natural killer T (iNKT) cell activation in COVID-19 patients.

In cohort 1 of this trial, we tested the safety, tolerability, and toxicity of regadenoson in 5 COVID-19 patients (WHO stages 4-5) receiving supplemental oxygen without mechanical ventilation. All subjects received an infused loading dose of 5.0 µg/kg up to a maximum of 400 µg over 30 minutes, followed by a maintenance dose of 1.44 µg/kg/hr for 6 hours. Toxicity of regadenoson was graded by using Common Terminology for Adverse Events Criteria. Vital signs, pulse oximetry, arterial blood gas, laboratory studies, and electrocardiograms were performed on a schedule commensurate with level of care to identify potential risk of the study drug during and 12 hours post infusion. The trial was monitored by an NIH designated DSMB. Peripheral blood samples were collected at 4 timepoints. Along with clinical monitoring, plasma levels of cytokines (14-plex Luminex panel) were measured at various time points. Cytokine data were analyzed by SAS 9.5 PROC MIXED. Activation of peripheral blood mononuclear cells including iNKT cells was analyzed by flow cytometry. Flow cytometry data were analyzed by FCS Express 7 Research edition and GraphPad Prism v9. The plasma levels of regadenoson were determined via liquid chromatography-mass spectrometry.

The 5 enrolled patients were all unvaccinated and received low dose dexamethasone as standard of care. All recovered and were discharged in 3-9 days. No serious adverse events were observed. Transient and self-limiting nausea was reported by a single subject. Vital signs were stable throughout the infusion and 12 hours post infusion. SpO2 measured before regadenoson infusion was significantly less (P<0.05) than 24 hours after treatment. Twelve of the fourteen measured cytokines were reduced after 4 hours of regadenoson infusion (FIG. 1). Regadenoson significantly reduced expression of the activation marker, CD69, on circulating iNKT cells after the 30 min loading dose (P=0.0027) and 4 hours into the maintenance dose (P=0.0357). The inhibition of iNKT cells was reversible since the fraction of CD69+iNKT cells increased after cessation of regadenoson infusion. The median peak plasma levels of regadenoson were 14.24 ng/ml (range 3.64-78.64 ng/mL).

Regadenoson infusion appears safe in moderately ill COVID-19 patients. Results indicate regadenoson has an anti-inflammatory effect in COVID-19 patients by reducing several proinflammatory cytokines and the activation of iNKT cells.

Example 2: Treatment of COVID-19 with $A_{2A}R$ Agonists

We tested the therapeutic efficacy of apadenoson in preventing the onset and progression of SARS CoV-2 infection in the K18-hACE2 mouse model of COVID-19. This is a model of severe COVID-19, with nearly 100% mortality by five to six days post-infection (MOREAU et al., Am. J. Trop. Med. Hyg., (2020), 103:1215-1219). The results indicate that apadenoson administered after SARS CoV-2 infection decreased weight loss, improved clinical symptoms, reduced several proinflammatory cytokines in the BAL fluid, and increased survival in K18hACE2 transgenic mice.

Results

Figure 2:
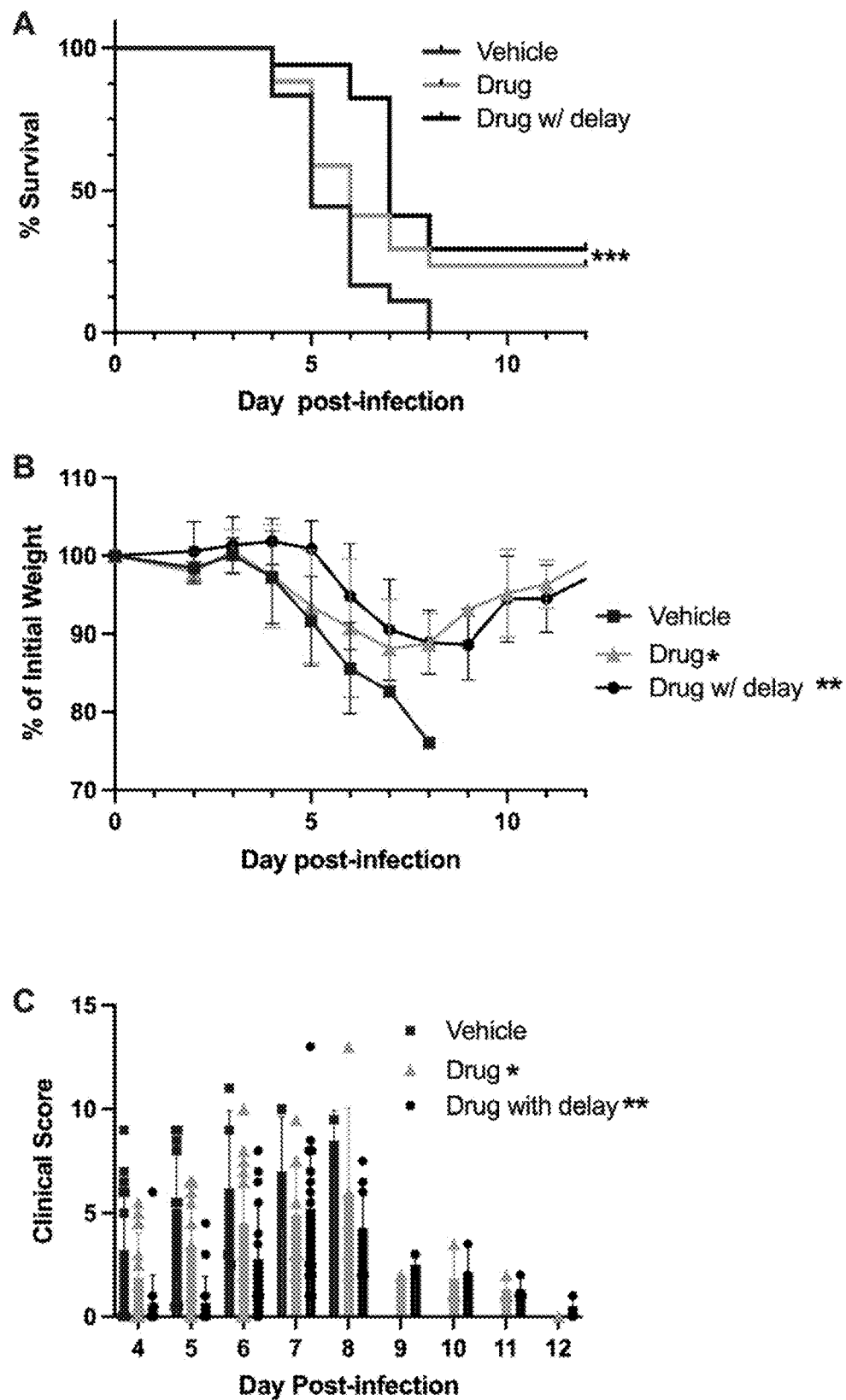
FIG. 2. Treatment with apadenoson improved survival and delayed time to death. Mice were treated 18 hours before or five hours after infection with apadenoson delivered by an osmotic pump. Data combined from three independent experiments. A) Survival curves, used Log Rank (Mantel Cox) test, p=0.0002*** for drug with delay compared to vehicle, B) Average weight loss: P values from linear mixed model for difference in slope of vehicle compared to drug, p=0.02*, vehicle compared to drug with delay, p=0.002** and C) Clinical Scores: P values from linear mixed model for difference in slope of vehicle compared to drug, p=0.027*, vehicle compared to drug with delay, p=0.001**

Apadenoson administration improves outcomes of SARS-CoV-2 infection in K18-hACE2 mice. K18-hACE2 mice, ranging in age from 17 to 30 weeks were divided into three groups. One group received saline (vehicle), another received apadenoson 18 hours before viral challenge (drug)

and a third received apadenoson five hours post viral challenge (drug with delay). The mice were challenged intranasally with 1250 PFU SARS CoV-2. Mouse weight and clinical scores were recorded daily. Mice were euthanized when they met the criteria for euthanasia (see methods) or at the end of the experiment, which was day 12 post viral challenge. Apadenoson, given either pre- or post-challenge, improved survival and delayed the onset of symptoms (FIG. 2). Apadenoson administration beginning five hours after challenge was more effective in delaying the time to death, although the overall survival was the same in both drug and drug with delay treatment groups. All mice in the vehicle treatment group met the criteria for euthanasia by day 8 (0/18 surviving); 24% (4/17) of the mice survived to the end of the experiment in the drug treatment group and 30% (5/17) survived in the drug with delay treatment group (FIG. 2A). The survival curve for the drug with delay-treated group was significantly different than vehicle (p=0.0002). The survival curve for the drug-treated group did not differ significantly from the vehicle-treated group (p=0.066). The drug and drug with delay-treated groups had statistically significantly lower clinical scores and less weight loss when compared to the vehicle-treated group (FIGS. 2B & 2C).

Apadenoson treatment elicits cytokine and chemokine responses that are associated with a decrease in weight loss. To assess how apadenoson treatment may be delaying the onset of severe symptoms, mice were treated as before with either vehicle (saline) or apadenoson, delivered with a five-hour delay by osmotic pumps, then euthanized on day five post-infection. The weight loss and clinical scores of mice in both vehicle and drug with delay-treated animals were heterogeneous on day five and not statistically different between groups (FIG. 3).

Cytokines and chemokines were measured in the BAL fluid using a mouse 31 plex Luminex panel. The levels of 18/31 cytokines/chemokines (IL-1a, IL-1b, IL-2, IL-4, IL-5, IL-7, IL-9, IL-10, IL-12p40, IL-12p70, IL-13, IL-15, IL-17, GM-CSF, LIX, MIP-1a, MIP2, & M-CSF) were not different between uninfected, vehicle-infected control and drug with delay-infected mice (data not shown). Uninfected mice received either saline or apadenoson via an osmotic pump; regardless of treatment these mice all had low levels of cytokines and chemokines.

Figure 4:
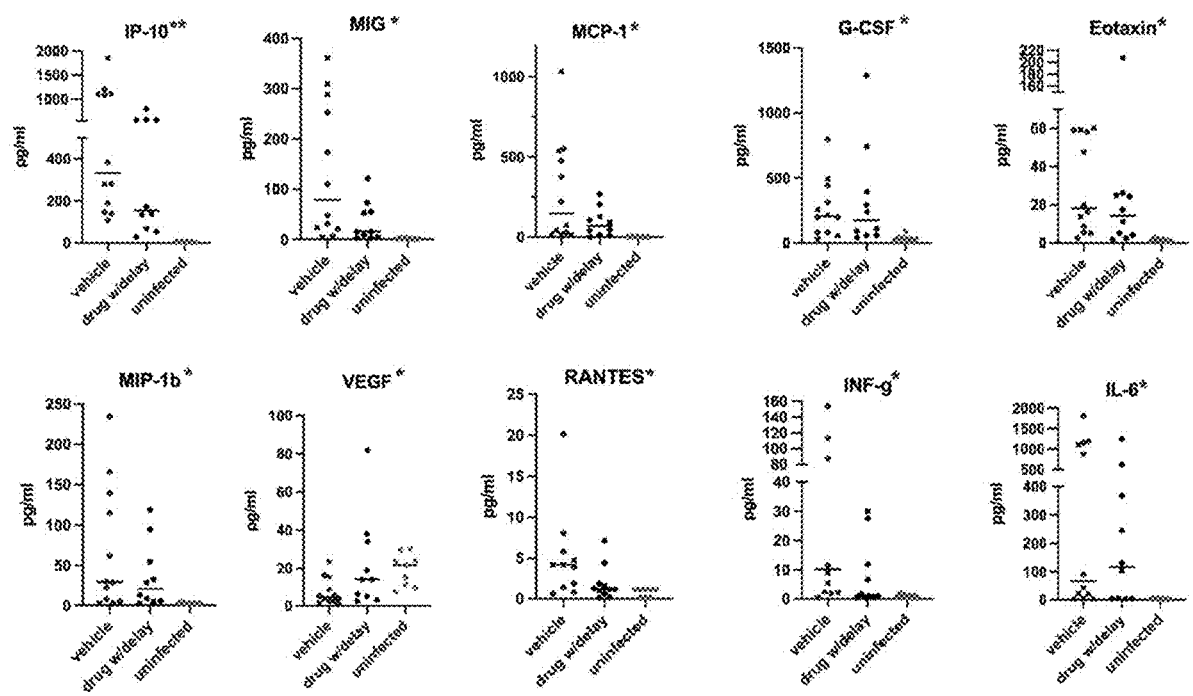
FIG. 4. Statistically significant differences in cytokine and chemokine levels in SARS CoV-2-infected mice treated with apadenoson. Mice were euthanized on day five post-infection. Cytokine/chemokine levels were measured in BAL fluid by a Luminex. Combined results of two independent experiments. Statistical differences in cytokine/chemokine levels were analyzed using Welch's ANOVA. Raw p values <0.05*, 0.005**
Figure 4:
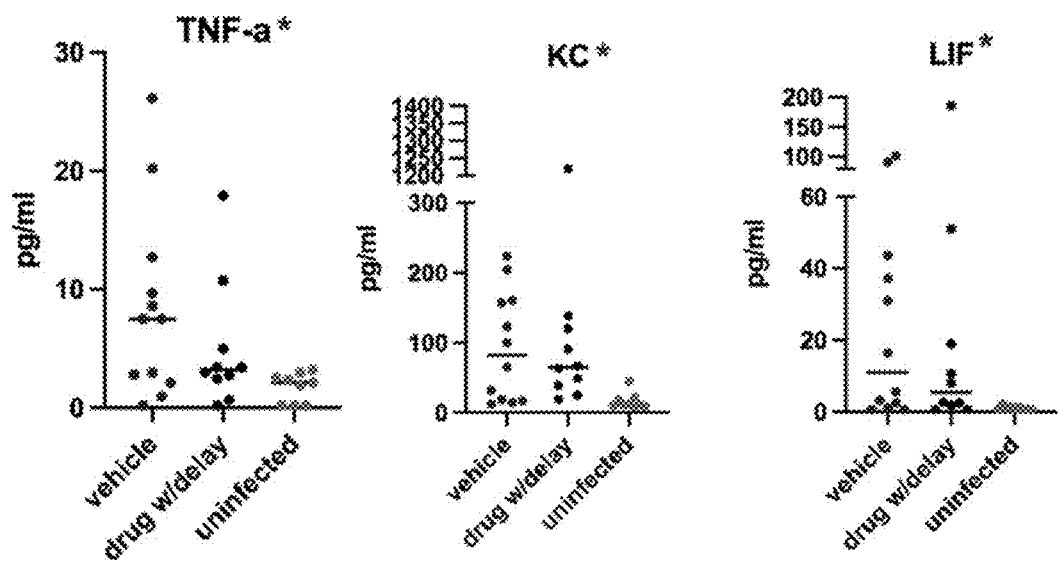

The levels of 13/31 cytokines/chemokines (IP-10, MIG, MCP-1, G-CSF, Eotaxin, MIP1b, VEGF, RANTES, INF-g, IL-6, TNF-a, KC, LIF) were statistically different by ANOVA and raw p value (FIG. 4). Using ANOVA p values adjusted for multiple testing, only IP-10 remained significant (p=0.022). Based on the results of Dunnett's T3 comparisons, the levels of nine cytokines or chemokines (IP-10, MIG, MCP-1, G-CSF, Eotaxin, MIP1b, IL-6, TNF-α, KC) were higher in vehicle-infected compared to uninfected controls (p<0.05). VEGF was notable because it was lower in vehicle-treated mice compared to uninfected mice (p=0.011). Only MCP-1 and IP-10 were statistically higher in the drug with delay-infected group compared to vehicle (p=0.0351, and p=0.0223, respectively). The levels of eight cytokines and chemokines (MIG, G-CSF, Eotaxin, MIP1b, VEGF, INF-g, TNF-a, KC) in the drug with delay treatment group were not significantly different from uninfected mice. Taken together, these results demonstrate that treatment with apadenoson lowers the levels of a subset of proinflammatory cytokines and chemokines to baseline values.

Figure 5:
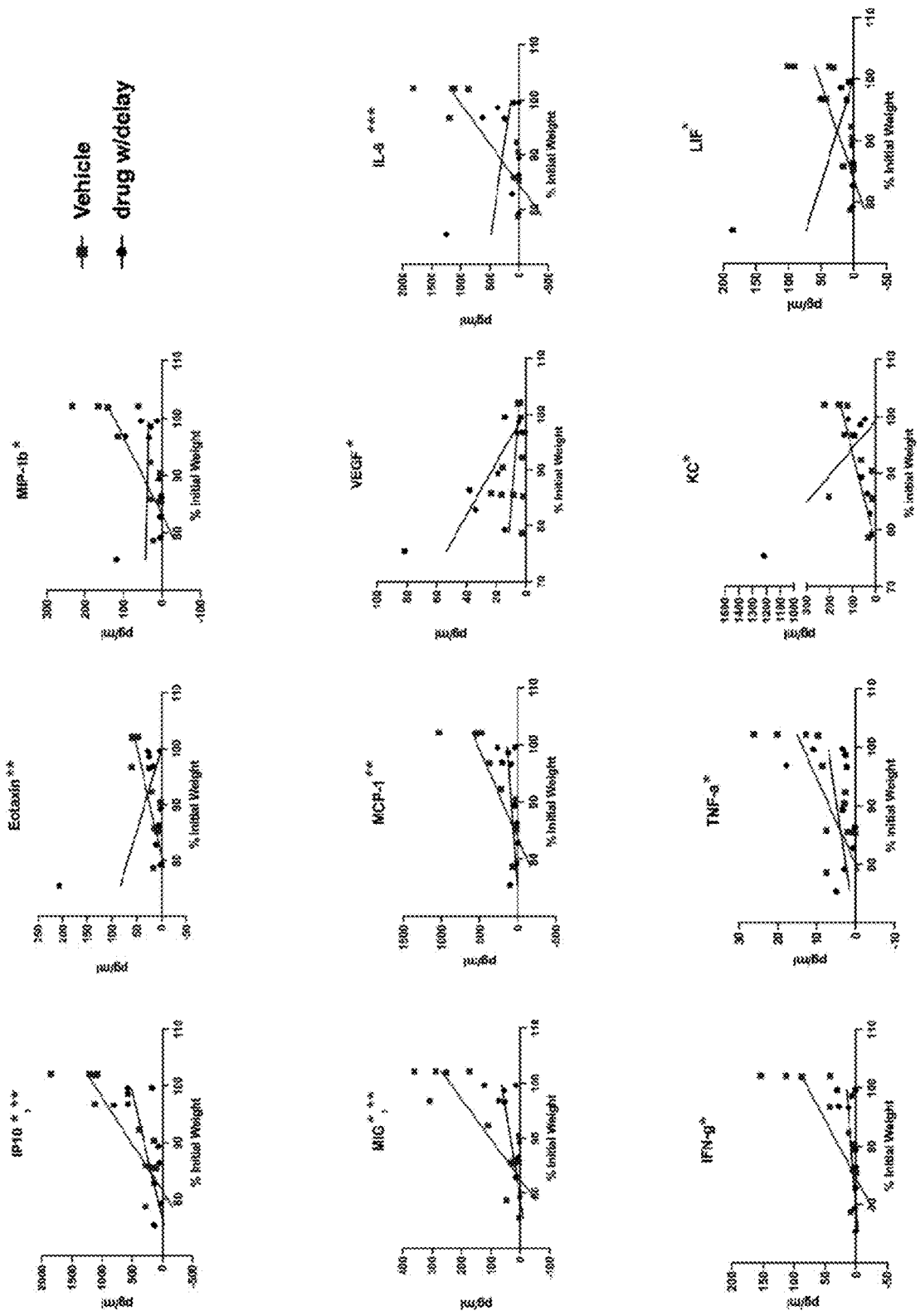
FIG. 5. Associations of BALF cytokine and chemokine levels and weight loss. P values <0.05*, <0.005** calculated using linear regression, (blue asterisks indicate p value significance for vehicle treatment group, black asterisks for drug with delay treatment group). These results are combined from two independent experiments.

The levels of most cytokines exhibited a wide range of values within a treatment group, similar to the observed heterogeneity seen in weight loss and clinical scores. Therefore, linear relationships between cytokine levels and weight loss were examined (FIG. 5). Higher levels of IP-10 and MIG were associated with less weight loss in both drug with delay- and vehicle-treated groups; p values were <0.05 in drug with delay treatment group, and <0.005 in vehicle treatment group. Lower levels of VEGF were associated with less weight loss in the drug-treatment group, p value=0.007. In the drug with delay treatment group, cytokine and chemokine levels were overall lower than in vehicle-treated mice, and with the exception of IP-10, MIG, and VEGF, not associated with the degree of weight loss. For the vehicle treatment group, higher levels of eight additional cytokines and chemokines were associated with less weight loss (Eotaxin, KC, MCP-1, MIP-1b, IL-6, INF-g, TNF-a, and LIF). There was an outlier in the drug with delay treatment group; this mouse had the most weight loss and had very high levels of five cytokines (Eotaxin, MIP-1b, IL-6, KC and LIF) that were not consistent with the associations with weight loss with mice in either group. These results suggest an extremely dysregulated immune response in this mouse, but there was no apparent explanation. In these experiments, when mice were euthanized on day five post-infection, only about half of the mice in each group had reached the established criteria for euthanasia (see methods and note clinical scores in FIG. 4). With the one exception noted above, mice in either treatment group with 20% or more weight loss had low levels of cytokines. These results suggest that higher cytokine levels in the vehicle treatment group are associated with a slower progression in weight loss, and potentially a delay in time to eventual death, whereas apadenoson-treated mice exhibited a slower progression in weight loss without elevated cytokines and potentially an increased chance of survival or recovery.

Figure 6:
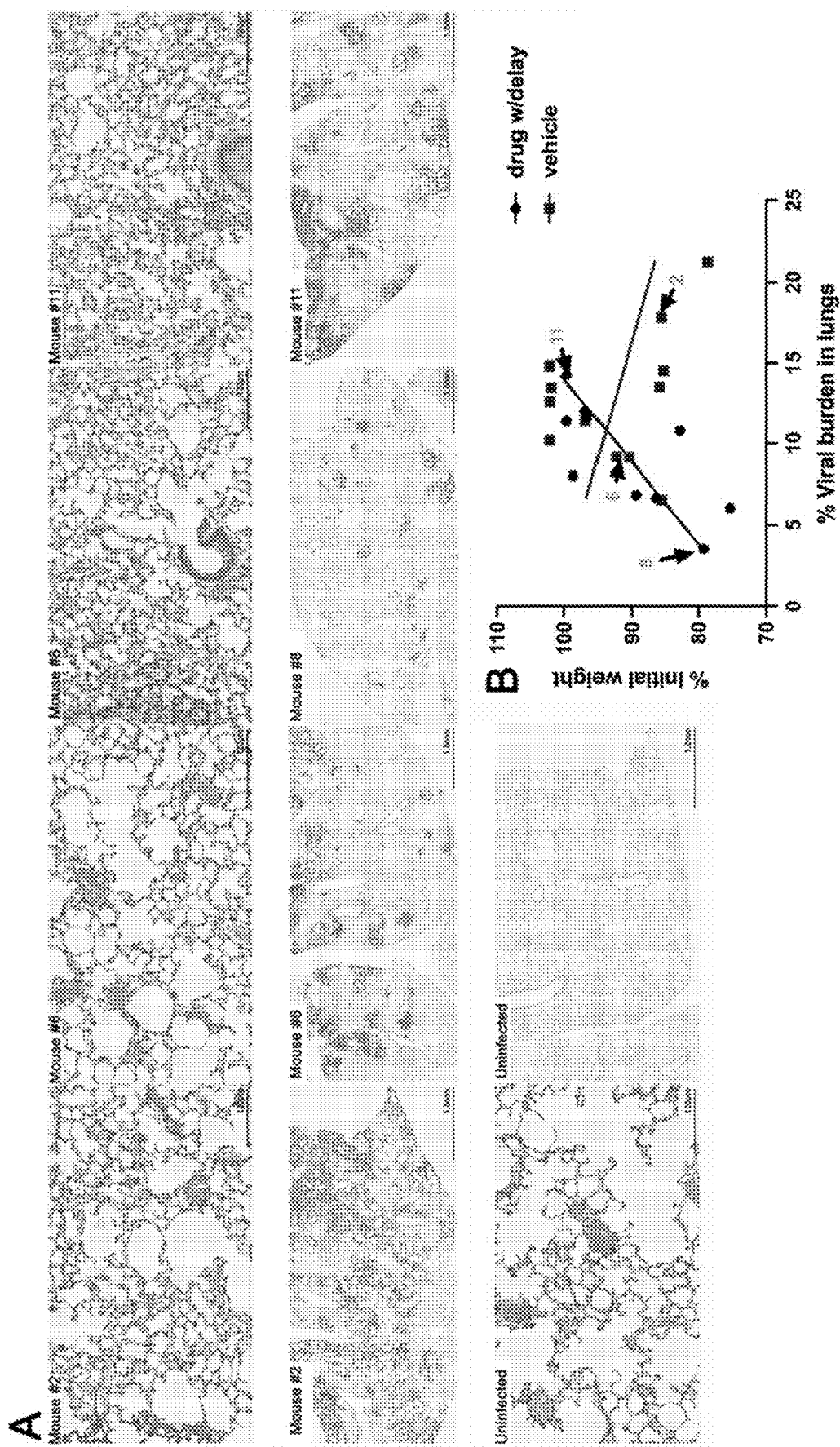
FIG. 6. Viral burden on day five post-infection in apadenoson-treated mice negatively correlates with weight loss. A) Lungs stained with H&E or an anti-NP antibody. Mice #2 and 6 were vehicle-treated; Mice #8 and #11 were drug-treated. H&E-stained lungs are shown at a higher magnification than IHC slides. B) The weight and viral burden of mice shown in the H&E stained slides are indicated in orange numbers with black arrows on the graph. Association in drug delay group was calculated using simple linear regression, p value=0.0163. There was no significant association in the vehicle treatment group. The percent viral burden in the lungs was determined using ImageJ.

Viral burdens and titers in the lungs in apadenoson-treated mice. To assess the effects of apadenoson treatment on viral burden, the presence of the virus in the lungs was measured by immunohistochemistry (IHC) staining with an anti-viral NP protein on day five post-infection (FIG. 6A) and followed by the percentage of lung stained with the antibody. The viral burden in drug with delay-treated mice was inversely associated with weight loss, but the same was not true in the vehicle-treated group (FIG. 6B, p=0.0163). Of note, in the drug with delay treatment group mice with the most weight loss (e.g., mouse #8 in FIG. 6), had the least amount of viral staining in the lungs and mice with little to minimal weight loss had the highest lung burden (e.g., mouse #11, FIG. 6). Viral burden and weight loss were not associated in the vehicle-treated group, supporting the characterization of COVID-19 as an inflammatory disease with dysregulated immune responses.

We also assessed viral titer and burden in the lungs of mice that met the criteria for euthanasia and in mice that survived infection (after restoration of weight and no discernable clinical score, see FIGS. 2B & C). Weight loss and viral titer were significantly associated with apadenoson given before infection (FIG. 7A, p=0.0207) based on simple logistic regression (FIG. 7A), but was not significant in apadenoson given after infection (drug with delay) or in vehicle-treated mice. However, surviving mice in both drug treatment groups had viral titers below the limit of detection, whereas the vehicle-treated mice, none of which survived, all had detectable titers (FIG. 7A). The average viral titer in the drug with delay treatment group trended lower, but was not significant (FIG. 7B). However, the viral burden, determined by IHC staining was significantly lower in the drug with delay treatment group (FIG. 7C, p=0.0012). In summary, surviving mice, which included only mice that had received apadenoson (FIG. 2A), had no detectable live virus in their lungs, and lower viral burdens by IHC. There was no significant difference in the viral titers among the non-survivors regardless of treatment group. These results suggest that the pharmacological effects of apadenoson result in lowering viral burden despite downregulating several aspects of the inflammatory response.

Discussion

Immune system activation is essential for killing COVID-19 and other viruses, but prolonged hyperinflammation and immune dysregulation contribute to poor outcomes in COVID-19 disease (MERAD et al., Nat. Rev. Immunol., (2020), pg. 355-362; COPERCHINI et al., Cytokine Growth Factor Rev., (2020), 53:25-32). Adenosine agonists represent attractive therapies for COVID-19, because they limit several elements of immune responses and promote tissue repair (CHHABRA et al., Curr. Diabetes Rev., (2012), 8:419-433). We used the transgenic K18hACE2 mouse, which expresses the human ACE2 receptor, as a model of severe COVID-19 disease. This model shares several characteristics of severe COVID-19 disease including impaired lung function, high levels of proinflammatory cytokines and chemokines, and immune cell infiltration of the lungs (YINDA et al., PLOS Pathog, (2021), 17, e1009195; WINKLER et al., Immunol, (2020), 21, 1327-1335). We have shown in this mouse model that apadenoson, administered five hours after infection, is capable of delaying the progression of symptoms and death.

Mice treated after infection with apadenoson had dampened immune responses compared to vehicle controls, as measured by reduced levels of a subset of cytokines and chemokines that were similar to baseline levels in uninfected mice. Nine cytokines and chemokines were increased in vehicle-treated mice (IP-10, MIG, MCP-1, G-CSF, Eotaxin, MIP1b INF-g, TNF-a, KC) compared to uninfected controls (FIG. 3). These cytokine and chemokine profiles in the vehicle-treated infected mice are similar to other reports in K18hACE2 mice lungs (YINDA et al., PLOS Pathog, (2021), 17, e1009195; WINKLER et al., Immunol, (2020), 21, 1327-1335) and confirm the inflammatory nature of COVID-19 infection in this model.

To explore the impact of apadenoson on cytokine/chemokine levels further these levels were correlated with percent weight loss. On day five, when half of the mice in each group met the criteria for euthanasia (FIG. 3), there was an association between low levels of cytokines and increased weight loss in vehicle-treated mice (FIG. 5). In the drug with delay treatment group only higher levels of IP10, and MIG were associated with less weight loss (FIG. 5). The remaining cytokines in the drug with delay treatment group were low, regardless of the amount of weight loss. The sole exception was VEGF, which was higher in animals with increased weight loss, though this association was only significant in drug with delay-treated mice. VEGF promotes vascular permeability, which can lead to tissue damage, and is elevated in COVID-19 patients (HUANG et al., The Lancet, (2020), 395, 497-506). A promising preliminary COVID-19 treatment trial with bevacizumab, an anti-VEGF monoclonal antibody, suggests that this treatment may be beneficial. (PANG et al., Nat. Commun., (2021), 12, 814). Although we did not do a time course of cytokine induction, our results suggest that in this model cytokine levels peak before severe weight loss and symptomatic disease occur, but then drop as the disease progresses.

Figure 7:
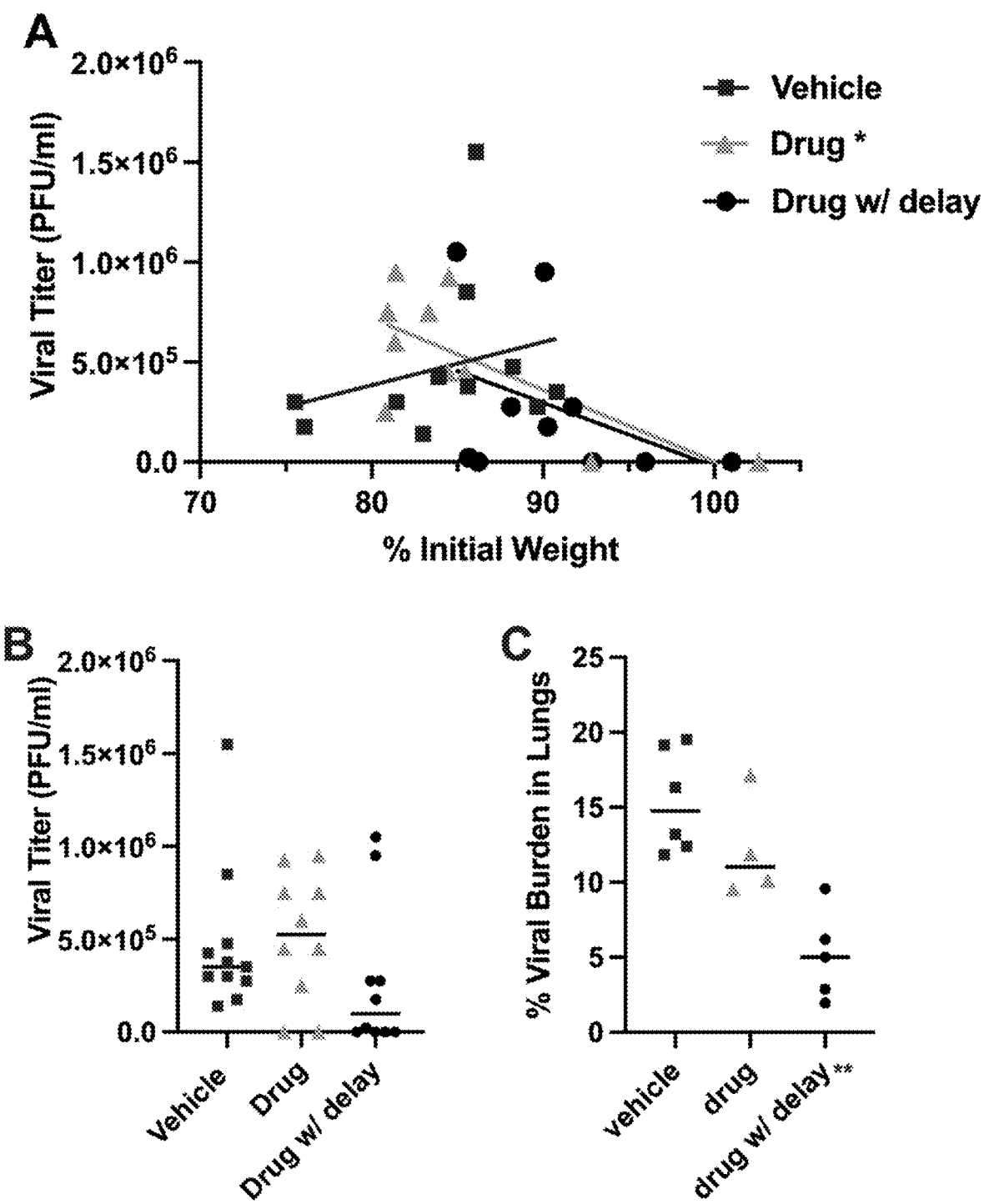
FIG. 7. Association of viral titer and weight loss in mice and burden in lungs in apadenoson-treated mice. A) Weight loss was significantly associated with viral titer in mice treated with apadenoson before infection (drug, p=0.0207*), but not in vehicle or drug with delay treatment groups. Slopes were calculated using simple linear regression. Virus was not detected in surviving mice. B) Viral titers of lung homogenates trended lower in drug with delay-treated mice but were not significant using Welch's ANOVA. C) Viral burdens, as measured by IHC, were significantly lower in drug with delay-treated mice (p=0.0012**) using Welch's ANOVA.

Apadenoson treatment also influenced viral burden in lung. In mice that were euthanized on day five post-infection, which in this model is the day when weight loss and adverse clinical symptoms become apparent, there was an inverse relation between viral lung burden and weight loss in the drug with delay-treated mice, but no strong association in the vehicle-treated mice (FIG. 6). Of note, mice in both groups that had not yet exhibited weight loss on day five post-infection tended to have viral lung burdens between 10-15%. Based on the drug treatment trials in FIG. 2, we would expect that all vehicle-treated mice would have succumbed to infection, while some of the apadenoson-treated mice would have survived. Therefore, we next examined the viral titers and burden in the lungs of mice that were euthanized or recovered (FIG. 7). While viral titers were not strongly related to weight loss, the surviving apadenoson-treated mice did not have detectable titers, and viral burden was significantly lower with mice given apadenoson after infection, suggesting that apadenoson can also lead to clearance of the virus. Overall, these findings suggest that the use of anti-inflammatory drugs such as apadenoson to limit inflammation during cytokine storm is beneficial and remarkably, and may even reduce viral burden in the lung. These data support the use and further exploration of apadenoson, or other adenosine agonists, as supportive care for COVID-19 patients.

Methods

Infection and treatment: Twenty-four hours prior to infecting Tg(K18-hACE2)$_2$Prlmn (Jackson Laboratories) male mice with SARS CoV-2, primed 7-day Alzet® osmotic pumps (Durect, Cuperton, CA) containing saline or drug were implanted subcutaneously (MCCRAY et al., J. Virol., (2007), 81:813-821). In the drug with delay treatment group drug delivery was delayed by 24 hours by adding 2.5 cm long tubing to the pump. Apadenoson was delivered at a rate of 1.5 µg/kg/hr. Uninfected littermates received saline or drug with delay via osmotic pumps. Mice were challenged with 1250 plaque forming units (PFU) of Hong Kong/VM20001061/2020 (NR-52282, BEI Resources) via intranasal route under ketamine/xylazine anesthesia. Mice were examined twice daily for clinical symptoms and scored using the following criteria: weight loss (0-5, in 5% of initial weight loss increments), reduced activity (0-3), ruffled fur appearance and hunched posture (0-2), and an eye closure (0-2). Mice were euthanized when weight was <80% of initial weight or when they scored a maximum in two symptom categories. This experiment was repeated three times, with six animals per treatment group each time. One mouse in the drug and one in the drug with delay did not survive anesthesia. Statistical differences in weight loss and clinical scores by treatment group were determined using linear mixed models accounting for day post-infection and the day the mouse died (lme4 and lmerTest packages (BATES et al., J. Stat. Softw., (2015), 67; KUZNETSOVA et al., J. Stat. Softw., (2021), 82) in R (R Core Team 2021). For mice surviving to the end of the experiment (day 12 post-infection), day of death=15 was used. All mouse work was approved by the University's Institutional Animal Care and Use Committee and all procedures were performed in the University's certified animal Biosafety Level Three laboratory, which is fully accredited by the Association for the Assessment and Accreditation of Laboratory Animal Care, International (AAALAC).

BAL Cytokines: BAL fluid was collected with 700 µL of PBS and cells were removed via centrifugation. The BAL fluid was analyzed by a Luminex Magpix by the UVA Flow Cytometry Core facility using a Mouse 31 plex panel. Statistical changes in cytokine levels were analyzed using Welch's ANOVA followed by Dunnett's T3 multiple comparisons (Graphpad Prism 9.0). P values were adjusted for multiple testing using the Holm-Sidak method.

Viral Lung titers: Titers were determined as described in Moreau et al. (MOREAU et al., Am. J. Trop. Med. Hyg., (2020), 103:1215-1219). Briefly, lungs were homogenized in serum-free DMEM. Titers were determined by infecting Vero C1008, Clone E6 (ATCC CRL-1586) with serial dilutions of the homogenate. After a two-hour incubation, the diluted homogenates were replaced with a liquid overlay of DMEM, 2.5% FBS containing 1.2% Avicel PH-101 (Sigma Aldrich, St. Louis, MO) and incubated at 37° C., 5% CO2. After three days, the overlay was removed, wells were fixed with 10% formaldehyde, and stained with 0.1% crystal violet to visualize plaques. Plaques were counted and PFUs were calculated according to the following equation: Average # of plaques/dilution factor×volume of diluted virus added to the well.

Histology: Tissues were fixed in 10% formalin. To visualize virus in the lungs, slides were stained with SARS-CoV2 specific anti-nucleoprotein antibody (Cat. No. 9099, ProSci, Poway, CA) as per manufacturer's instructions and then scanned at 20× magnification. The percentage of lung tissue infected with virus was calculated (ImageJ, version 1.53K).

Example 3. Treatment of Moderate to Severe COVID-19 Adult Patients with Reg adeno s on Methods Patient Treatment Consented Covid-19 patients were treated with RA administered intravenously using a pediatric infusion pump at a loading dose rate of 5 µg/kg/hr for 30 min followed by a maintenance dose of 1.44 µg/kg/hr for 6 hours. Subjects' vital signs including oxygen saturation (SpO2), blood pressure, heart rate and respiratory rate were monitored throughout RA infusion.

Blood Collection and Processing

Blood samples were drawn as a source of peripheral blood mononuclear cells (PBMCs). Cells were frozen in 10% DMSO and thawed for analysis of live cells by flow cytometry. Cytokines, CRP, and D dimer levels were measured in plasma. Blood samples were collected just prior to the start of RA infusion (0 hr), just prior to the end of the loading dose (30 min), 4 hours into the maintenance dose (4.5 hr), and the next day (24 hr).

Flow Cytometry

Frozen live cells were thawed in 15 ml conical tubes, which were prefilled with 10 ml warm (37° C.) washing media (20% FBS-RPM1-1640) and mixed well. The cells were centrifuged at 500g for 10 minutes at RT, washed in 1×PBS and centrifuged again. Cells were resuspended in 1×PBS at 1X1QA7 cell/ml and transferred in 100 µl to 96 well plates for cell viability staining with Zombie NIR. The cells were then treated with human Fc block and stained with antibodies at 4° C. for 20 minutes. Samples (including single positive controls, FMOs, and stained samples) were fixed with 2% paraformaldehyde and analyzed with a Cytek Aurora at the Flow Cytometry Core Laboratory (UMB, Baltimore, MD). Data were analyzed using FCS Express 7 Research Edition (De Novo Software, Pasadena, CA).

TABLE 1

Antibodies used for flow cytometry experiments

| Specificity | Clone | Fluorochrome | Purpose | Vendor |
| --- | --- | --- | --- | --- |
| GD11b | M1/70 | BUV395 | Monocytes, NK Cells | BD Biosciences |
| CD8 | RPA-T8 | BUV496 | Cytotoxic T Cells | BD Biosciences |
| Cd11c | Bu15 | BV 421 | Dendritic Cells | Biolegend |
| CD14 | MφP9 | BV480 | Monocytes | BD Biosciences |
| CD4 | RPA-T4 | BV 510 | CD4+ T Cells | Biolegend |
| CD16 | 3G8 | BV 570 | NK Cells, Monocytes | Biolegend |
| CD3 | UCHT1 | BV 605 | Lineage T Cells | Biolegend |
| HLA DR | L243 | FITC | Activation | Biolegend |
| GD123 | 6H6 | PE | Plasmacytoid Dendritic Cells | Biolegend |
| CD19 | SJ25-C1 | PE-Ax610 | B Cells | Fisherthermo |
| TCR Va24-Ja18 | 6B11 | PerCP-eF710 | INKT Cells | Invitrogen |
| CD39 | A1 | PE-Cy7 | Activation | Biolegend |
| CD86 | BU63 | APC | Activation | Biolegend |
| CD69 | FN50 | Ax 700 | Activation | Biolegend |
| CD38 | HIT2 | APC/Fire 810 | Activation | Biolegend |
| Zombie | NA | NIR | Viability | Biolegend |

APC, allophycocyanin;
Ax, Alexa;
NIR, NIR dye for dead cell stain;
BUV, brilliant ultraviolet;
BV, brilliant violet;
Cy, cyanine;
FITC, fluorescein iso-thiocyanate;
PE, R-phycoerythrin;
PerCP, peridinin chlorophyll protein.

Measurement of Cytokines/Chemokines

Plasma levels of cytokines/chemokines were measured as previously described (MOLES et al., J Nucl Cardiol, (2018), 25: 820-827) using a Luminex assay kit (Millipore Sigma, Burlington, MA) in the Cytokine Core Laboratory at the University of Maryland (UMB), Baltimore. The customized panel detects IL-1, IL-2, IL-6, IL-7, IL-8, IL-12P40, IL-12P70, IL-17, IP-10/CXCL10, MCP-1/CCL2, MIP1a/CCL3, TNFa, and IFNy.

Treatment with RA in a Murine COVID-19 Model

Male 2-3-month-old 25-30 g 86.Cg-Tg(K18-ACE2)2Prlmn/J mice were obtained from Jackson Laboratories (MCCRAY et al., J Virol, (2007), 81: 813-821). These mice express the SARS-CoV-2 receptor, human angiotensin-converting enzyme 2 (hACE2) in epithelia and develop a usually lethal infection after intranasal inoculation with a human strain of the virus (MOREAU et al., Am J Trop Med Hyg, (2020), 103:1215-1219; WINKLER et al., Nat Immunol, (2020), 21:1327-1335). To treat COVID-19 in mice with RA, 7-day Alzet 10070 osmotic pumps with a pump rate of 0.5 µl/hr and containing saline or 80 µg/ml RA (1.44 µg/kg/hr) were implanted subcutaneously just prior to being challenged with 1250 Pfu of Hong Kong VM20001061/2020 (NR-52282, BEi Resources) via the intranasal route under ketamine/xylazine anesthesia. Infection began in airway epithelia, with subsequent alveolar involvement and resulted in pulmonary macrophage and lymphocyte infiltration. Mice were evaluated twice daily for clinical symptoms, including weight loss, reduced activity level, fur appearance, posture, and eye closure. Mice were euthanized when weight loss was >20% of initial weight or a maximum score in two symptom categories was observed. All mouse studies were approved by the University of Virginia Institutional Animal Care and Use Committee and performed in the University's certified animal Biosafety Level Three laboratory.

Statistical Analysis

Changes in patient circulating cytokine levels over time were analyzed using a repeated measures model with a spatial power covariance structure. After transforming to the log, data were analyzed using a log s ale to facilitate interpretation as fold changes relative to baseline. 95% confidence intervals were used to estimate changes from baseline at 30 minutes, 4.5 hours and 24 hours. Analyses were carried out in SAS 9.4 PROC MIXED. GraphPad Prism software 9 was used for statistical analysis of flow cytometry data. Results were evaluated with 95% confidence intervals, and the difference was considered statistically significant if P<0.05. Mice survival curves are based on the Log rank Mantel Cox test.

Results

Case Series: Subjects participating in this study were patients requiring hospital admission for COVID-19 diagnosed by PCR and provided informed written consent to receive intravenous RA as described in NCT04606069. RA was infused for 30 min at a rate of 5 µg/kg/h and then for 6 h at a rate of 1.44 µg/kg/h. The steady-state plasma level after infusion for 6 hours of 1.44 µg/kg/h was about 2 ng/ml in a prior sickle cell disease trial (MARKOVIC et al., Front Med (Lausanne), (2021), 8:749569). By comparison, RA administered as a 400 µg bolus over 10 seconds for myocardial perfusion imaging results in a peak plasma level of about 15 ng/ml (FIELD et al., Blood, (2013), 121:3329-3334). The slow RA infusion rate used in the current study avoided unpleasant side effects such as chest pain, dizziness, headache, flushing, nausea, and dyspnea that are routinely observed during myocardial perfusion imaging (MOLES et al., J Nucl Cardiol, (2018), 25: 820-827).

Figure 8:
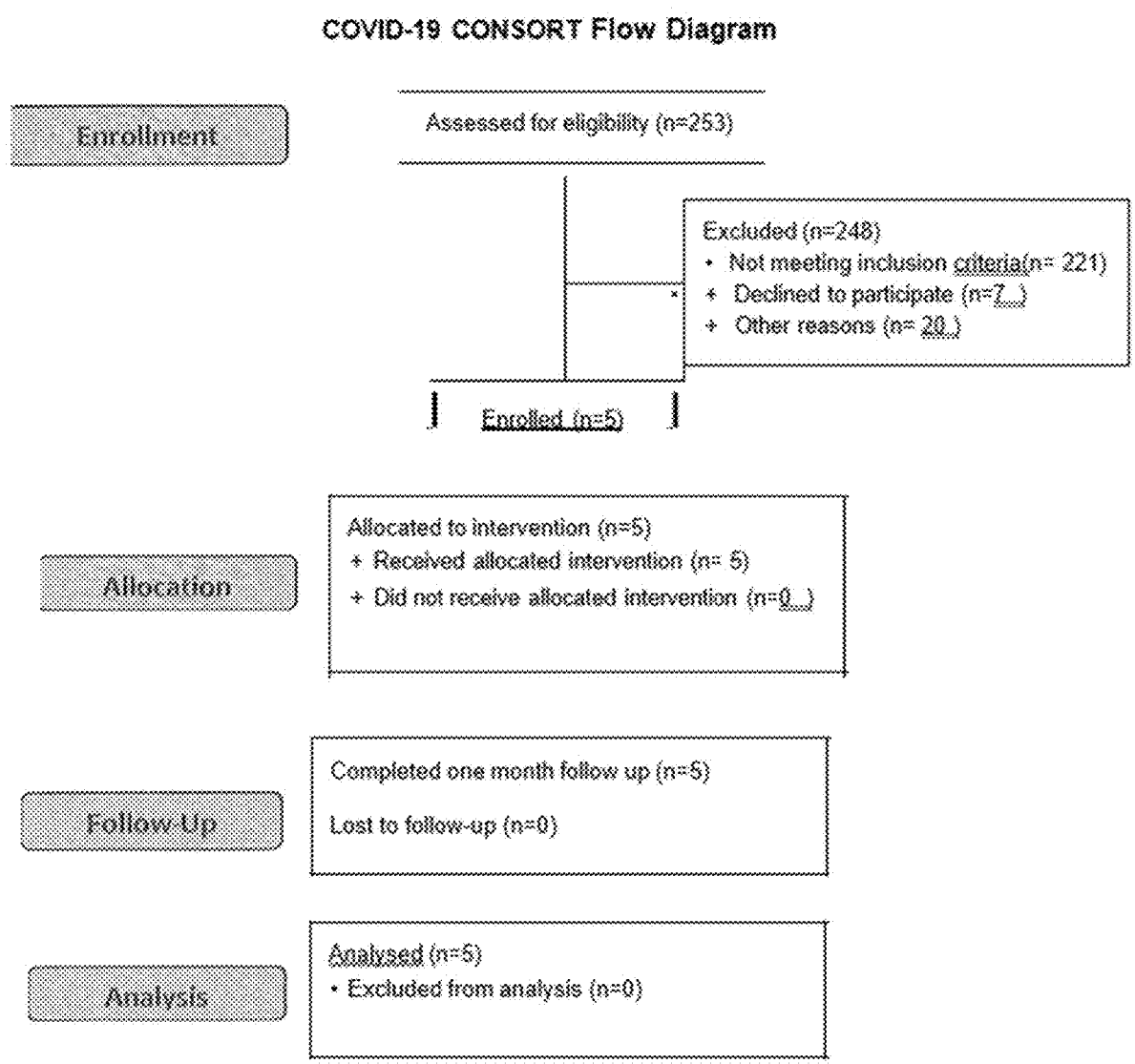
FIG. 8. Subject Flow through the first cohort of the study.

The 5 subjects enrolled in this study were all unvaccinated and classified as WHO stages 4-5 (FELSENSTEIN et al., Clin Immunol, (2021), 232: 108849). They were given supplemental oxygen based on clinical status, but none required intubation. All 5 patients were on room air when discharged. Upon diagnosis of COVID-19, all patients received 6 mg daily dexamethasone as standard of care. RA was administered within 3 hours of consent. There was 1 case of transient self-limiting nausea, but no other toxicities or reportable side effects of RA were noted during infusion or 30 days of follow-up. FIG. 8 summarizes subject enrollment, allocation, follow-up, and analysis. Eligibility criteria are listed in the supplemental methods.

Figure 9:
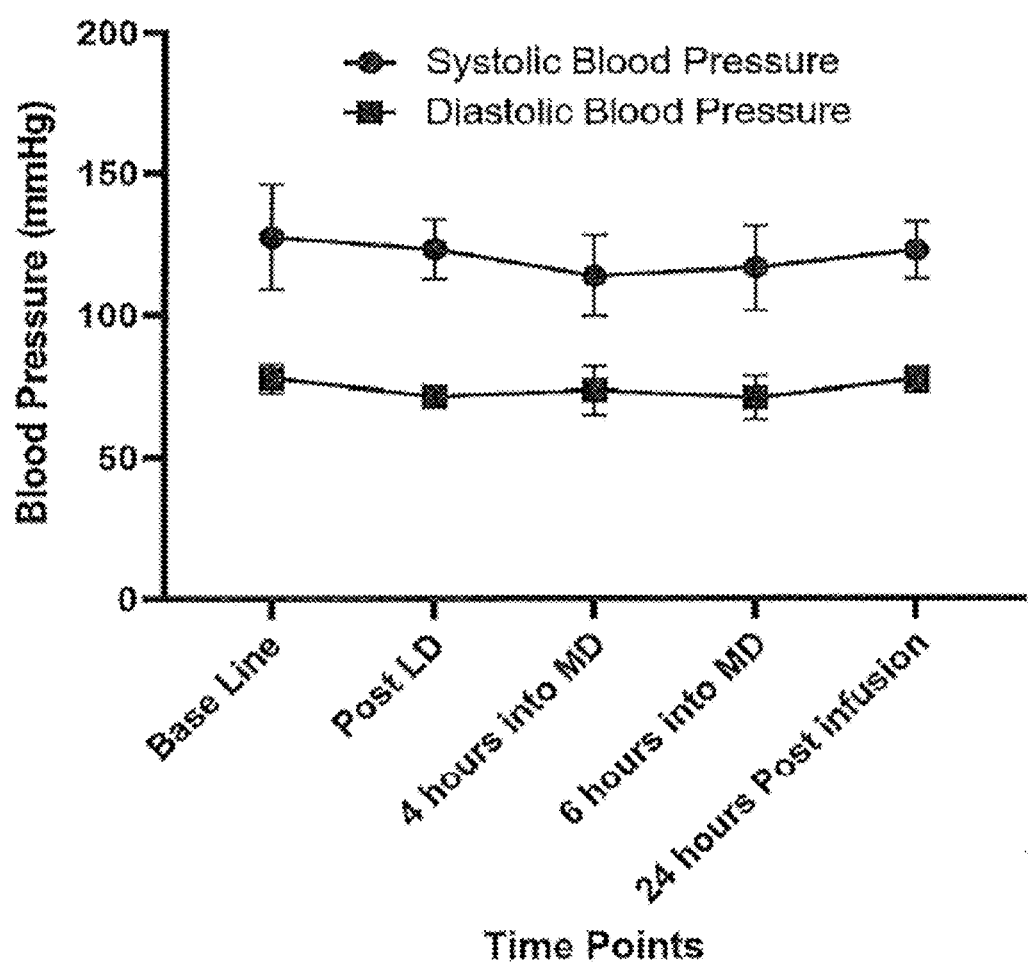
FIG. 9. Changes of blood pressure prior, during and post Regadenoson (RA) infusion. LD: Loading dose, 5 µg/kg over 30 minutes. MD: Maintenance dose, 1.44 µg/kg/hour for 6 hours. Data shown are means±SD values from 5 RA treated COVID-19 patients. Two-way ANOVA analysis show no significant changes during and post RA infusion (, n=5, P>0.05).

Although RA can produce vasodilation mediated by $A_{2A}Rs$ on vascular smooth muscle, at the dose used in this study blood pressure remain stable as illustrated in FIG. 9.

Case 1: A 60-year-old obese male [body mass index (BMI), 43.7] with a history of hypertension and gastric reflux presented with 4-days of chest pain and shortness of breath. On admission, oxygen saturation (SpO2) was 90% and chest x-ray demonstrated patchy opacities/consolidation at the bases. The patient received standard of care treatments including Remdesivir and dexamethasone with 2 liters/min supplemental 02 (WHO stage 4). He was successfully treated with RA one day after admission and reported rapid subjective symptomatic improvement. 02 support was reduced to 1 liter NC 2 days later and the patient was discharged on day 6.

Case 2: A 46-year-old obese female (BMI 36.3) with a history of hiatal hernia and diverticulitis, presented with a 10-day history of symptoms including shortness of breath with cough, and later with nausea and vomiting. Prior to admission, the patient received steroids and non-standard treatment with Albuterol, Azithromycin, and lvermectin. On admission, the patient was febrile (39.4° C.) and hypoxic (SpO2 85%). She received standard treatments including dexamethasone and 2 liters/min of 02 support (WHO stage 4). The patient was successfully treated with RA one day after admission and reported rapid subjective symptomatic improvement. 02 support was reduced to 1 liter within 2 days and the patient was discharged on day 6.

Case 3: A 37-year-old obese male (BMI 40.2) with no other medical history presented after 7 days of shortness of breath on exertion that limited his physical activity. On admission the patient was hypoxic with a SpO2 of 88% and his chest x-ray demonstrated right lower lobe opacities. He received standard treatments including Remdesivir and dexamethasone with 2 liters/min of 02 support. The patient was successfully treated with RA on the day of admission. After the RA infusion, his SpO2 increased to 97%, while his oxygen supplementation was weaned off with symptomatic improvement the following day. The patient was discharged on day 3.

Case 4: A 65-year-old male (BMI 29.2) with a remote smoking history presented with persistent symptoms of shortness of breath after outpatient treatment with monoclonal antibodies. On admission the patient was hypoxic with a SpO2 of 87%. His chest x-ray showed bilateral patchy opacities with mild to moderate pulmonary edema while a chest CT demonstrated peripheral ground glass opacities with destructive changes of the dependent parenchyma, consistent with COVID-19 pneumonia. He received treatment including a JAK inhibitor and dexamethasone while also requiring 40 L/minute high flow nasal cannula (NC) with a FiO2 of 60% (WHO stage 5) and admission to the medical intensive care unit (MICU). The patient was successfully treated with RA after admission with rapidly improved SpO2 by completion of the infusion. The patient was transferred out of MICU on day 3, weaned down to NC support by day 7 and discharged on day 9.

Case 5: A 58-year-old male (BMI 28.19) with a history of gastric reflux presented with persistent cough, shortness of breath, and acute hypoxia. His SpO2 was 88% on admission and he was placed on 6 liters/minute of 02 via nasal cannula (WHO stage 4). His chest x-ray was positive for multifocal patchy opacities with low lung volumes, while a chest CT demonstrated widespread peripheral ground glass opacities, consistent with COVID-19 pneumonia. He was out of the window for remdesivir, but received dexamethasone and continued oxygen supplementation. The patient received RA infusion and his SpO2 improved during treatment. He reported a self-limiting episode of nausea that resolved after treatment was complete. The patient was discharged on day 9. Evidence that RA Treatment Improves Oxygen Saturation, CRP, and D dimer.

Figure 10:
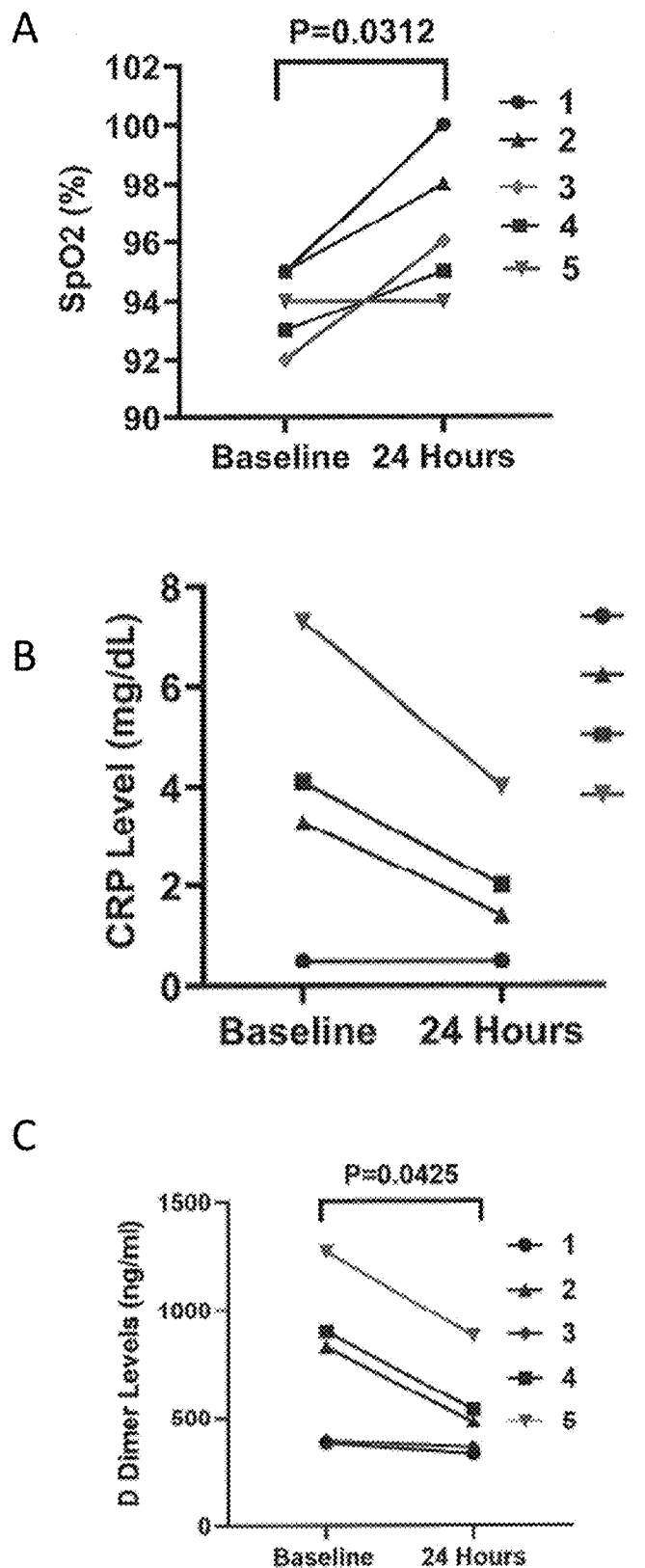
FIG. 10. Effects of regadenoson (RA) infusion of oxygen saturation and C-reactive protein (CRP) levels in plasma of COVID-19 patients. (A) SpO2 was determined by pulse oximetry just prior to and 24 hours after the initiation of 6.5 hours of RA infusion. There was a statistically significant difference in in SpO2 based on paired T-test (N=5). (B) Paired T-test of CRP prior and post RA infusion. P=0.075 (n=4). (C) Paired T-test of D dimer prior and post RA infusion. P=0.0425 (n=5).

Oxygen saturation (SpO2) was measured in all 5 subjects using pulse oximetry and was recorded at pre-admission (without oxygen supplementation), after admission (after starting oxygen supplementation), and periodically before, during and after RA infusion. Upon admission nasal cannula oxygen supplementation increased SpO2 compared to pre-admission (90±3.6 vs 95.5±1.7, P=0.002). SpO2 was significantly further elevated at 24 hours post RA infusion P=0.031 (FIG. 10A). CRP levels were reduced by >50% in 3 of 4 patients (measured only in 4 of 5 patients) 24 hours after RA infusion (P=0.075) (FIG. 10B). D dimer levels were significantly decreased at 24 hours post RA infusion P=0.043 (FIG. 10C).

Invariant NKT Cells are Influenced by Covid-19 and RA

Figure 11:
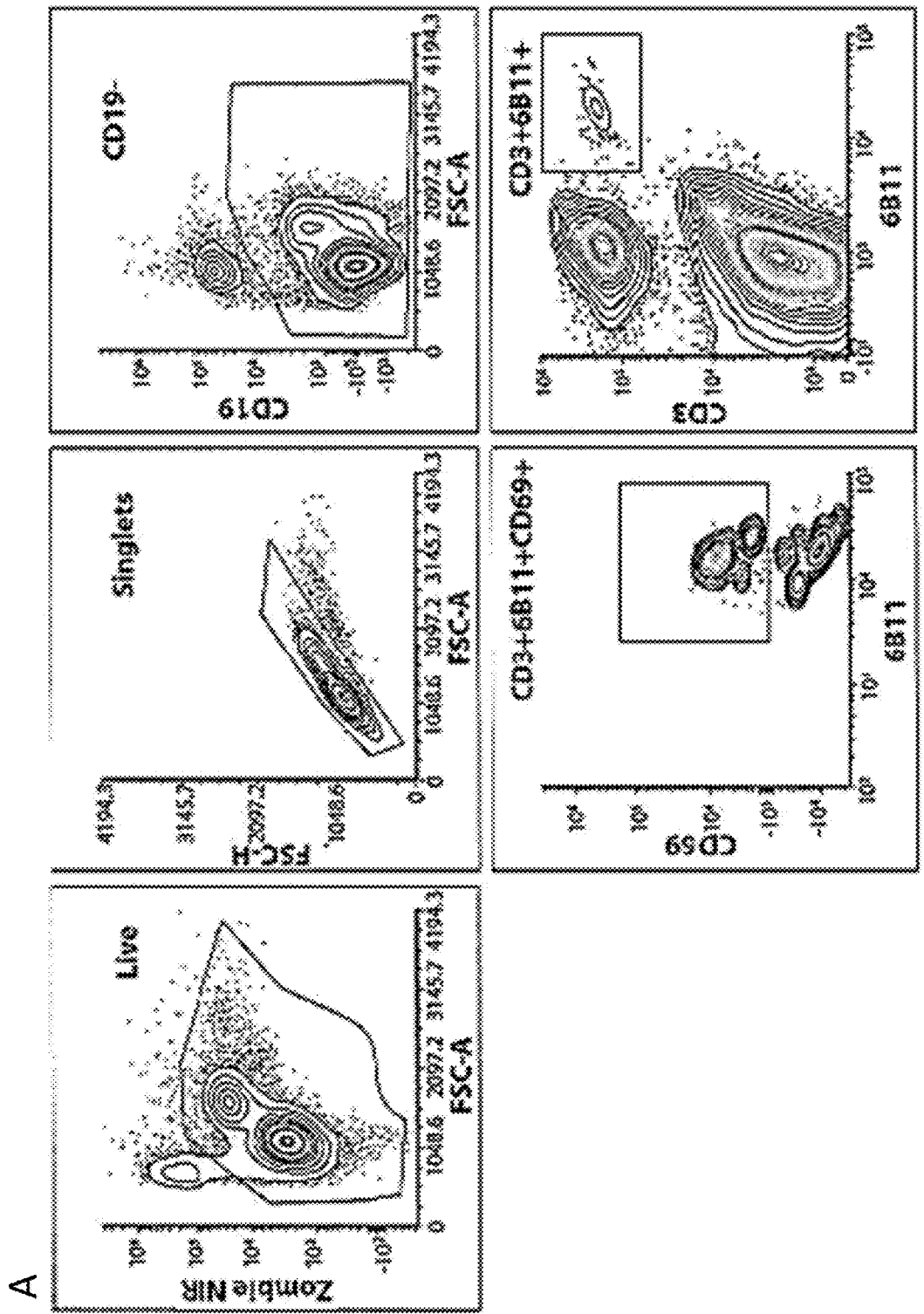
FIG. 11. Decrease in circulating iNKT cell activation during Regadenoson (RA) infusion into patients with COVID-19. (A) Flow cytometry gating strategy used to identify CD3+6B11+iNKT cells and their activation-state based on CD69 expression. (B) Comparison of percentages of CD69+CD3+6B 11-conventional T cells and CD69+6B 11+iNKT cells at baseline and 30 minutes into RA infusion. (C) Changes in the activation state of iNKT cells in blood of COVID 19 patients before, during and after RA infusion. PBMCs prepared from blood samples of 5 subjects were thawed and analyzed by flow cytometry at the same time. The color scheme used in 11B and 11C denotes the same individuals as shown in FIG. 10A.

Cytokine storm syndrome is characterized by elevated levels of proinflammatory cytokines, including IFN-γ, TNFα, and IL-17 (CHEN et al., J Clin Invest, (2020), 130:

2620-2629; MCGONAGLE et al., Autoimmun Rev, (2020), 19:102537). Alarmins such as IL-33 are tissue-derived nuclear proteins constitutively expressed at high levels in epithelial and endothelial barrier tissues. IL-33 released from damaged epithelial cells may be important for initiating cytokine storm since it is elevated in COVID-19 patients and can activate iNKT cells (MARKOVIC et al., Front Med (Lausanne), (2021), 8:749569). As shown in FIG. 11A, we identify rare iNKT cells (comprising 1% of all CD3+ T cells) by flow cytometry and identify an activated CD69+ subset. We confirm that iNKT cells, ut not conventional T cells of COVID-19 patients are mostly CD69+ (FIG. 11B). Moreover, the data show for the first time that RA treatment reduces the fraction of circulating iNKT cells that are CD69+ by 50% within 30 minutes (FIG. 11C). These findings suggest that cytokine storm in COVID-19 is initiated in part by the release of IL-33 and possibly other alarmins from infected epithelial cells and triggers iNKT cell activation.

Figure 12:
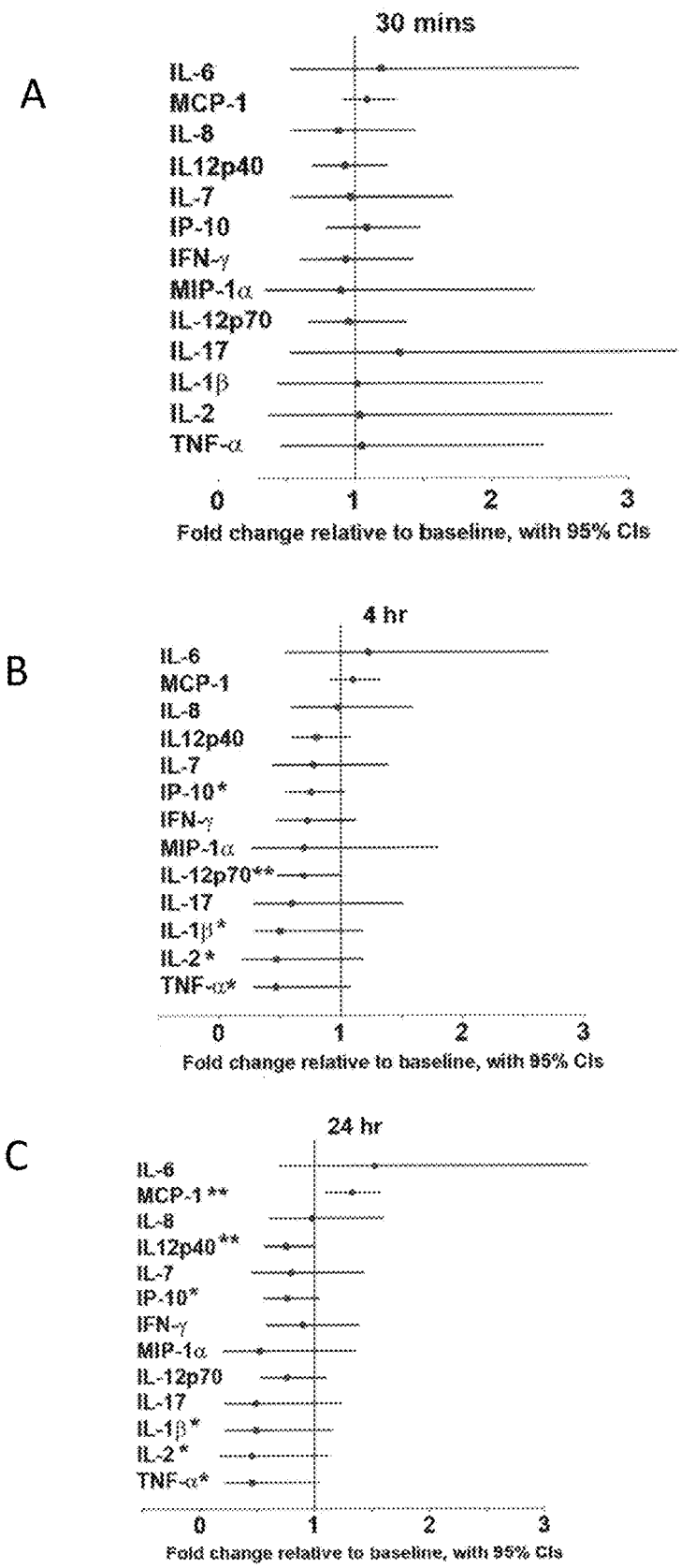
FIG. 12. Changes of plasma proinflammatory cytokines/chemokines during and post RA infusion compared to the baseline (prior to RA infusion). Cytokine levels were normalized to baseline. Cytokine levels below and above baseline values are depicted by green and red, respectively. Blood was collected before RA infusion (baseline) and 3 times after the start of infusion: (A) at the end of loading dose (5 µg/kg/hour, 30 minutes), (8) 4 hours into the maintenance dose (1.44 µg/kg/hour, 4.5 hours) and (C) 24 hours post RA infusion (24 hours), N=5. Green dots and lines indicate cytokine levels lower than baseline, *P<0.1; **P 0.05 relative to baseline by the Paired T-Tests.

A reduction in the activation of iNKT cells is expected to reduce the production of proinflammatory cytokines produced by other cells. We compared the ratio over baseline of plasma cytokines at 30 minutes, 4.5 h, and 24 hours after the start of RA infusion (FIG. 12). RA had very little effect on the levels of 13 pro-inflammatory cytokines at 30 minutes, but 11 of 13 were reduced at 4.5 hours. A similar pattern was seen at 24 h. The data are consistent with the possibility that iNKT activation occurs rapidly after lung injury and precedes changes in the levels of plasma cytokines.

Figure 13:
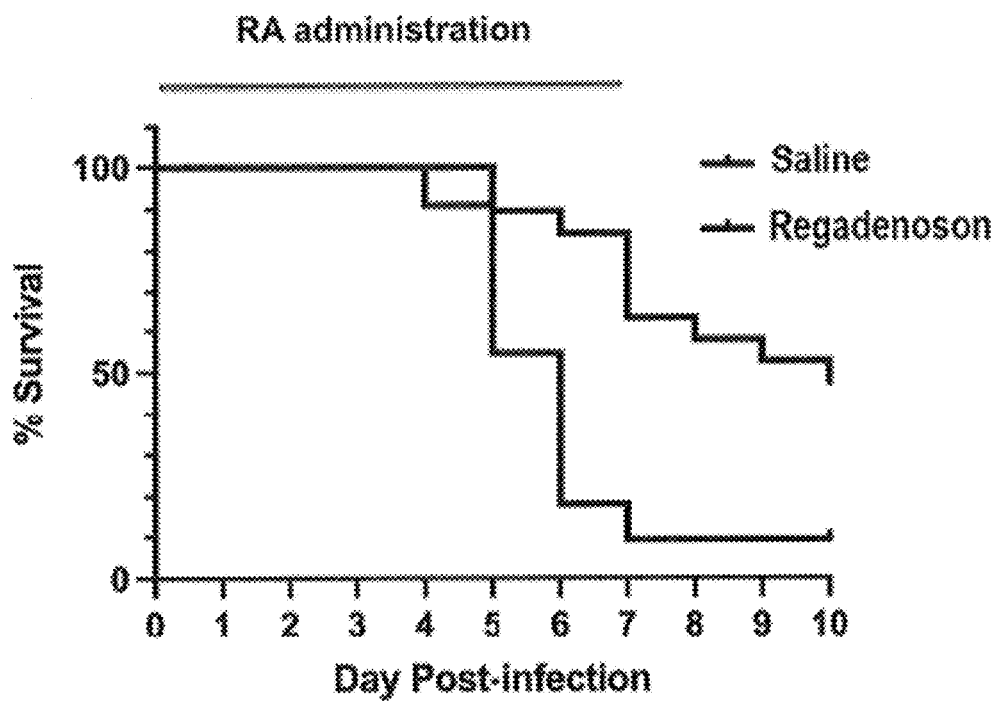
FIG. 13. Regadenoson increases survival of COVID-19-infected K18-ACE2 mice. Seven day 0.5 µl/h Alzet pumps loaded with 80 µg/ml Regadenoson (N=19), or saline (N=11) were implanted subcutaneously into 2-3-month-old B6.Cg-Tg(K18-ACE2)$_2$Prlmn/J mice just prior to infection with 1250 Pfu of Hong Kong VM20001061/2020. Mice were euthanized based on criteria described in Methods. Data are combined from three independent experiments. Survival curves are statistically different based on the Log rank Mantel Cox test, P<0.001. The time of RA infusion is indicated by a horizontal bar.

Treatment with regadenoson increases survival of SARS-CoV-2-infected mice The current pilot study was not sufficiently powered to determine if RA reduces mortality in hospitalized COVID-19 patients. Therefore, we tested the effects of RA on survival using a SARS-CoV-2 infected mouse model (SUN et al., Cell Host Microbe, (2020), 28:124-133.e124). Thirty mice infected SARS-CoV-2 were treated by subcutaneous infusion with regadenoson (1.44 µg/kg/hr) and 11 controls were infused with saline. As shown in FIG. 13 over 90% of control mice died by day 10, mostly on days 4-5 after infection. Only 50% of RA treated mice died, mostly on day 7, which corresponds with when RA treatment stopped. This shows that RA infusion decreases mortality in COVID-19-infected mice and suggests that longer treatment may produce even better protection.

Discussion

For this case series we infused RA into the first five COVID-19 patients enrolled in an NHLBI sponsored Clinical Trial (NCT0460606) to evaluate the safety and efficacy of this therapeutic candidate. This is the first examination of administering a selective A2AR agonist in COVID-19 patients. We restricted this initial study to moderately ill patients as characterized by lower respiratory disease based on clinical assessment or imaging and low flow (WHO stage 4) or high flow (WHO stage 5) supplemental oxygen administered by mask or nasal cannula. No intubated patients (WHO stages 6-7) were enrolled in this study.

Adenosine is produced by hypoxic or ischemic tissues and has been found to have vasodilatory, anti-platelet and broadly anti-inflammatory effects that are mostly mediated by the $A_2AR$. Regadenoson is a selective $A_{2A}R$ agonist, used as a coronary vasodilator for myocardial perfusion imaging. RA is rapidly administered by IV injection of 400 µg over 10 seconds and frequently produces side effects. Most AEs that occur as a result of bolus injection of Lexiscan begin soon after dosing and resolve within 15 minutes, except for headache, which resolved in most patients within 30 minutes. We have reported previously that RA is also safe and devoid of side effects during infusion at 1.44 µg/kg/h for 24-48 h for treating sickle cell crisis and lung transplantation (FIELD et al., Blood Adv, (2017), 1:1645-1649; LAU et al., J Heart Lung Transplant, (2020), 39: 563-570).

Of the 5 Covid-19 patients treated with RA only one experienced a mild side effect, transient nausea, that was self-limiting. We conclude that RA is safe to use in moderately ill COVID-19 patients. We show that similar dosing of RA to K18-hACE2 transgenic mice that are susceptible to Covid-19 causes significantly reduced mortality. This human study did not include untreated patient controls or have sufficient power to determine if RA reduced mortality or length of stay in the hospital, but we did observe promising effects within 24 hours of RA treatment: subjective improvement in all subjects; increased SpO2; decreased D dimer, a trend toward lower CRP levels; rapidly reduced expression of CD69 on circulating iNKT cells; and a gradual reduction in circulating levels of 11 of 13 pro-inflammatory cytokines. A larger placebo-controlled clinical trial is needed to confirm these findings, but they do suggest that RA will be effective for rapidly reducing cytokine production in inflamed COVID-19 patients.

In previous animal studies the administration of $A_{2A}R$ agonists was found to reduce IRI in liver, and lung (LAU et al., J Heart Lung Transplant, (2020), 39: 563-570; LAPPAS et al., J Exp Med, (2006), 203:2639-2648; STONE et al., Transplantation, (2015), 99:2494-2503). Although $A_{2A}R$ activation produces anti-inflammatory responses in neutrophils, macrophages, T cells and platelets, the cell that appears to be most important for suppressing an inflammatory cascade is the iNKT cell (LIN et al., PLoS One, (2013), 8: e74664; WALLACE et al., Blood, (2010), 116:5010-5020). The activation of iNKT cells is probably mediated in part by host lipid mediators or alarmins such as IL-33 are rapidly produced in epithelial cells due to tissue ischemia (FERHAT et al., Front Immunol, (2018), 9:2308).

Proinflammatory cytokine transcription is stimulated in iNKT cells in response to NF-KB activation. $A_{2A}R$ transcription also is stimulated in response to NF-KB activation as a counter-inflammatory response, albeit at a slower rate (LIN et al., PLoS One, (2013), 8:e74664). Over time after tissue injury, $A_{2A}R$ expression and signaling become more effective at suppressing the activation of iNKT cells and other leukocytes. The early activation marker CD69 is elevated on iNKT cells of COVID-19 patients at the time of admission and correlates with hypoxia and poor patient outcome (JOUAN et al., J Exp Med, (2020), 217). Other treatments that might be expected to reduce cytokine storm in COVID-19 patients are anti-iNKT or anti-CD 1d antibodies to deplete iNKT cells or block their activation, respectively (FIELD et al., PLoS One, (2017), 12:e0171067; SHEN et al., Eur J Immunol, (2015), 45:612-623).

As previously noted by Correale et al. adenosine may be particularly effective in COVID-19 subjects receiving supplemental oxygen because iatrogenic hyperoxia reduces endogenous extracellular adenosine production (CORREALE et al., PLoS One, (2020), 15: e0239692). Moreover hyperoxia may inhibit the induction of $A_{2A}Rs$ in iNKT cells, T cells, and macrophages (MURPHREE et al., Biochem J, (2005), 391:575-580; LIN et al., PLoS One, (2013), 8: e74664.; LAPPAS et al., J Immunol, (2005), 174: 1073-1080). Other factors that may reduce adenosine production and signaling in the hyperoxic lung are reduced transcription of the ecto-enzymes CD39 and CD73 and inactivation of PANX1 channels that release ATP (SYNNESTVEDT et al., J Clin Invest, (2002), 110: 993-1002; ELTZSCHIG et al., Blood, (2009), 113:224-232; KIRBY et al., Am J Physiol Heart Gire Physiol, (2021), 320: H1055-H1065; SANDILOS et al., J Biol Chem, (2012), 287: 11303-11311). These observations suggest that hyperoxia will suppress adenosine production and signaling due to several factors that may be counteracted by RA infusion.

In the current study RA was administered by IV infusion and gained access to blood and peripheral tissues. In a prior study, Correale et al. treated fourteen hospitalized COVID-19 patients with inhaled adenosine (9 mg over 5 minutes) twice on day 1 and once daily for 4 more days (CORREALE et al., PLoS One, (2020), 15: e0239692). Despite its short half-life adenosine-treated patients exhibited a significant increase in PaO2/FiO and the death rate was 1/14 (7%) in the adenosine group and 11/52 (21%) in the control group. Beneficial effects of inhaled adenosine were also reported in a subsequent two patient case study (SPIESS et al., Front Pharmacol, (2021),12:676577). Inhaled adenosine appeared to be metabolized rapidly and without accumulation in blood. IV adenosine produces transient heart-block that is not seen when adenosine is inhaled (NAGELHOUT et al., AANA J, (1992), 60:287-292). Heart-block is mediated by the A1R that is weakly activated by RA. Compared to inhaled adenosine which has a short half-life, RA has a terminal half-life of 2 hours, is distributed throughout the body and likely produces generalized anti-inflammatory effects.

Published data showed that D dimer levels were elevated in COVID-19 patients (ROSTAMI et al., Expert Rev Hematol, (2020), 13:1265-1275). The levels of D dimer were shown to be highly correlated with unfavorable outcomes (ZHOU et al., Lancet, (2020), 395: 1054-1062). Plasma d-dimer in COVID-19 patients in intensive care and the direct link with development of pulmonary embolism and vascular thrombotic complications (OUDKERK et al., Radiology, (2020), 297: E216-e222; KLOK F A et al., Thromb Res, (2020), 191: 145-147). In this report, we showed that RA infusion significantly reduced D dimer levels in COVID-19 patients. This finding indicate that RA may has additional anti-coagulation effects in COVID-19 patients.

Conclusion

Oxygen supplementation in COVID-19 patients may cause an iatrogenic reduction in the release of adenine nucleotides into the extracellular space, a reduction in the rate of ATP conversion to adenosine by ecto-enzymes, and a reduction in the expression of $A_{2A}Rs$ on iNKT cells and other leukocytes. These considerations provide a rationale for administering RA or other $A_{2A}R$ agonists during oxygen supplementation. We confirmed that iNKT cells are highly activated in COVID-19 patients, and we show for the first time that their activation is rapidly reduced in response to RA infusion ahead of a reduction in circulating proinflammatory cytokines. The findings support further evaluation of RA or other $A_{2A}R$ agonists for treatment of COVID-19 patients and other cases of lung inflammation—particularly in the setting of supplemental oxygen.

Example 4. Use of Regadenoson to Reduce Systemic Inflammation Post Lung Transplantation This trial was primarily designed as a Phase I safety, dose-escalating, and feasibility study that would allow an optimal infusion dose to be determined based on dose-limiting toxicities identified in lung transplant recipients.

Dose Alteration

The rational for dose selection was published in our previous publication (LAU et al., J Heart Lung Transplant, (2020), 39:563-570. We enrolled 4 additional lung transplantation patients that were treated with regadenoson at 1.44 ug/kg/hour for 12 hours. Our previous publication, infusion of regadenoson (1.44 ug/kg/hour for 12 hours) was safe in 10 lung transplantation patients. In the lung transplantation population, the median peak plasma levels of regadenoson infused were 1.68 ng/ml (range 1.2 to 1.9 ng/ml). Based on this preliminary result, we modified our protocol to a high dose infusion at the 2.88 ug/kg/hour for 12 hours in the last three lung transplantation recipients. FDA, NIH/NHLBI designated DSMB and institutional IRB approved our modification. The regadenoson infusion started at the time of skin incision, continued throughout the transplant procedure and into the immediate postoperative period for a total duration of 12 hours. Enrollment of bilateral lung transplant control patients Even though this phase I trial was designed to determine the dose of regadenoson infusion that is safe and optimal for use in human lung transplant recipients, we tried to evaluate its potential anti-inflammatory effects in these patients. To comprehensively evaluate the clinical outcomes and levels of molecular markers (cytokines/chemokines), which is related to IR injury/PGD severity post lung transplantation, we recruited 6 bilateral lung transplant control recipients in our current study.

Clinical End-Points and Clinical Monitoring

Primary end-points included dose-limiting toxicities and 30-day mortality. Secondary outcomes included PGD scores evaluated at 24, 48, and 72 hours, ICU length of stay, hospital length of stay, need for post-transplant extracorporeal membrane oxygenation, duration of mechanical ventilation post-operatively, and 12-month survival. Clinical parameters including blood pressure, heart rate, mean arterial pressure, pulmonary arterial pressure, were monitored and collected. Continuous variables are listed as mean and standard deviation, whereas categorical variables are presented as counts.

Measurement of Plasma Levels of Regadenoson

The peripheral blood samples for regadenoson measurement were collected at the following timepoints: 1) Prior to 1st lung reperfusion; 2) 1 hour post 1st lung perfusion; 3) 6 hours post infusion start; 4) 12 hours post infusion start; 5) 24 hours post infusion start. The blood samples were centrifuged, and the plasma samples were collected and stored at $-80°$ C. The levels of regadenoson were determined via liquid chromatography-mass spectrometry with an improved d protocol based on our previous publication (LAU et al., J Heart Lung Transplant, (2020), 39:563-570) at The Mass Spectrometry Center at the School of Pharmacy, University of Maryland, Baltimore (detailed in supplemental methods).

Measurement of Cytokines/Chemokines

Blood was drawn for cytokine/chemokine, damage associated molecular patterns (DAMPs) at the following different timepoints: 1) before infusion (baseline), 2) 15 minutes before reperfusion of the 1st lung, 3) 30 minutes after reperfusion of 1st lung, 4) 30 minutes after reperfusion of 2nd lung, and 5) 6 hours after reperfusion of 1st lung.

The cytokines/chemokines, HMGB1 and sRAGE were determined at The University of Virginia Flow Cytometry Core (RRID: SCR 017829) as previously described (LAU et al., J Heart Lung Transplant, (2020), 39:563-570). The customized 11-plex cytokine panel detects IL-1, IL-2, IL-6, IL-7, IL-8, IL-10, IL-12P40, IL-12P70, IL-17, TNFa, and IFN-γ (Millipore Sigma, Burlington, MA).

Statistical Analysis

Statistical differences of cytokine/chemokines, heart rates and blood pressures between groups were determined by two-way ANOVA followed by Tukey's multiple comparison test (GraphPad Prism 9.0). The PGD scores were analyzed by chi-squared test. The intubation times and hospital LOS, ICU LOS were analyzed by ANOVA of log and Kruskal-Wallis. Data was reported as means±SD. P value equal or less than 0.05 was considered significant.

Results Regadenoson treatment improve clinical outcomes post lung transplantation We enrolled 21 regadenoson treated lung transplant patients and 7 control transplant patients (without regadenoson infusion) in the current trial.

To evaluate the potential efficacy of regadenoson in lung transplant recipients, various data related to clinical outcomes were collected and analyzed before, during and after regadenoson infusion. The PGD scores of regadenoson (1.44 ug/kg/h) treated patients were significantly improved at 24 hours post transplantation when compared with control patients [p=0.024 for comparing PGD=0 and PGD 1]. The PGD scores of regadenoson (both 1.44 and 2.88 ug/kg/h groups) treated patients were also improved when compared with control patients but did not reach significance due to the limited number of enrolled subjects at 24 hours, 48 and 72 hours.

Regadenoson infusion also trended to decrease the intubation time when compared with control patients, but not reaching statistical significance due to limited numbers of enrolled subjects. The hospital length of stay (LOS) and ICU LOS were reduced, but not significantly altered by regadenoson treatment. The total ischemic times had no significant differences among the two regadenoson infused groups and control patients.

Hemodynamic Effects of Regadenoson Infusion in Lung Transplant Recipients

Regadenoson is used as a pharmacologic coronary vasodilator to induce maximum myocardial hyperemia in myocardial perfusion imaging (MPI) (MEKKAOUI et al., JACC Cardiovasc Imaging, (2009), 2:1198-1208; BUHR et al., Vasc Health Risk Manag, (2008), 4:337-340). It was used as a single bolus (400 ug over 10 seconds) infusion in MPI and may cause undesirable side effects (PALANI et al., Cardiol Rev, (2013), 21:42-48). Because regadenoson cause a hemodynamic response, we monitored and collected systolic and diastolic blood pressure, heart rate, mean arterial pressure and pulmonary arterial pressure during regadenoson infusion in this study. Regadenoson infusions did not significantly alter blood pressure (both systolic and diastolic, FIGS. 14A & 14B), heart rate (FIG. 15A), mean arterial pressure (FIG. 15B) and pulmonary arterial pressure ($P>0.05$, data not shown).

Regadenoson Infusion Altered Cytokines/Chemokines

Since IR cause inflammatory/immune cells infiltration and activation (4-7) which results in releasing of various of cytokines/chemokines (SMAIL et al., Exp Lung Res, (2016), 42:131-141; FMD1K 0 et al., Rev Assoc Med Bras (1992), (2019), 65:1193-1200; ZHAO et al., Am J Physiol Lung Cell Mol Physiol, (2011), 300: L718-729; YANG et al., Cell Biochem Biophys, (2014), 70: 1527-1532). The later lead damage to lung (SHARMA et al., Am J Physiol Lung Cell Mol Physiol, (2018), 315:L301-1312; SHARMA et al., Am J Physiol Lung Cell Mol Physiol, (2007), 293: L105-113; CHU et al., Front Pharmacol, (2021),12:752507; SAADAT et al., Respir Res, (2019), 20: 96). We revealed that regadenoson infusion significantly inhibited transplantation-induced plasma levels of IL-6 at 30 minutes after reperfusion of 2nd lung (control vs low dose, p=0.041; control vs high dose, p=0.007, FIG. 19A). Low dose regadenoson infusion also significantly reduced levels of IL-8 at 30 minutes after reperfusion of 2nd lung (p=0.032, FIG. 19B). Regadenoson trended toward reducing transplant-induced elevation of TNF-α at 30 minutes after reperfusion of 1st lung (control vs low dose, p=0.071; control vs high dose, p=0.154 FIG. 16A). In addition, low dose infusion trended toward increasing IL-10 (p=0.078 FIG. 16B), a well-known anti-inflammatory cytokine (26).

Regadenoson Treatment Significantly Reduced Plasma Levels of sRAGE

HMGB 1 and RAGE mediated lung IRI in previous reports (ALI et al., Ann Thorac Surg, (2012), 93:282-288; SHARMA et al., Am J Transplant, (2013), 13:2255-2267; STONE et al., Respir Res, (2017), 18:212; LI et al., Dose Response, (2020), 18:1559325820969340). sRAGE is associated with PGD status post lung transplantation may serve as a biomarker for early PGD diagnosis (CHRISTIE et al., Am J Respir Crit Care Med, (2009), 180:1010-1015; DIAMOND et al., Transplantation, (2017), 101:21-22; SHAH et al., J Heart Lung Transplant, (2012), 31:942-949; POTTECHER et al., Transplantation, (2017), 101:112-121). We measured plasma levels of HMGB1 and sRAGE in the regadenoson-treated and control plasma samples. The results showed that Regadenoson infusion significantly diminished transplantation-induced plasma levels of sRAGE at 30 minutes post the 1st lung reperfusion in low-dose treated group (n=14), and at 30 minutes post the 2nd lung reperfusion in both low- and high-dose treated groups (n=3, P<0.0001) when compared with saline infused control group (n=7, FIG. 20). The sRAGE level was decreased in trend (P=0.0656) at 30 minutes post the 1st lung reperfusion in the high dose treated group when compared with saline infused control group (n=7, FIG. 20). However, Regadenoson infusion had no significant effect on the plasma levels of HMGB-1 at any timepoints in these patients (P>0.05, data not shown).

Adverse Reactions in Regadenoson Lung Transplantation Trial

The side effects of regadenoson observed in the phase 3 clinical trials showed mild and transient in nature; none was life threatening or serious (A L JAROUDI et al., J Am Coll Cordial, (2009), 54:1123-1130). In our study, no drug related serious adverse events or dose limiting toxicities were observed in 14 low dose-treated and 3 high dose-treated lung transplantation recipients. The common side effects, including chest pain, dyspnea, flushing, headache, dizziness and neck/jaw pain was not observed in our study. A seizure was observed at the 36 hours post regadenoson infusion in one of the subjects. According to the drug blood levels, we measured in this study, the levels of regadenoson were minimal after 24 hours post regadenoson infusion. Therefore, this incidence may not directly relate to regadenoson infusion. The subject was receiving sedation for his anxiety, which was stopped prior to surgery.

The Plasma Levels of Regadenoson

Figure 17:
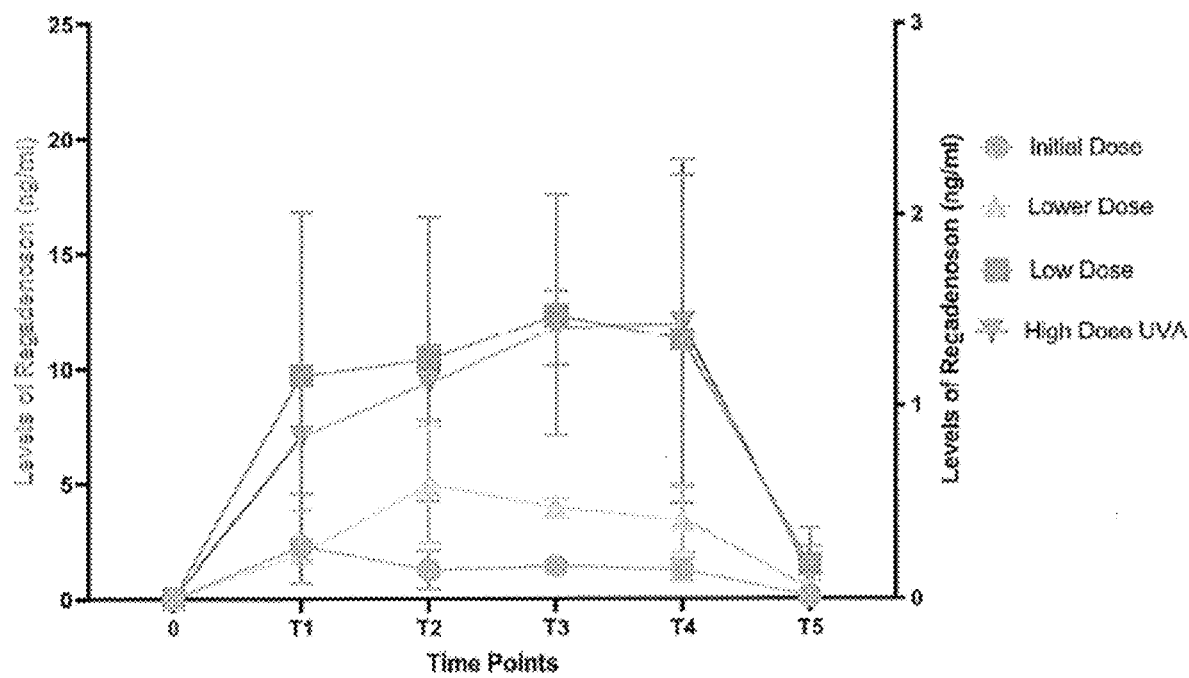
FIG. 17. Plasma levels of regadenoson at each of the 4 dose levels. The blood samples were collected and measured at the following timepoints: 0, Prior infusion; T1, Prior to 1st lung reperfusion; T2, 1 hour post 1st lung perfusion; T3, 6 hours post infusion start; T4, 12 hours post infusion start; TS, 24 hours post infusion start. Data shown are the mean±SD. The left Y axis showed the scales for high dose(2.88 ug/kg/hr); the right Y axis showed the scales for initial dose (0.24 ug/kg/hr), lower dose (0.60 ug/kg/hr), and low dose (1.44 ug/kg/hr).
Figure 18:
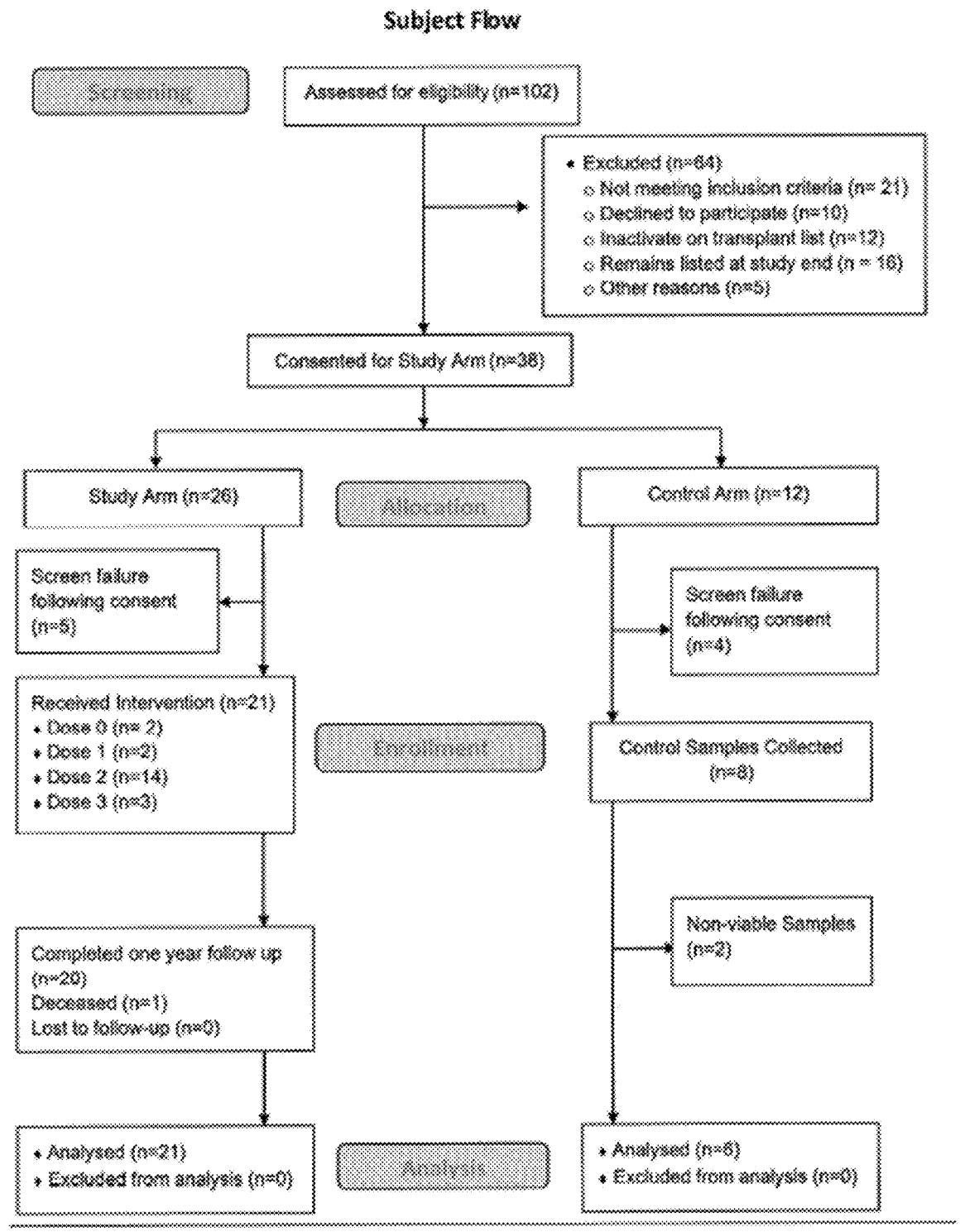
FIG. 18. Subject flow through the study.

We measure the plasma levels of regadenoson at various timepoints during and post drug infusion. The results showed that the peak drug level is at the 6 hours post infusion start in low dose group, while at 12 hours post infusion start in the high dose group. The median peak plasma levels of regadenoson infused at low dose were 1.30 ng/ml (range 0.72 to 3.01 ng/ml) in the low dose treated patients. The median peak plasma levels of regadenoson infused at high dose were 14.34 ng/ml (range 5.66 to 21.88 ng/ml, FIG. 17).

Discussion

The primary goal of the current phase I study is to determine the safety and feasibility of regadenoson in lung transplant recipients. Regadenoson is the first selective A2A receptor agonist that is approved by the FDA and is currently used as a pharmacologic coronary vasodilator to induce maximum myocardial hyperemia in MPI (MEKKAOUI et al., JACC Cardiovasc Imaging, (2009), 2:1198-1208; BUHR et al., Vasc Health Risk Manag, (2008), 4:337-340). It was used as a single bolus (400 ug over 10 seconds) infusion in MPI and may cause undesirable side effects, including chest pain, dyspnea, flushing, headache, dizziness, GI and neck/jaw pain (PALANI et al., Cardiol Rev, (2013), 21:42-48). Our recent published results showed that regadenoson is safe in 14 lung transplantation trial (LAU et al., J Heart Lung Transplant, (2020), 39:563-570). In this study, we infused regadenoson at 1.44 ug/kg/h for additional 4 lung transplantation recipients and at 2.88 ug/kg/h for 3 lung transplantation recipients. No drug related serious adverse events or dose limiting toxicities were observed in both 1.44 ug/kg/h and 2.88 ug/kg/h-treated groups. The common side effects (such as chest pain, dyspnea, flushing, headache, dizziness, and neck/jaw pain) in MPI studies were also absent in our current study. Since regadenoson was used as a vasodilator, its major side-effects are related to its hemodynamic effects. We found that both low dose and high dose infusions did not significantly alter systolic and diastolic blood pressure, heart rate, mean arterial pressure and pulmonary arterial pressure during and post regadenoson infusion in this study. Based on our current safety and feasibility data, we believe that regadenoson is safe and feasible to be infused at dose 1.44 ug/kg/hr and 2.88 ug/kg/hr. To confirm our current findings in the single center, small cohorts' study, a larger multiple-centered, double blinded phase II trial is needed.

Even though this phase I trial was designed to determine the dose of regadenoson infusion that is safe and optimal for use in human lung transplant recipients, we tried to evaluate its potential benefits on clinical outcomes and its anti-inflammatory effects in these limited patients. PGD is the most frequent cause of early mortality and prolonged intensive care units (ICU) stay following lung transplantation (MEYERS et al., J Thorac Cardiovasc Surg, (2005), 129: 1421-1429). PGD is also a main factor that contributing to BOS, which is the primary cause of mortality for recipients after 1 year of transplant (CHRISTIE et al., Chest, (2003), 124:1232-1241; DAUD et al., Am J Respir Crit Care Med, (2007), 175:507-513). Our results revealed that regadenoson infusion at 1.44 ug/kg/hr for 12 hours significantly reduced PGD score (p<0.05, Table 2). The PGD scores of regadenoson (the other 1.44 and 2.88 ug/kg/h groups) treated patients were also improved when compared with control patients, even if the statistics did not show significance due to the limited number of enrolled subjects at 24 hours, 48 and 72 hours. The intubation time is also shortened in the regadenoson treated groups when compared with control group (Table 5). These results indicate that regadenoson treatment may be beneficial for lung transplant recipients.

Figure 20:
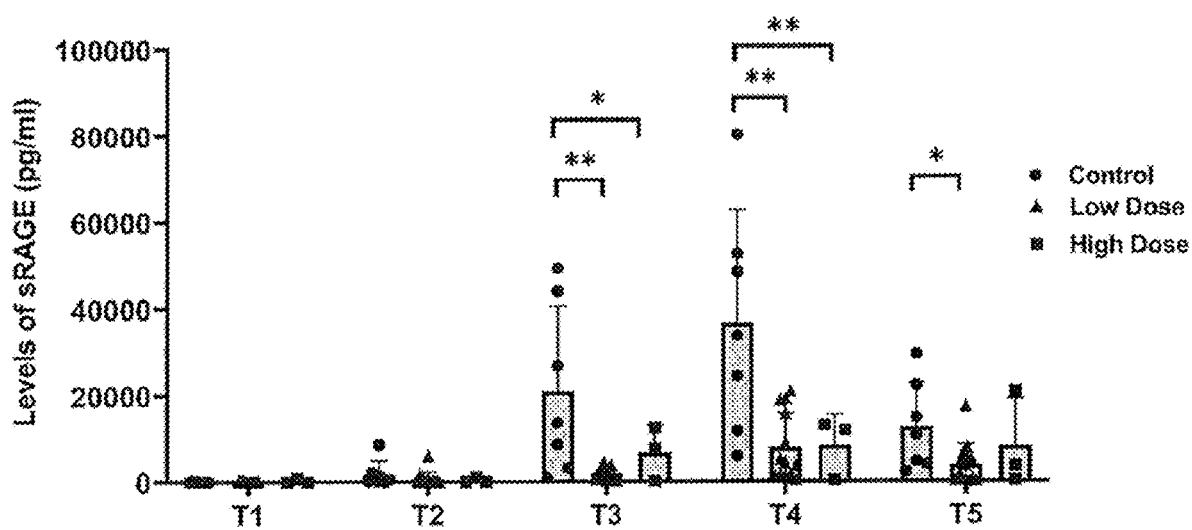
FIG. 20. Regadenoson infusion significantly reduced plasma levels of soluble receptor for advanced glycation end-products (sRAGE) in lung transplant recipients. Bar graphs show the plasma levels of sRAGE at the following indicated timepoints. T1, prior infusion (baseline); T2, 15 minutes before reperfusion of the 1$^{st}$ lung; T3, 30 minutes after reperfusion of 1st lung; T4, 30 minutes after reperfusion of 2nd lung; T5, 6 hours after reperfusion of 1st lung. Low dose, 1.44 ug/kg/hour, n=14; High dose, 2.88 ug/kg/hour, n=3; and Control, control lung transplant patients, n=7. Data shown are the mean±SD. *, P<0.1; **, P<0.0001.

PGD is caused by the pathologic acute inflammatory response to ischemia reperfusion (IR) injury, which induced releasing of various of proinflammatory cytokines/chemokines. These cytokines/chemokines can recruit more inflammatory/immune cell infiltration and activation in the allografts and cause damage to lung endothelial and epithelial cells (SHARMA et al., Am J Physiol Lung Cell Mol Physiol, (2018), 315:L301-1312; SHARMA et al., Am J Physiol Lung Cell Mol Physiol, (2007), 293:L105-113; CHU et al., Front Pharmacol, (2021),12:752507; SAADAT et al., Respir Res, (2019), 20: 96). $A_{2A}R$ activation reduced proinflammatory cytokine production in various disease models (LAPPAS et al., J Immunol, (2005), 174:1073-1080; LINDEN et al., Annu Rev Pharmacol Toxicol, (2001), 41: 775-787; OHTA et al., Nature, (2001), 414:916-920; SULLIVAN et al., J Immunol, (1990),145:1537-1544; SULLIVAN et al., Br J Pharmacol, (2001), 132:1017-1026). Accumulated publications have revealed that A2AR agonists attenuated lung IRI in murine IR models, porcine models and acute lung injury (SHARMA et al., Am J Respir Crit Care Med, (2016), 193:988-999; STONE et al., Transplantation, (2015) 99:2494-2503; LAPAR et al., J Thorac Cardiovasc Surg, (2011),142:887-894; EMAMINIA et al., Ann Thorac Surg, (2011), 92:1840-1846; FOLKESSON et al., Am J Physiol Lung Cell Mol Physiol, (2012), 303:L259-271; HE et al., Cell Signal, (2013), 25:1913-1923; HWANG et al., J Biochem Mol Toxicol, (2021), 35: e22635; LI et al., PLoS One, (2013), 8:e59257). In consistent with the above findings, we demonstrated that regadenoson infusion significantly reduced plasma levels of IL-6, IL-8 and sRAGE (FIGS. 19 & 20). Regadenoson treatment also trended to decrease levels of TNF-a (supplemental FIG. 19A). In addition, regadenoson infusion trended to elevate IL-10 (supplemental FIG. 38), the most studied anti-inflammatory cytokines. IL-10 inhibited inflammatory and T-cell mediated immune responses in lung transplantation (41) and acute lung injury (LAPAR et al., J Thorac Cardiovasc Surg, (2011),142:887-894; BOEHLER et al., Transpl Immunol, (2002), 9:121-124; STONE et al., Respir Res, (2017), 18:212). In addition, we discovered that regadenoson diminished lung transplant-induced plasma sRAGE production and matrix metalloproteinase-9 (MMP-9), an important enzyme that shed cell-anchored full length RAGE into sRAGE (reported in another manuscript). Using an in vitro cell culture model, we showed that stimulating MMP-9 in monocytes/macrophages increased Srage production, while both MMP inhibitor and $A_{2A}R$ agonists inhibited this shedding process (reported in another manuscript). Therefore, regadenoson may protect IRI by suppressing proinflammatory cytokines/chemokines (such as IL-6, IL-8, TNF-a and sRAGE) and by stimulating anti-inflammatory cytokine (such as IL-10). These results indicate that regadenoson may be beneficial for lung transplant recipients.

In summary, we provided additional evidence that continuous regadenoson infusion (at dose 1.44 and 2.88 ug/kg/hr for 12 hours) is safe and feasible in lung transplant recipients. We also reported that regadenoson infusion improved PGD scores and reduced intubation times when compared with control patients. In addition, regadenoson elicits an anti-inflammatory effect by suppressing IL-6, IL-8, sRAGE and possibly TNF-α, and enhancing IL-10. These inflammation biomarkers may be useful in assessing acute lung transplant injury and the effectiveness of anti-inflammatory drugs in very early-stage post lung transplantation. These findings pave the way for a Phase II randomized multi-center trial to further evaluate the safety and efficacy of regadenoson post lung transplantation.

Chemicals and Reagents. Regadenoson (purity 99.83%) was purchased from Selleckchem (Houston, TX, USA) and Regadenoson-d3 ((purity 99.68%) used as internal standard (IS) was obtained from Toronto Research Chemicals, (North York, ON, CT). Optima LC/MS grade water (H2O), methanol, and formic acid (FA) were purchased from Fisher Scientific (Pittsburgh, PA, USA).

Calibration Standards. 1 mg/ml stock solutions of Regadenoson and Regadenoson-d3 were prepared in Dimethyl sulfoxide (DMSO) and further working solutions to spike in plasma were prepared in methanol and water (70:30, v/v). Calibration standards (STD) in plasma ranged from 0.05 ng/ml to 50 ng/ml (8 points: 0.05, 0.1, 1, 5, 20, 30, 40, and 50 ng/ml). Quality control (QC) samples at 3 concentration levels (0.15 ng/ml, LQC; 25 ng/ml, MQC; and 45 ng/ml, HQC) were also prepared in plasma. Internal standard solution (Regadenoson-d3; 250 ng/ml) was prepared in methanol and water (70:30, v/v).

Sample Preparation. 50 μL of plasma sample (STD/QC/test sample) was added into a 2 ml centrifuge tube containing 20 μL of IS solution (250 ng/ml) and mixed well. Next, 500 μL of acetonitrile was added, shaken for 3 min at 2100 rpm, and centrifuged for 10 min at 15000 rpm. 400 μL of supernatant was transferred to glass tube and dried under a steady stream of nitrogen at 35° C. The sample was re-suspended in 100 μL of 0.1% formic acid in H2O: 0.1% formic acid in methanol (1:1 v/v) and injected (3 μl) into LC-MS/MS system.

Liquid Chromatography Tandem Mass Spectrometry (LC-MS/MS). LC-MS/MS analysis was performed on a TSO Altis Triple Stage Quadrupole Mass Spectrometer coupled to an Ultimate 3000 RS Liquid Chromatogram system (Thermo Scientific, San Jose, CA). The LC separation was performed on a BEH C18 column (2.1×50 mm, 1.7 μm) (Waters Corporations, Milford, MA) operated at 30° C. Mobile phase solvent A and B consisted of 0.1% FA in H2O and 0.1% FA in methanol, respectively. The gradient program started with 35% B; followed by a linear gradient to 50% B in 0.7 min; maintained 50% B until 1.5 min; followed by a linear gradient back to 35% B in 2 min and maintained until 3 min. The flow rate was set at 0.22 ml/min. The retention time of Regadenoson and the IS was 1.09 min, and the total run time was 3 min.

Detection was performed in the positive-ion mode using electrospray ionization (ESI). Source parameters were as follows: spray voltage, 3500; Ion transfer tube temperature, 350; vaporizer temperature, 300; sheath gas pressure, 50; auxiliary gas pressure, 10; and sweet gas, 1. The compound parameters: collision energy (CE), and RF lens were 35 and 77 V, respectively for Regadenoson and the IS. Selected reaction monitoring (SRM) was used for mass detection with the following transitions: Regadenoson (m/z 391.1-259.2; quant) and (m/z 391.1-228.1; qual), Regadenoson-d3 (m/z 394.0-262.2; quant) and (m/z 394.0-228.2; qual). Data collection and analysis was performed by Xcalibur V 2.1 (Thermo Scientific, San Jose, CA).

Analytical parameters: The linear range is 0.05-50 ng/mL in human plasma. Samples that exceeded the upper limit of quantification were diluted 2 or 4 fold and reinjected.

Example 5. Regadenoson Reduces Plasma Levels of Soluble Receptor for Advanced Glycation End-Products By Inhibiting Matrix Metalloproteinase-9 in Lung Transplantation Recipients Materials and Methods Treat Lung Transplant Recipients with Regadenoson The study conducts and rationale for dose selection was published in our previous publication (LAU et al., J Heart Lung Transplant, (2020), 39:563-570). Briefly, since our lung transplantation trial and adult sickle cell trial showed that regadenoson infusion at 0.24 (initial dose), 0.60 (lower dose), and 1.44 ug/kg/hour (low dose) was safe in lung transplant recipients and sickle cell disease patients, we modified our protocol to a high dose infusion at the 2.88 ug/kg/hour for 12 hours in the last three lung transplantation recipients (FIELD et al., Blood Adv, (2017), 1:1645-1649). The regadenoson infusion started at the time of skin incision (to ensure that adequate plasma levels were present at time of reperfusion), continued throughout the transplant procedure and into the immediate postoperative period for a total duration of 12 hours.

Luminex Assay for Damage-Associated Molecular Patterns Molecules

We designed this trial mainly as a Phase I safety and feasibility study that would allow an optimal infusional dose to be determined based on dose-limiting toxicities identified in lung transplant recipients. We also evaluated the potential efficacy by clinical outcomes and the lab evaluation of various cytokines/chemokines, DAMPs and enzymes. Blood was drawn for cytokine/chemokine, DAMPs and MMP-2/-9 analysis at the following different timepoints: 1) before infusion, 2) 15 minutes before reperfusion of the 1st lung, 3) 30 minutes after reperfusion of 1st lung, 4) 30 minutes after reperfusion of 2nd lung, and 5) 6 hours after reperfusion of 1st lung. HMGB1 and sRAGE levels were measured using a customized human Cytokine/Chemokine multiplex immunoassay (Millipore Sigma, Burlington, MA) at The University of Virginia Flow Cytometry Core (RRID: SCR_017829) as previously described (LAU et al., J Heart Lung Transplant, (2020), 39:563-570).

Flow Cytometry Analysis

Flow cytometry was performed according to our previous publication with minor modifications (LAPAR et al., Ann Thorac Surg, (2011), 92:470-477; discussion 477). Briefly, the peripheral blood mononuclear cells (PBMCs) were prepared to measure the expression of $A_{2A}R$ at the same timepoints as described in the cytokine Luminex assay above. Leukocytes were stained with B cell & conventional T & invariant natural killer T (iNKT) cell panel or myeloid panel for subsets of monocyte and dendritic cells. The fluorophore-conjugated anti-human antibodies are listed in the supplemental table 1. Cell pelmeability was then performed using a Cytofix/Cytopelm kit (BD Biosciences) prior to intracellular staining. The stained samples were subsequently analyzed using a LSRII-1 flow cytometer. The data was analyzed with FCS Express 7 and GraphPad Prism 9.0.

Monocyte/Macrophage Culture and Treatment

Mouse alveolar macrophages (MHS, ATCC CRL-2019) were obtained from BALB/c mouse lung alveolar. A monocyte/macrophage cell line, RAW 264.7 (ATCC TIB-71, RAW) was also utilized to confirm our findings in MHS cells. RAW cells are a macrophage-like, Abelson leukemia virus transformed cell line derived from BALB/c mice. Both MHS and RAW cells were grown in RPMI-1640 media (Invitrogen, Carlsbad, CA), which were supplemented with 10% FBS, and 1% Penicillin/Streptomycin (additional of 0.05 mM 2-mercaptoethanol (Sigma) for MHS cells only) in a humidified incubator containing 5% CO2 at 37° C. When the cell density reached 70-80% confluence, the MHS/RAW cells were treated with 20 nM PMA, 2 nM MMP inhibitor GM6001, 100 nM regadenoson, 10 nM ATL146e, lipopolysaccharides (LPS, 75 ng/ml) and combinations of these reagents for 24 h. The medium was then collected, and cells were lysed with RIPA buffer (50 mM TrisHCl, PH 7.4, 150 mM NaCl, 1% NP-40, 0.5% sodium deoxycholate, 0.1% SDS) for subsequent gelatin zymography and Western blot analysis.

Western Blot Analysis

The conditioned media were subjected to standard Western blot analysis according to previous methodology (ZHAO et al., J Biol Chem, (2003), 278:15056-15064; ZHAO et al., Am J Physiol Lung Cell Mol Physiol, (2011), 300: L718-729). Equal amounts of total protein (20 μg) were loaded per lane. The primary antibodies were mouse anti-mouse sRAGE (MilliporeSigma, Burlington, MA) and mouse anti-mouse MMP-2 (Thermo Scientific, Waltham, MA) antibodies. The 2nd antibody is HRP conjugated goat anti-mouse (Cell Signaling). Super Signal West Pico plus Chemiluminescent Substrate was used to reveal positive signals. The bands were detected and semi-quantified with Bio-Rad ChemiDoc MP Imaging System (Bio-Rad, Hercules, CA).

Immunofluorescence Staining

Immunofluorescence staining of sRAGE was performed according to our previous description (ZHAO et al., Am J Physiol Lung Cell Mol Physiol, (2011), 300: L718-729). Briefly, MHS and Raw cells were cultured on eight-well slides for 24 h followed by treating with PMA, LPS, GM6001, regadenoson, ATL146e, and combinations of these reagents for another 24 h. Cells were then fixed in 50% Acetone and 50% methanol for 15 min at room temperature and permeabilized with 0.2% Triton X-100 in Tris-buffered saline. The fixed, permeabilized cells were stained overnight at 4° C. with mouse anti-mouse sRAGE (MilliporeSigma, Burlington, MA). Secondary Alex 488-conjugated donkey anti-mouse IgG was subsequently applied at a 1:200 dilution for I h at room temperature. 4',6-diamidino-2-phenylindole (DAPI, I μg/ml, Roche Diagnostics) was used for nuclear counter staining. Slow Fade mounting medium was added to the slides, and images were obtained by using a fluorescence microscope (Leica DM6M) equipped with a Leica DFC 9000GT digital camera.

Images were processed for reproduction using Photoshop software 22.4.3 (Adobe Systems, Mountainview, CA).

Gelatin Zymography

Plasma samples were collected as described above. Protein concentrations were determined with BCA protein assay. Equal amounts of proteins (20 μg) were loaded in each lane for MMP-2 and-9 gelatinolytic activity detection by use of gelatin zymography as our previous publications (ZHAO et al., J Biol Chem, (2003), 278:15056-15064; ZHAO et al., Am J Physiol Lung Cell Mol Physiol, (2011), 300: L718-729).

Proteomic Assay Using MS and MS/MS

The proteomic assay was performed at The W.M. Keck Biomedical Mass Spectrometry Laboratory at the University of Virginia. Briefly, the plasma samples were reduced with 10 mM DTT followed by alkylation with 50 mM iodoacetamide. The sample was then digested overnight at 37° C. with 0.1 μg trypsin. The sample was acidified with acetic acid to stop digestion. The solution was evaporated to 50 μL for MS analysis using the LC-MS system. The data of proteomic assay was analyzed by database searching using the Sequest search algorithm against a database of Uniprot Human.

Statistical Analysis

Statistical differences between groups were determined by two-way ANOVA followed by Tukey's multiple comparison test (GraphPad Prism 9.0). The flow cytometry data was analyzed with FCS Express 7. Data were reported as means±SD. P value equal or less than 0.05 was considered significant.

Results

Regadenoson Treatment Significantly Reduced Plasma Levels of sRAGE, but not HMGB I We have reported that regadenoson reduced PGD scores at 24, 48 and 72 hours and decreased transplant-induced plasma levels of proinflammatOly cytokines IL-6, IL-8, and TNF-α post lung transplantation (unpublished data, presented in the ISHLT 42nd Annual Meeting and Scientific Sessions). In this study, we tried to explore another potential molecular mechanism through which $A_{2A}R$ may protect lung IRI post long transplantation. HMGB 1 and RAGE mediated lung IRI in our previous reports and other's findings (SHARMA et al., Am J Transplant, (2013), 13:2255-2267; STONE et al., Respir Res, (2017), 18:212; LI et al., Dose Response, (2020); 18:1559325820969340; ALI et al., Ann Thorac Surg, (2012), 93:282-288). sRAGE is associated with PGD development post lung transplantation and has been proposed as biomarker for PGD (CHRISTIE et al., Am J Respir Crit Care Med, (2009), 180:1010-1015; DIAMOND et al., Transplantation, (2017), 101:21-22; SHAH et al., J Heart Lung Transplant, (2012), 31:942-949; POTTECHER et al., Transplantation, (2017), 101:112-121). We measured plasma levels of HMGB 1 and sRAGE in lung transplant recipients receiving perioperative regadenoson and controls. The results showed that Regadenoson infusion significantly reduced transplantation-induced plasma levels of sRAGE at 30 minutes post the 1st lung reperfusion in patients receiving 1.44 ug/kg/hr (n=14), and at 30 minutes post the 2nd lung reperfusion in both 1.44 ug/kg/hr and 2.88 ug/kg/hr-treatment groups (n=3, P<0.0001) when compared with control group (n=7, FIG. 21A). The sRAGE level was decreased in trend (P=0.0656) at 30 minutes post the 1st lung reperfusion in the high dose treated group when compared with saline infused control group (n=7, FIG. 21A). Regadenoson infusion had no significant effect on the plasma levels of HMGB-1 at any timepoints in these patients (P>0.05, FIG. 21B). Effects of regadenoson on plasma levels of MMP-2 and MMP-9 and TIMP-1

Figure 22:
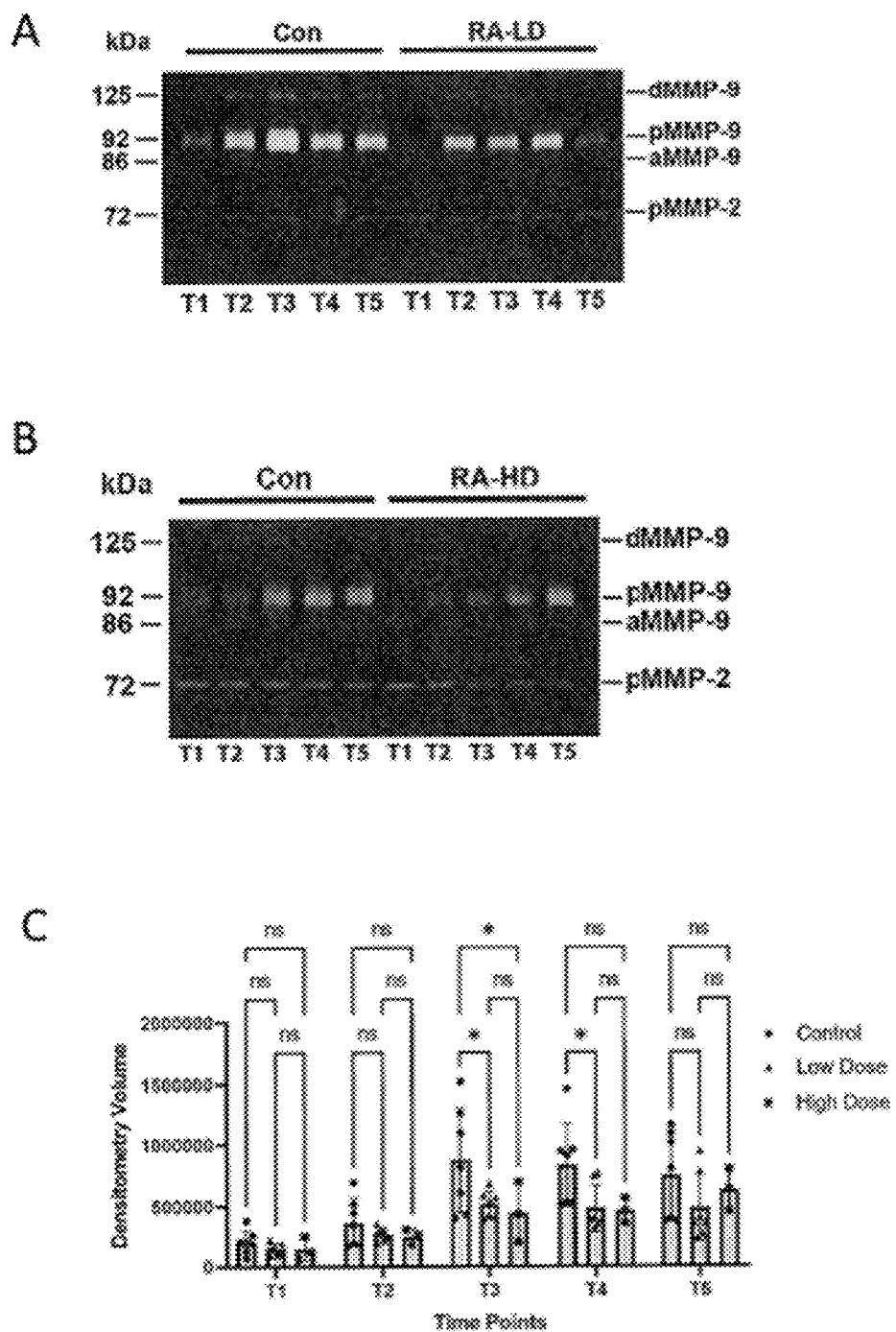
FIG. 22. Plasma levels of matrix metalloproteinase-2/-9 (MMP-2/9) and tissue inhibitor of metalloproteinase-1 (TIMP-1). The samples used in these assays are collected at the same timepoints (T1-T5) as indicated in FIG. 21. Representative images of MMP-2 and -9 levels in the controls vs a low dose treated patient (A) and a high dose treated patient (B). MMP-2/-9 were detected by gelatin zymography. Con: control samples; RA-LD: Low dose regadenoson treatment; RA-HD: How dose regadenoson treatment; dMMP-9:dimerized MMP-9; pMMP-9: pro-MMP-9, aMMP-9: active form MMP-9. (C): Densitometry scanning and semiquantitative analysis of the levels of MMP-9 in the plasma of regadenoson-treated and control patients. Data shown are the mean±S.D. *, p<0.05. Control: n=7, Low dose treated patients: n=7, High dose treated patients: n=3. (D): Densitometry scanning and semiquantitative analysis of the levels of MMP-2 in the plasma of regadenoson-treated and control patients. (E) Quantitative analysis of TIMP-1 in 3 controls and 3 low dose treated lung transplantation patients at the following timepoints: T1, prior infusion (baseline); T3, 30 minutes after reperfusion of 1st lung; TS, 6 hours after reperfusion of 1st lung.

Since sRAGE were generated through shedding the membrane-anchored full-length RAGE by MMP-9 in vivo, we evaluated MMP-2 and -9 enzymatic activities by gelatin zymography (ZHANG et al., J Biol Chem, (2008), 283: 35507-35516). We found that the gelatinolytic activity of MMP-9 was significantly decreased in both low dose and high dose treated groups compared with control group at 30 minutes after 1st (low dose vs control, p=0.014; high dose vs control, p=0.026) and 2nd (low dose vs control, p=0.017; high dose vs control, p=0.061) lung reperfusion (FIG. 22A-22C). However, MMP-2 had no significant change in both regadenoson-treated groups compare to control group (P>0.05) (FIG. 22D). TIMP-1 is an endogenous and specific MMP-9 inhibitor (RODERFELD et al., Biol Chem, (2007), 388:1227-1234; REIS et al., Int J Biol Markers, (2011), 26:255-261)). We detected the expression of TIMP-1 in control and low dose regadenoson treated patients. The results demonstrated the regadenoson treatment increased plasma TIMP-1 levels compared to controls at 30 minutes after reperfusion of 1st lung (p=0.004) and 6 hours after reperfusion of 1st lung (p=0.019) (FIG. 22E).

$A_{2A}R$ Expression on Inflammatory/Immune Cells

The B cell, conventional T & iNKT cells were gated as showed in FIG. 23A. The subsets of monocyte and dendritic cells were gated as shown in FIG. 23B. Median fluorescent intensity (MFI) were analyzed with FCS Express 7 and GraphPad Prism 9.0. The $A_{2A}R$ expression on CD3+6B 11+iNKT cells was significantly higher than any other cells/subsets of cells (P<0.0001, FIG. 3C). The $A_{2A}R$ expression on classical monocytes (CM) are also significantly higher than CD3+6B1 1-conventional T cells (p=0.0210) and B cells (P=0.0281). $A_{2A}R$ expression on intermediate monocytes (IM) was significantly higher than that on conventional T cells, B cells, myeloid dendritic cells (mDC) and plasmacytoid dendritic cells (pDC) (p<0.0001, FIG. 23C). In addition, $A_{2A}R$ expression on non-classical monocytes (NCM) were also higher than that on conventional T cells (p=0.0736), B cells (p=0.0972, FIG. 23C). $A_{2A}R$ expression is very low in conventional cells, B cells, mDCs and pDCs and there was no significant difference among these cells (P>0.05).

Figure 24:
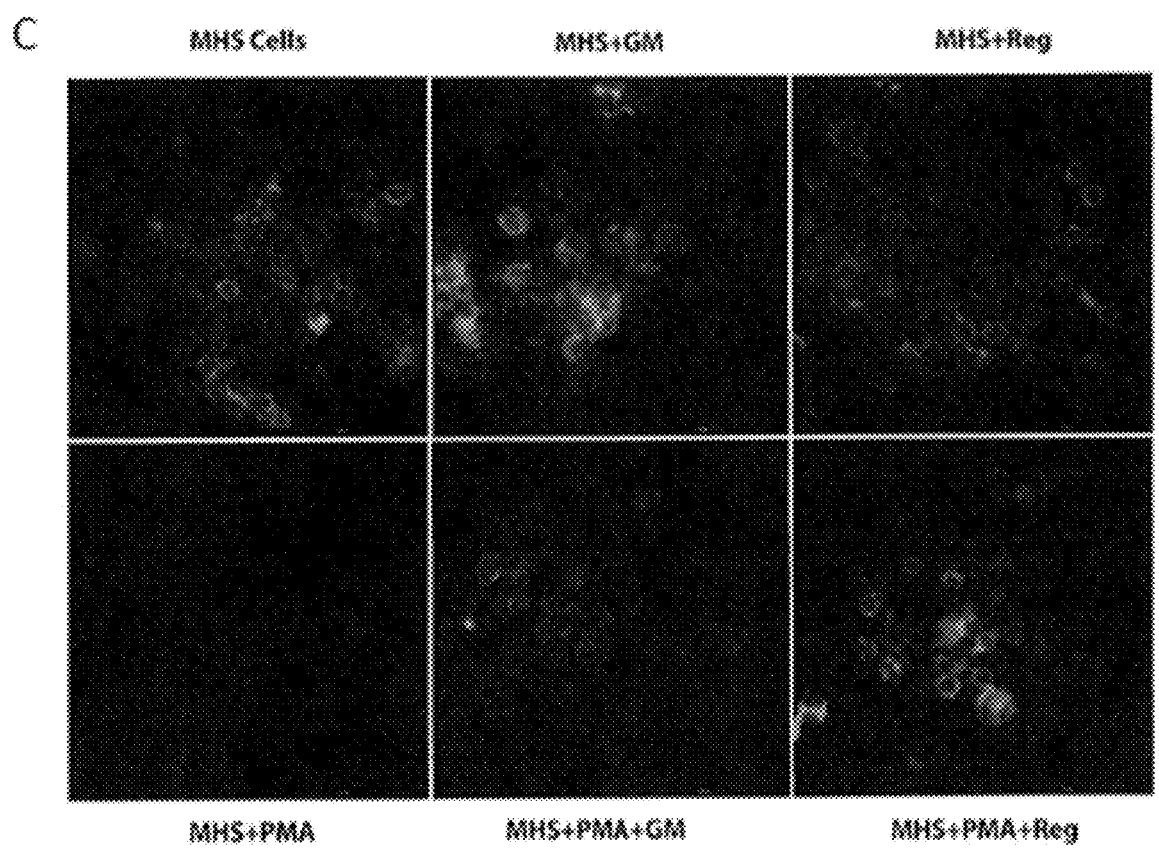
FIG. 24. MMP-9 cleave cell-bound RAGE into sRAGE in alveolar macrophage (MHS). (A) Gelatin zymography images of PMA stimulates MMP-9, but not MMP-2 in the MHS conditional media. The MHS cells are treated with PMA (20 nM), GM6001 (2 nM) and Regadenoson (100 nM) for 24 hours. (B) Western blot analysis of sRAGE protein in MRS cell conditional media. (C) Immunofluorescence staining of RAGE on MHS cells. Green indicates positive RAGE staining signals. Cells were counter-stained with DAPI to reveal nuclei (Blue). Photographs were taken under a Leica microscope with 600× magnification. PMA: Phorbol 12-myristate 13-acetate, GM: MMP inhibitor GM6001, Reg: Regadenoson.
Figure 27A:
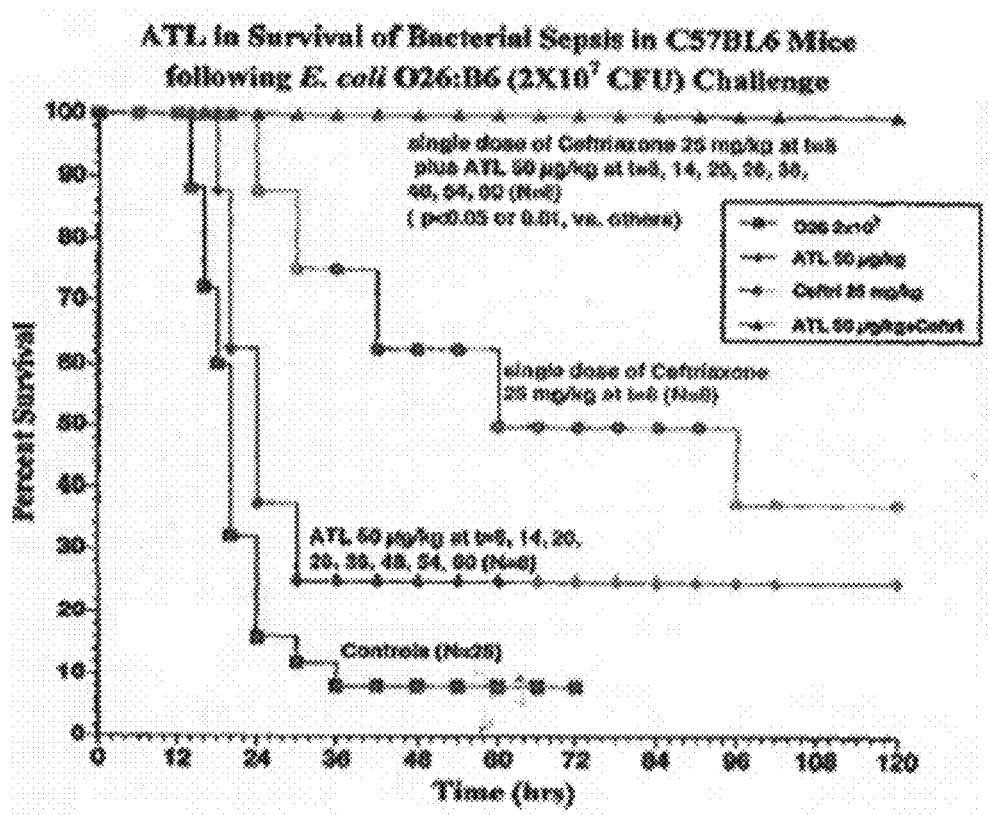
FIGS. 27A and 27B show that ATL-1464 inhibits sepsis in mouse (FIG. 27A) and rat (FIG. 27B) models of sepsis.
Figure 27B:
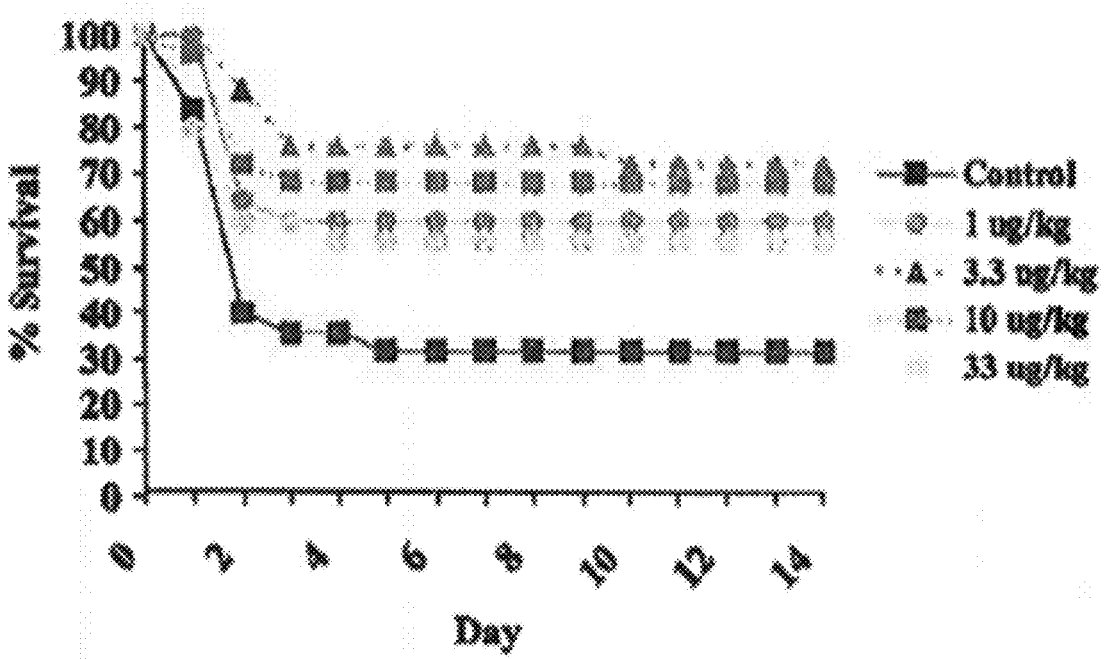
Figure 28:
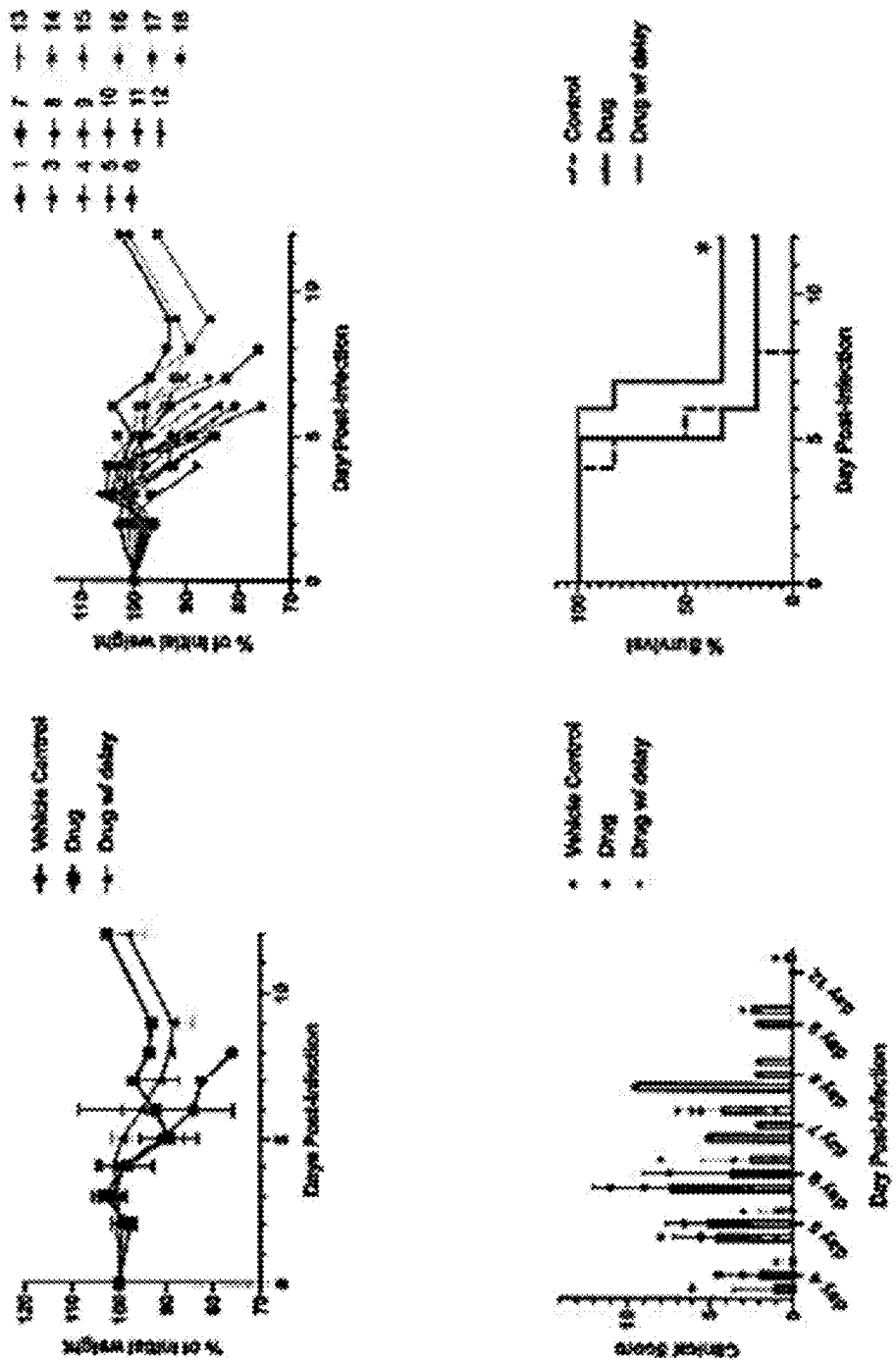
FIG. 28. Results of experiments conducted in mice with A2A receptor agonist, ATL146e (independent trial experiment #1). Mice: 18 mice (approx. 120 days old), all males Control: (1-6) (n=6): Vehicle prechallenge; Drug (no delay) (7-12) (n=6): ATL146e prechallenge (day-1); Drug (with delay (13-18) (n=6) ATL 146e with 24 hour delay (day−1 preinfection); Drug delivered with Alzet pump. Dose 1.44 ug/kg/h. Viral Dose: Pfu of Hong Kong/VM20001061/2020 via intranasal route 1250 PFU (50 uL) 1 day after pump implantation. Weighed and clinical scores daily. Euthanized mice when met criteria. Collected BALF, Lungs for titer, Blood, Histology-lungs, heart, kidney, small intestine. Treatment with ATL146e resulted in a decrease in clinical symptoms and increased survival. The delivery of ATL146e 4-6 hours after infection improves survival and clinical scores. The truce receiving the drug with delay trended to do better even though the survival data were similar. Combined survival data: 1/12 vehicle mice survived; 4/12 drug with no delay survived; 5/12 drug with delay survived.
Figure 29:
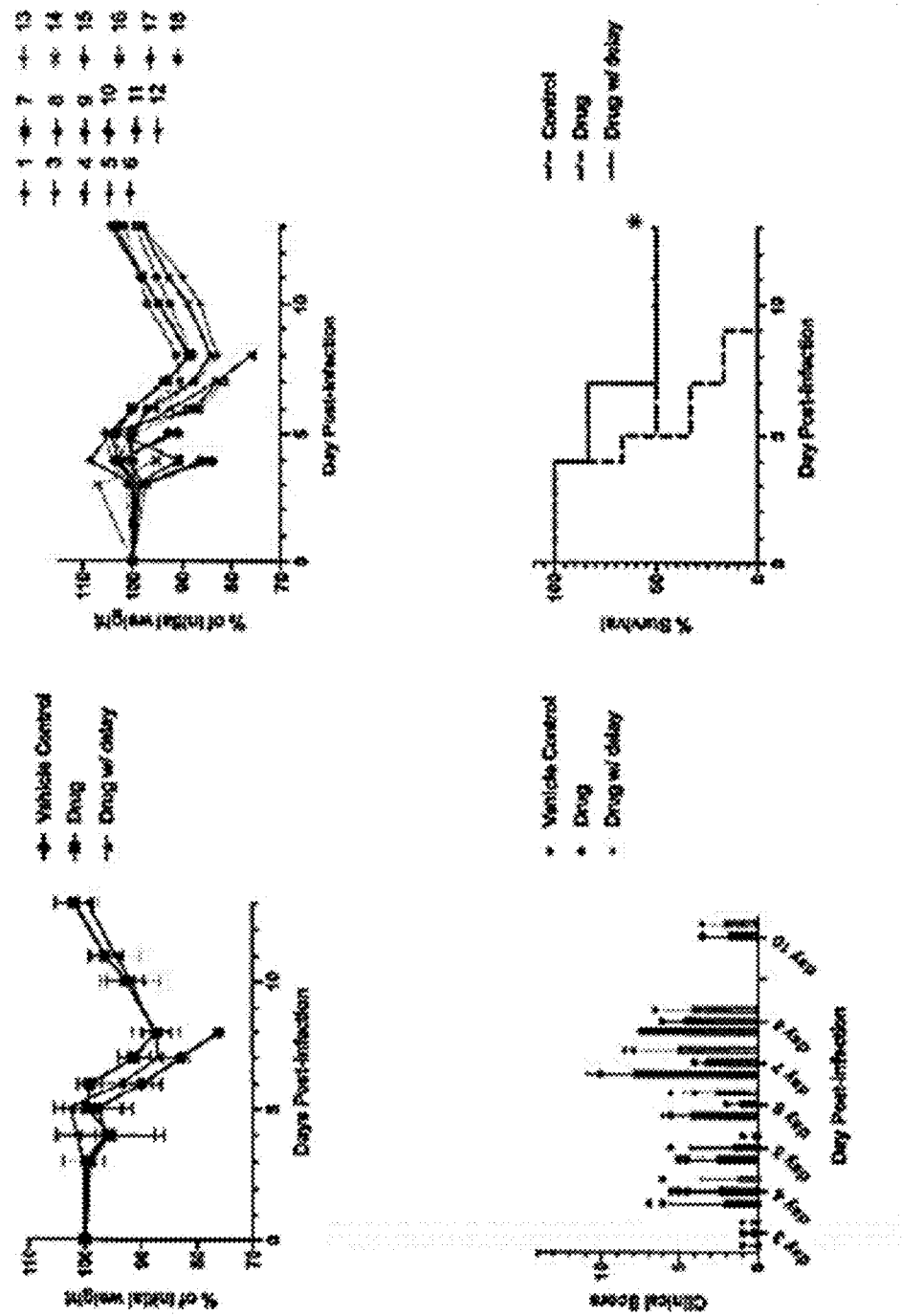
FIG. 29. Results of experiments conducted in mice with $A_{2A}$ receptor agonist, ATL146e (independent trial experiment #2). Mice: 18 mice (138 days old), all males Control: (1-6) (n=6): Vehicle prechallenge; Drug (no delay) (7-12) (n=6): ATL146e prechallenge (day-I); Drug (with delay (13-18) (n=6) ATL 1 46e with 24 hour delay (day−1 preinfection); Drug delivered with Alzet pump. Dose 1.44 ug/kg/ h. Viral Dose: Pfu of Hong Kong/VM20001061/2020 via intranasal route 1250 PFU (50 uL) 1 day after pump implantation. Weighed and clinical scores daily. Euthanized mice when met criteria. Collected BALF, Lungs for titer, Blood, Histology-lungs, heart, kidney, small intestine. Treatment with ATL146e resulted in a decrease in clinical symptoms and increased survival. The delivery of ATL146e 4-6 hours after infection improves survival and clinical scores. The truce receiving the drug with delay trended to do better even though the survival data were similar. Combined survival data: 1/12 vehicle mice survived; 4/12 drug with no delay survived; 5/12 drug with delay survived.
Figure 30:
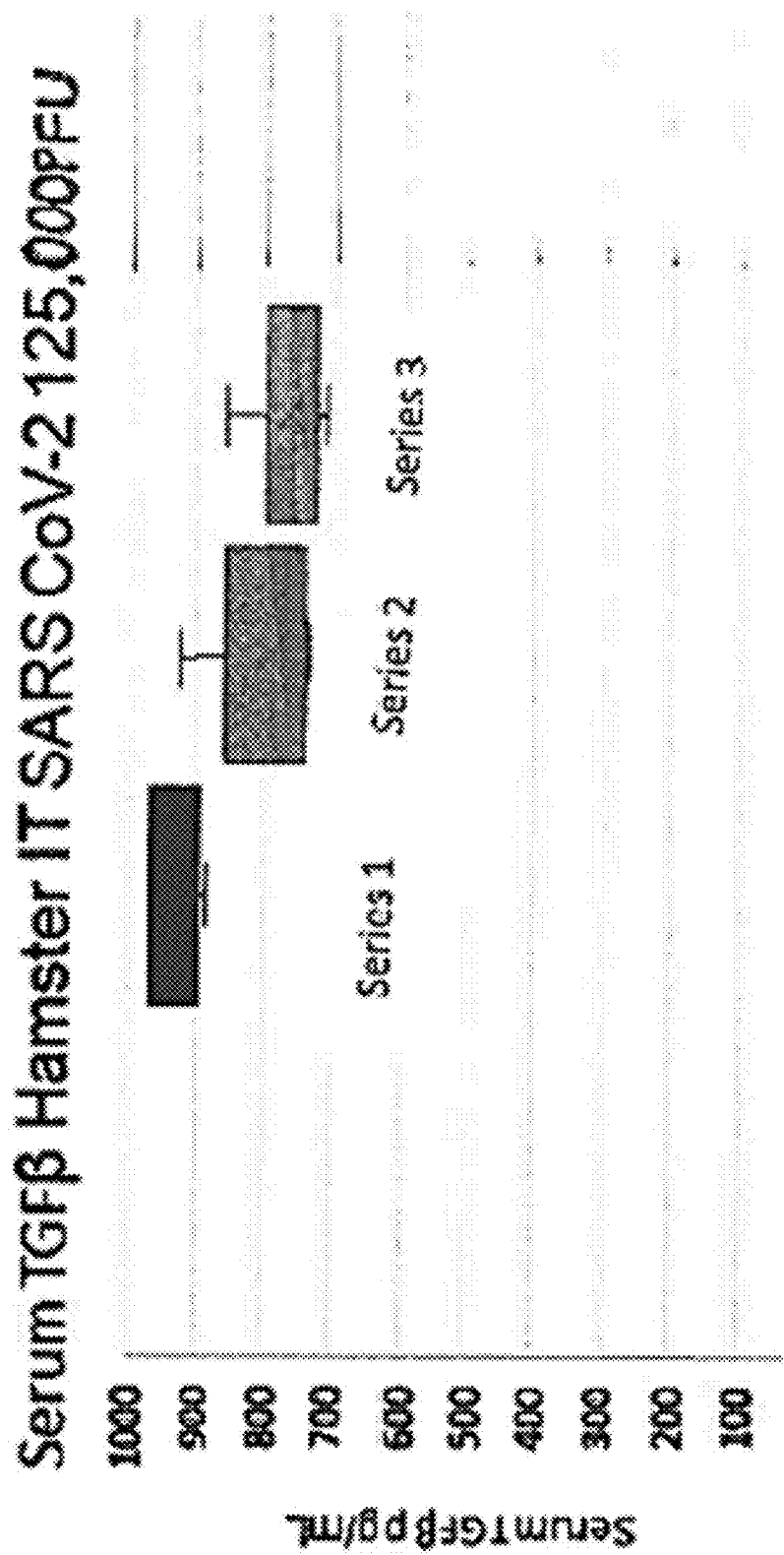
FIG. 30. shows that the adenosine compounds diminish the increase in Transforming Growth Factor beta (TGF-β) which increases during a SARS CoV-2 infection.
Figure 32:
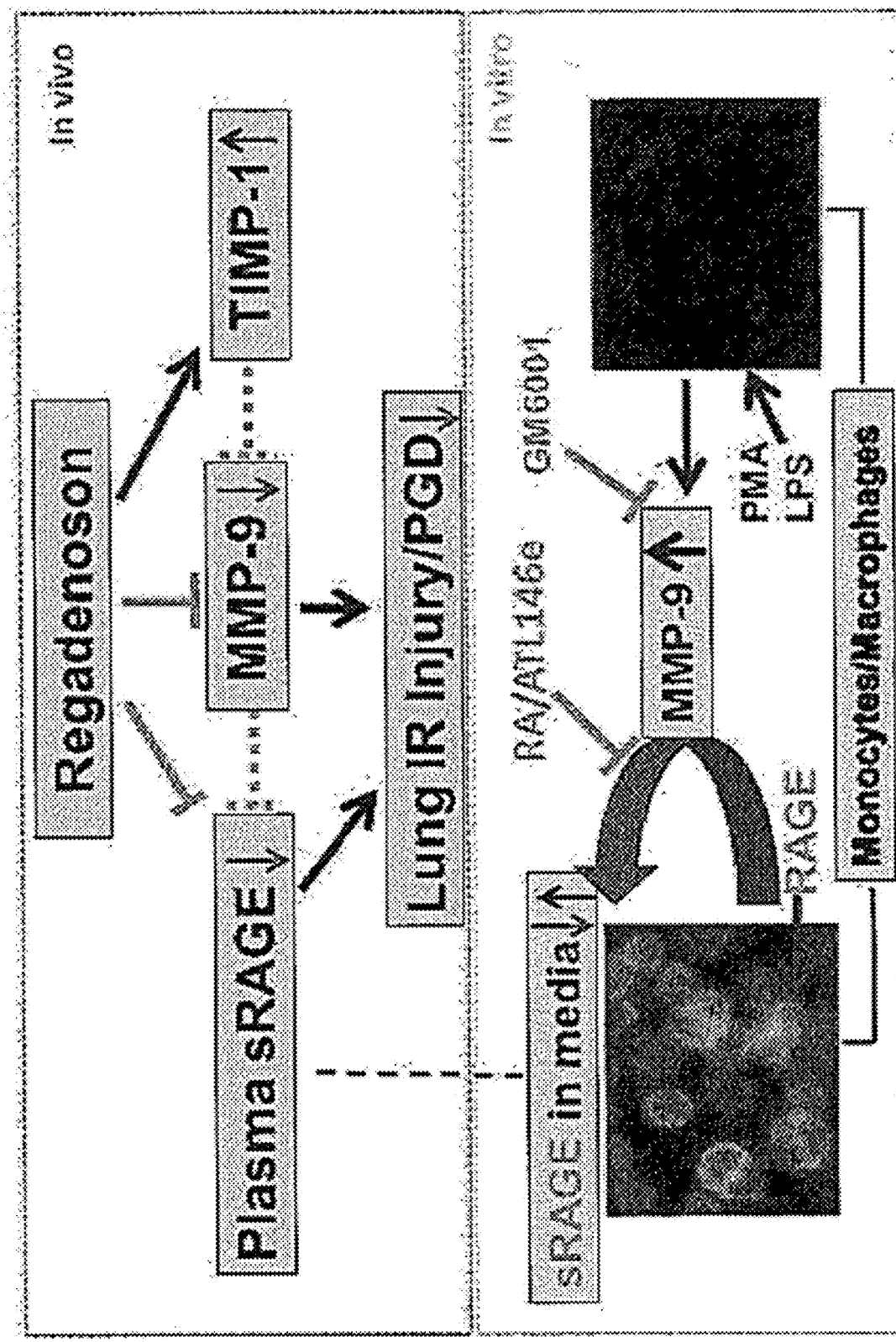
FIG. 32. Regadenoson reduces plasma levels of matrix metalloproteinase-9 (MMP-9) and soluble receptor for advanced glycation end-products (sRAGE) in vivo and RAGE shedding in vitro. Red arrows indicate up-regulation, green arrows indicate down-regulation. Dotted lines indicate possible interactions. The curved blue arrow indicates cleaving/shedding. Green and red colors show cell-bounding RAGE and MMP-9, respectively. RA: regadenoson, LPS: lipopolysaccharides, TIMP-1: tissue inhibitor of metalloproteinase-1, PMA: phorbol 12-myristate 13-acetate, IR: ischemia reperfusion injury, PGD: primary graft dysfunction, GM6001: MMP inhibitor, ATL146e: a selective adenosine A2A receptor agonist. (FROM EXAMPLE 5).

MMP-9 Shed sRAGE on Monocytes/Macrophages In Vitro $A_{2A}R$ is highly expressed on iNKT cells and monocyte/macrophages compared with the other subsets of leukocytes. Isolated rat primary alveolar macrophages expressed membrane-bound RAGE protein in response to stimuli (STAITIEH et al., Am J Med Sci, (2018), 355:497-505). MMP-9 has been implicated in the generation of the cleaved form of sRAGE (ZHANG et al., J Biol Chem, (2008), 283:35507-35516; STAITIEH et al., Am J Med Sci, (2018), 355:497-505). We tested the expression of RAGE and MMP-9 and their interaction in a mouse alveolar macrophage cell line (MHS) in the presence/absence of MMP-9 stimulators and inhibitor. The results revealed that MHS expressed RAGE and MMP-9. MMP-9 levels in the MHS conditional media were significantly elevated when treated with PMA, an MMP-9 specific stimulator. Meanwhile the MMP-2 levels were not significantly affected (FIG. 24A). The Western blot revealed that the levels of sRAGE in the conditional media were increased in the PMA treated cells and decreased in the GM6001 (a MMP inhibitor) and $A_{2A}R$ agonists treated cell media (FIG. 24B). The cell membrane-anchored RAGE were decreased in the PMA-treated MHS cells, while GM6001 and $A_{2A}R$ agonists [regadenoson (FIG. 24C) and apadensoson (ATL-146e, data not shown)] suppressed the shedding of RAGE in these cells. Since both regadenoson and apadensoson had no effects on PMA-induced MMP-9 levels, we further tested LPS-induced activation of MHS cells, which is more patho-physiologically related to acute lung injury. The result showed that both regadenoson and apadensoson partially suppressed LPS-induced MMP-9 levels (FIG. 25A). These two $A_{2A}R$ agonists and/or GM6001 inhibited sRAGE shedding on MHS cells (FIG. 25B). Similar results were obtained with a mouse monocyte/macrophage cell line, Raw264.7 cells (Supplemental FIGS. 26A & 26B).

Discussion

RAGE is a multiligand pattern recognition cell surface receptor for DAMPs molecules, such as high mobility group box I (HMGB1) and S100 proteins (ERUSALIMSKY et al., Redox Biol, (2021), 42:101958; HUDSON et al., Annu Rev Med, (2018), 69:349-364). RAGE plays an important role in the innate immune response and as a mediator of pro-inflammatory processes. Upon ligand binding, RAGE-mediated intracellular signaling results in elevated production of reactive oxygen species and activate nuclear factor kappa B (NF-kB) (ZHANG et al., Circulation, (2006), 113:1235-1243). NF-kB subsequentially stimulates the expression of pro-inflammatory modulators, such as TNF-α, IL-6(ERUSALIMSKY et al., Redox Biol, (2021), 42:101958). Therefore, RAGE activation may provide a positive feedback mechanism to amplify the inflammatory response.

HMGB 1 and RAGE are known to independently mediate lung ischemia-reperfusion injury in mouse IR models (CHEN-YOSHIKAWA et al., J Thorac Cardiovasc Surg, (2019), 157: 2107-2108; CHEN-YOSHIKAWA et al., Cells, (2021), 10). RAGE is abundantly produced in both rat and human lungs, which indicate that RAGE may play an important role in lung physiological and pathological processes (PELAEZ et al., Am J Transplant, (2010), 10: 900-907; FEHRENBACH et al., Cell Mol Biol {Noisy-le-grand), (1998), 44:1147-1157.

In addition to cell membrane-anchored RAGE, there is another form of this receptor, named soluble RAGE (sRAGE), which lacks its transmembrane and cytoplasmic domains (ERUSALIMSKY et al., Redox Biol, (2021), 42:101958). sRAGE can be detected in plasma/serum and other body fluids, such as BAL. There are two major forms of sRAGE: the major form of sRAGE is produced at the cell surface by the proteolytic cleavage of RAGE at the boundary between its extracellular and transmembrane portions by matrix metalloproteinases, such as MMP-9 and ADAM-10 (ZHANG et al., J Biol Chem, (2008), 283:35507-35516; RAUCCI et al., Faseb j, (2008), 22:3716-3727. Another form of sRAGE is endogenous secretory RAGE (esRAGE), which accounts for less than 25% of the total circulating sRAGE (ERUSALIMSKY et al., Redox Biol, (2021), 42:101958).

$A_{2A}R$ agonists are known to play an anti-inflammatory role in acute lung injury and IRI by inhibiting various inflammatory cytokines (SHARMA et al., Am J Respir Crit Care Med, (2016), 193:988-999; STONE et al., Transplantation, (2015), 99:2494-2503; LAPAR et al., J Thorac Cardiovasc Surg, (2011), 142: 887-894; FOLKESSON et al., Am J Physiol Lung Cell Mal Physiol, (2012), 303: L259-271; HE et al., Cell Signal, (2013), 25:1913-1923; LI et al., PLoS One, (2013), 8:e59257). Our results showed that treatment with regadenoson significantly reduced lung transplantation-induced sRAGE as early as 30 minutes post first lung reperfusion. The role sRAGE plays in a variety of diseases is still under debate.

Generally, sRAGE plays a protective anti-inflammatOly role by acting as a decoy receptor, binding RAGE ligands and thus blocking their interaction with membrane-bound RAGE (39). However, accumulated data has shown that the levels of sRAGE are positively associated with lung IR injury (46) and positively associated with PGD scores in several lung transplantation studies (CHRISTIE et al., Am J Respir Crit Care Med, (2009), 180:1010-1015; DIAMOND et al., Transplantation, (2017), 101:21-22; SHAH et al., J Heart Lung Transplant, (2012), 31:942-949; POTTECHER et al., Transplantation, (2017), 101:112-121; HANG et al., Int J Mol Med, (2019), 43:2507-2515). These studies indicated that sRAGE was one of the biomarkers for the disruption of epithelial integrity in the early stage of IR injuly post lung transplantation. Levels of sRAGE were also found to coincide with increased length of hospitalization and POD severity post lung transplantation (PELAEZ et al., Am J Transplant, (2010), 10: 900-907). sRAGE was detelmined to have proinflammatory properties since it stimulates the production of IL-6, TNF-α, and macrophage inflammatory protein 2. This effect was triggered by interaction with leukocyte beta2 integrin Mac-1 and was mediated via NF-kB (ERUSALIMSKY et al., Redox Biol, (2021), 42:101958; WANG et al., J Immunol, (2010), 185:1822-1835). sRAGE also stimulated Raw cells producing IFN-r via NF-kB pathway (ZHANG et al., Int J Mol Med, (2019), 43:2507-2515). Apart from its proinflammatOly properties, sRAGE was proven to act as a chemotactic stimulus for neutrophils (PULLERITS et al., Arthritis Rheum, (2006), 54:3898-3907). Thus, sRAGE has pro-inflammatoly role in lung IR injury post translation.

Figure 21:
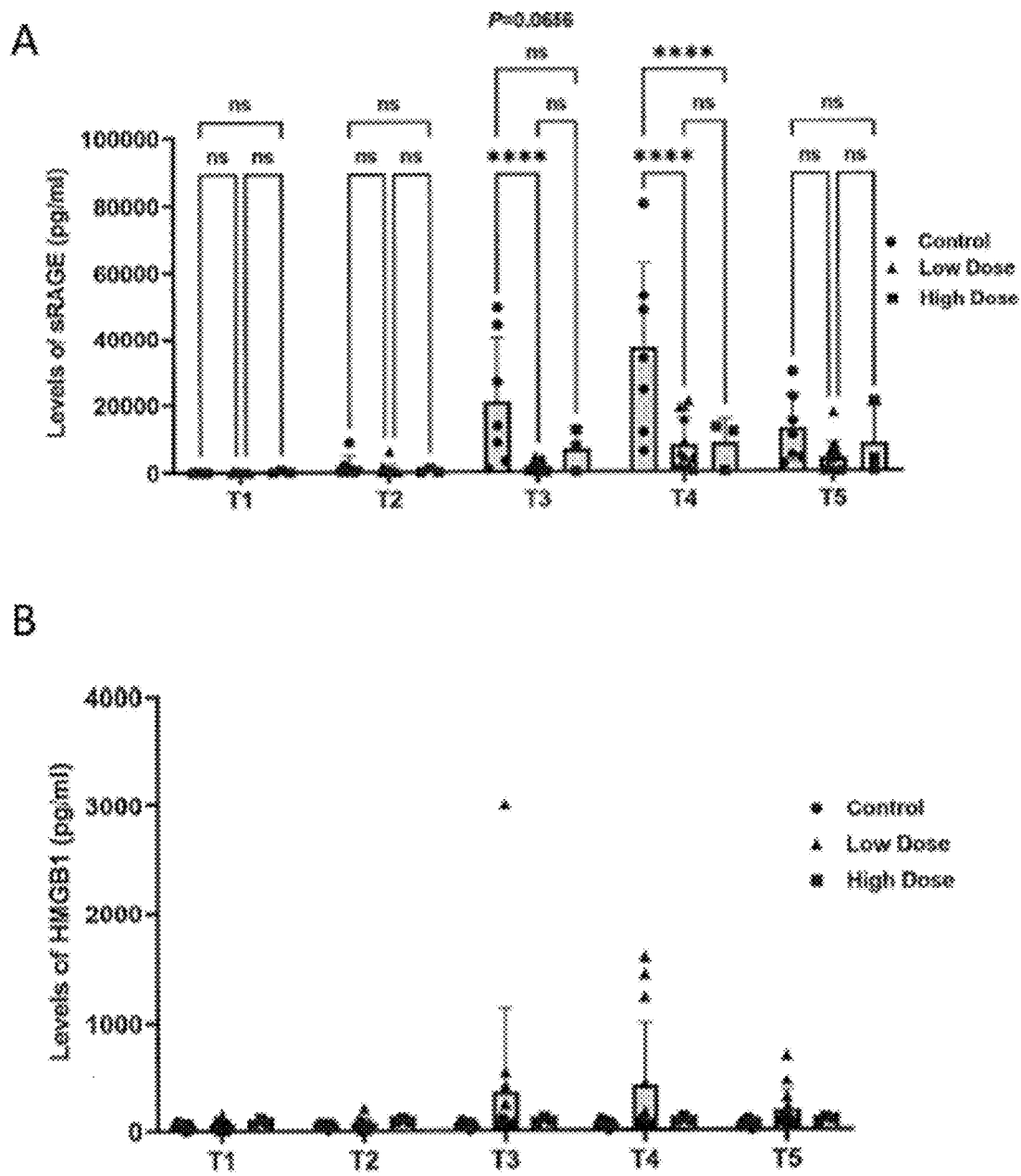
FIG. 21. Plasma levels of soluble receptor for advanced glycation end-products (sRAGE) and high mobility group box 1 protein (HMGB1) in regadenoson-treated and the control lung transplant recipients. Bar graphs show the plasma levels of sRAGE (A) and HMGB1 (B) at indicated timepoints. T1, prior infusion (baseline); T2, 15 minutes before reperfusion of the 1st lung; T3, 30 minutes after reperfusion of 1st lung; T4, 30 minutes after reperfusion of 2nd lung; TS, 6 hours after reperfusion of 1st lung. Low dose: 1.44 ug/kg/hour, n=14; High dose: 2.88 ug/kg/hour, n=3; and Control: lung transplant patients treated with saline, n=7. ****: p<0.0001.

Publications showed that elevated recipient levels of plasma sRAGE 6 and 24 hours after reperfusion were associated with the development of POD within the first seventy-two hours after transplant (CHRISTIE et al., Am J Respir Crit Care Med, (2009), 180:1010-1015; SHAH et al., J Heart Lung Transplant, (2012), 31:942-949). Our current result revealed that plasma levels of sRAGE started to elevate as early as 30 minutes after 1st lung reperfusion (FIG. 21A). It is important to detect levels of biomarkers as earlier as possible, so that early intervention can be employed to prevent PGD progression. Therefore, sRAGE can be used as a biomarker for lung IR injury/PGD at the vely early-stage post lung reperfusion. Our results also provide a new mechanism for anti-inflammatory effects of $A_{2A}R$ agonists/activation in lung IR injury through regulation of sRAGE and MMP-9.

MMP-9 played an important role in acute lung injury post lung transplantation and lung IRI (NATAATMADJA et al., Lung, (2014), 192:563-569; VAN DER KAAIJ NP et al., Respir Res, (2008), 9:28; QU et al., J Surg Res, (2019), 235:569-577; JU et al., Cell Transplant, (2019), 28:1674-1685). It is also one of the known enzymes that shed sRAGE by cleaving the membrane-anchored full-length RAGE (ZHANG et al., J Biol Chem, (2008), 283:35507-35516; METZ et al., PLoS One, (2012), 7:e41823). In our current lung transplantation study, we revealed that regadenoson not only reduced plasma levels of sRAGE, but also inhibited MMP-9 levels in the same cohort of patients. These results indicate that $A_{2A}R$ agonists may reduce sRAGE levels by inhibiting MMP-9 in regadenoson treated lung transplantation patients. Next, we identified that invariant natural killer T cells and monocytes expressed higher levels of $A_{2A}R$ in these patients (FIG. 23C). Published data showed that monocytes/macrophages and alveolar macrophages expressed high levels of RAGE (STAITIEH et al., Am J Med Sci, (2018), 355:497-505; WANG et al., J Immunol, (2010), 185:1822-1835). To test our hypothesis that $A_{2A}R$ agonist may reduce sRAGE levels by inhibiting MMP-9, we employed mouse alveolar macrophages (MRS) and another monocyte/macrophage cell line, RAW 264.7, in cell culture model. The results clearly showed that both MRS and Raw cells produced RAGE and MMP-9. Treat the cells with MMP-9 stimulator (PMA) and monocytes activator (LPS) significantly increased MMP-9 production, but not MMP-2 (FIGS. 24A, 25A & 26A). The levels of sRAGE in PMA/LPS-treated cell culture media is significantly elevated (FIG. 24B), while the cell membrane bounded RAGE is reduced (FIGS. 24C, 25B & 26A). The PMA-induced shedding of sRAGE was partially blocked by adding MMP-9 inhibitor (GM6001). Interestingly, the PMA-induced shedding of sRAGE was also partially inhibited by two $A_{2A}R$ agonists, regadenoson and apadenoson (FIGS. 24B, 25B). These results suggest that monocytes/macrophages may at least partially contribute to sRAGE shedding by MMP-9 in the early stage of lung reperfusion.

$A_{2A}R$ agonist may suppress MMP-9 production via several pathways. It is known that MMP-9 expression is up-regulated by ROS and the activation of the RAS-ERK-NF-kB pathway (KOWLURU et al., Expert Opin Investig Drugs, (2012), 21:797-805).

Since $A_{2A}R$ agonist inhibited NFkB activation, thus regadenoson may reduce MMP-9 by inhibiting NF-kB activation (CAMPO et al., Matrix Biol, (2012), 31: 338-351). TNF-a can also increase MMP-9 expression, which subsequently increase RAGE shedding (LAPAR et al., J Thorac Cardiovasc Surg, (2011), 142: 887-894; MIYOSHI et al., Faseb j, (2019), 33:3575-3589). $A_{2A}R$ agonists inhibit TNF-α production in mouse articular chondrocytes (51) and in lung IR injury (CAMPO et al., Matrix Biol, (2012), 31: 338-351; SCHEIBNER et al., Am J Respir Cell Mol Biol, (2009), 40: 251-259; SHARMA et al., J Thorac Cardiovasc Surg, (2010), 139:474-482). It is possible that regadenoson may inhibit MMP-9 through decreasing TNF-a production. Interestingly, we also find that regadenoson infusion significantly increased plasma levels of TIMP-1 (FIG. 22E), which is an endogenous specific MMP-9 inhibitor (KIM et al., PLoS One, (2012), 7:e33664; FOTOPOULOS et al., Knee Surg Sports Traumatol Arthrosc, (2012), 20:1159-1167). Therefore, regadenoson may not only suppress lung transplantation-induced MMP-9 production, but also inhibit its proteolytic activity by increasing its specific inhibitor, TIMP-1. Another interesting finding is that $A_{2A}R$ agonists are not reduced PMA-induced MMP-9 levels, but reduced LPS-induced MMP-9 levels. PMA is a known protein kinase C agonist, which activate neutrophil NADPH-oxidase and lead to ROS activation (KARLSSON et al., J Leukoc Biol, (2000), 67:396-404).

While LPS is a well-known monocyte/macrophage activator (TUCUREANU et al., Int J Nanomedicine, (2018), 13: 63-76). These results suggest that $A_{2A}R$ agonist may work through different mechanisms depend on stimulators and type of cells. For examples, $A_2AR$ agonist may reduce MMP-9 levels in PMA-activated neutrophils through ROS pathway, which is a down-stream target for $A_{2A}R$ activation and one of the MMP-9 induction pathways (KOWLURU et al., Expert Opin Investig Drugs, (2012), 21:797-805; ZHAO et al., Int J Biol Sci, (2019), 15:1571-1581). We are investing a possible mechanism that $A_{2A}R$ agonists may stimulate TIMP-1 to inhibit MMP-9 activity rather than reducing MMP-9 levels in these PMA-treated monocytes/macrophages.

In summary, regadenoson exhibit protective effects on lung transplantation by reducing plasma levels of sRAGE and MMP-9 while elevating TIMP-1. MMP-9 shed cell membrane bounded RAGE in alveolar macrophages (MHS) and monocyte/macrophage-like cells (Raw) in in vitro cell culture model. The MMP-9 mediated sRAGE shedding was suppressed by MMP inhibitor and $A_{2A}R$ agonists. These results indicate a new mechanism and through which $A_{2A}R$ agonist may protect lung IR injury. These fundings may also applied to other inflammatory lung diseases.

Example 6. SARS-CoV-2 Strain B.1.351 (South African Variant) in Syrian Hamster Response to Treatment with Regadenoson and Apadenoson Described below is a study performed in hamsters infected with SARS-CoV-2 strain B.1.351 and treated with regadenoson and apadenoson.

Figure 33:
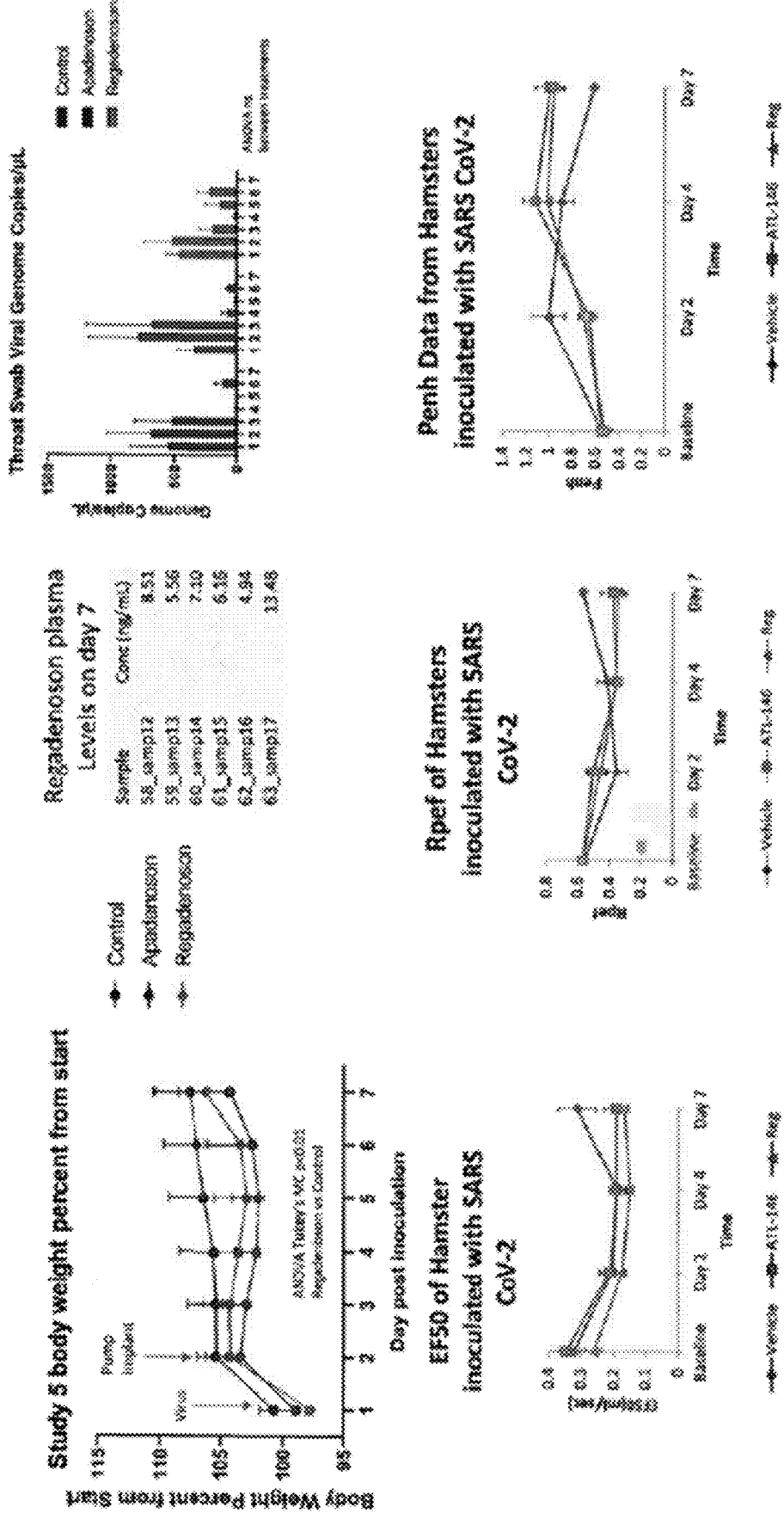
FIG. 33. Results: Hamster Study Apadenoson (ATL146e) and Regadenoson.
Figure 34:
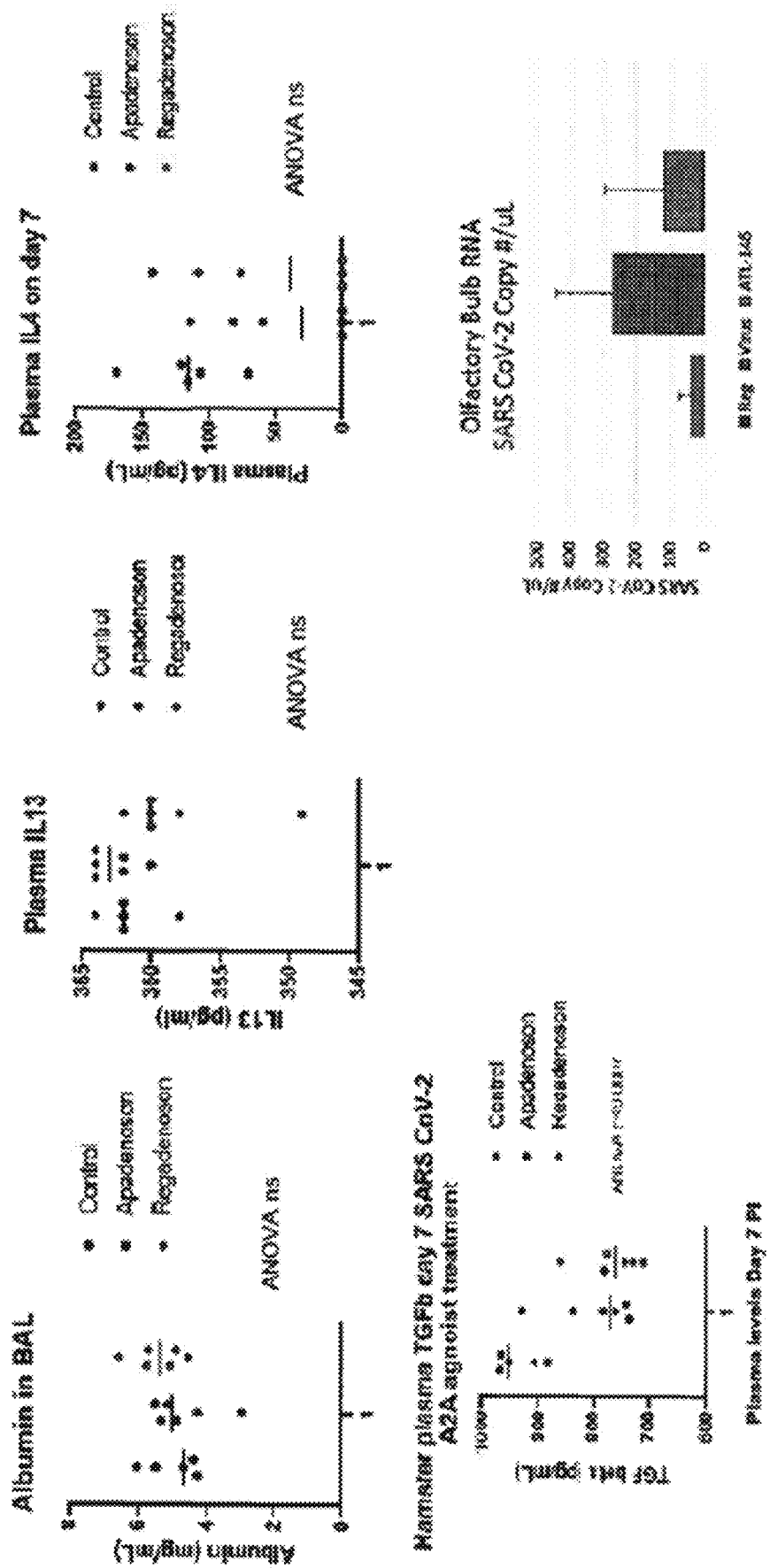
FIG. 34. Hamster Study ATL146e and Regadenoson-125, 000 PFU intra-tracheal, therapy 24 hours later.

Experimental Design
- 90-100 gm Golden Syrian male hamsters acquired from Charles River Laboratories
- Intra-tracheal inoculation of 125,000 PFU of SARS-CoV-2 strain B.1.351. in 50 μL under ketamine/xylazine/acepromazine anesthesia. Three groups all (n=G) receiving 2N1 Alzet minipump (μL/hr) implant one day after viral inoculation
- Control—pump contains phosphate buffered saline (PBS)
- Regadenoson—80 μg/ml in PBS
- Apadenoson—80 μg/ml in PBS
- Hamsters are weighed daily and assessed clinically
- Throat swabs taken days for relative viral titer by RT-qPCR
- Whole body plethysmography performed days 0, 2, 4 and 7
- Euthanized day 7, blood collected with EDTA anticoagulant for plasma cytokine analysis, plasma regadenoson quantitation by mass spectroscopy, PBS used for bronchoalveolar lavage (BAL), lungs insufflated with neutral buffered formalin for histology
- One olfactory bulb collected for RT-PCR prior to fixation of the brain for histology Results as shown in FIG. 33.

Hamsters did not die in response to SARS Cov-2 Infection.

Weight gain slowed in all groups beginning day 2 after virus inoculation. $A_{2A}$ agonist treated groups were more greatly affected than the control group. Weight gain was similar in all 3 groups by P1 day 7

Viral titer of throat swabs reached peak value by day 2 P1 in all groups, undetectable in all groups by P1 day 7.

Therapeutic levels of Regadenoson in plasma were achieved by day 7 as determined by mass spectroscopy. The mean +/−SEM plasma level for Regadenoson was 7.6+/−1.3 ng/ml.
- Whole body plethysmography showed changes on day 7. $A_{2A}$ agonists groups show: slight decrease in peak expiratory flow (EFSO), decrease in time to 50% expiratory flow in $A_{2A}$ treatment groups (Rpef) and increase in airway resistance to flow (Penh) compared to untreated control.

Results as shown in FIG. 34.

- Albumin leakage into BAL as a measure of integrity of alveolar vascular barrier integrity—slight increase in Regadenoson treated group compared to control group, slight decrease in Apadenoson treated group on P1 day 7.
- Plasma IL13 slightly elevated in Apadenoson group, and slightly depressed in Regadenoson group, compared to control group on P1 day 7.
- Plasma IL4 depressed in Apadenoson group and Regadenoson groups compared to control
- Plasma Transforming Growth Factor beta (TGFb) decreased in Apadenoson and Regadenoson groups on day 7, compared to control
- Spread of virus to olfactory bulb (brain) was decreased in Apadenoson and Regadenoson groups on day 7, compared to control Results as shown in FIGS. 35 and 31.

- Lesions characterized as chronic-active multifocal bronchopneumonia with interstitial pneumonitis.
- Severity of histological lesions were not substantially diminished in treatment groups when compared to control.

CONCLUSIONS

- Treatment with Regadenoson and Apadenoson did not significantly:
- Alter the decrease in weight gain in hamsters associated with B1.351. SARS CoV-2 pneumonia
- Change the time course of the disease or viral titer detected in throat swabs Improve respiratory physiology parameters measured on P1 day 7: {EFSO-decrease expiratory flow rate, Rpef-increase time to peak flow, Penh—increase airway resistance to flow).
- Decrease albumin leakage into alveoli or decrease plasma IL13 P1 day 7.
- Diminish the histologic distribution or severity of lung pathology
- Treatment with Regadenoson and Apadenoson did significantly:
- Decrease IL4 (IL4 suppresses B-lymphocyte activity and induces Th2 response)
- Decrease TGFb (predicted to decrease propensity for pulmonary fibrosis, decrease
- inhibition of B-lymphocyte proliferation)
- Decrease viral spread into the brain via the olfactory bulb While the present teachings are described in conjunction with various embodiments, it is not intended that the present teachings be limited to such embodiments. On the contrary, the present teachings encompass various alternatives, modifications, and equivalents, as will be appreciated by those of skill in the art.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

What is claimed is:

1. A method of treating cytokine storm syndrome comprising administering to a patient in need thereof a therapeutically effective amount of an adenosine A2A receptor agonist, wherein the agonist is ATL-146(e) (apadenoson).

2. The method of claim 1, wherein the cytokine storm is caused by a viral, bacterial, or fungal infection.

3. The method of claim 1, wherein from 0.1-100 μg/h of the A2A agonist is administered to the subject.

4. The method of claim 1, wherein theA2A agonist is administered by an infusion.

5. The method of claim 1, wherein the A2A agonist is administered from 1-48 hours.

6. The method of claim 1, wherein the patient is first administered a loading dose of 100-1000 μg followed by a maintenance dose.

7. The method of claim 1 Previously, wherein the agonist is delivered by a route selected from the group consisting of intravenously (IV), intramuscularly (IM), orally, via aerosol, and transdermally.

8. The method of claim 1, wherein the agonist is delivered by an IV infusion.

9. The method of claim 1, wherein the cytokine storm syndrome is caused by a viral infection.

10. The method of claim 1, wherein the method further comprises administering a therapeutically effective amount of an anti-viral agent.

11. The method of claim 1, wherein the cytokine storm syndrome is caused by a bacterial infection.

12. The method of claim 11, wherein the method further comprises administering a therapeutically effective amount of an antibiotic.

13. The method of claim 1, wherein the cytokine storm syndrome is caused by a fungal infection.

14. The method of claim 13, wherein the method further comprises administering a therapeutically effective amount of an anti-fungal agent.

15. The method of claim 1, wherein the cytokine storm syndrome is caused by an infection selected from the group consisting of a coronavirus (SARS-COV-2, MERS-COV, and SARS-COV), human metapneumovirus (HMPV), human parainfluenza virus (HPIV), influenza (Flu), respiratory syncytial virus (RSV), a rhinovirus (RV-A, RV-B, or RV C), an adenovirus, *Haemophilus influenzae*, measles virus, varicella-zoster virus, *Legionella* (Legionnaires' Disease), *Mycoplasma pneumoniae, Streptococcus pneumoniae* (or pneumococcus, Pneumococcal disease), *Pneumocystis jirovecii* (*Pneumocystis* pneumonia), *Bordetella pertussis* (whooping cough), *Chlamydia pneumoniae, Chlamydia psittaci* (psittacosis), *Blastomyces dermatitidis* (Blastomycosis), *Cryptococcus gattii, Paracoccidioides brasiliensis* (Paracoccidioidomycosis), *Coccidioides immitis* (Coccidioidomycosis), *Coccidioides posadasii* (Coccidioidomycosis), and *Histoplasma capsulatum* (Histoplasmosis).

16. The method of claim 15, wherein the infection is a viral infection caused by SARS-COV-2.

17. The method of claim 1, wherein the administering comprises:
(a) administering a loading dose of the A2A agonist, wherein the loading dose is from 1-1000 μg; and
(b) administering a maintenance dose of the A2A agonist, wherein the maintenance dose is from 0.1-10 μg/kg/h.

18. The method of claim 17, wherein the loading dose is administered as a IV injection within 60 minutes.

19. The method of claim 17, wherein the maintenance dose is administered for 1-48 h.

20. The method of claim 17, wherein the maintenance dose is from 0.01-100 μg/kg/h and is administered for 1-48 h.

21. The method of claim 1, wherein the ATL146e, is intravenously administered as a loading dose of from 100-500 ug within 30 min and a maintenance dose of from 0.1-10 μg/kg/h for 3-48 h.

22. The method of claim 1, wherein ATL146e, is intravenously administered as a bolus at a loading dose of from 200 600 μg within 30 min and a maintenance dose of from 0.1-10 μg/kg/h for 6-48 h.

23. The method of claim 1, wherein the A2A receptor agonist is an allosteric activator of the adenosine A2A receptor.

* * * * *